(12) United States Patent
Hosokawa et al.

(10) Patent No.: US 9,650,353 B2
(45) Date of Patent: May 16, 2017

(54) METHOD FOR PRODUCING EPOXY COMPOUND AND CATALYST COMPOSITION FOR EPOXIDATION REACTION

(71) Applicant: MITSUBISHI CHEMICAL CORPORATION, Chiyoda-ku (JP)

(72) Inventors: Akemi Hosokawa, Kanagawa (JP); Haruhiko Kusaka, Kanagawa (JP)

(73) Assignee: MITSUBISHI CHEMICAL CORPORATION, Chiyoda-ku (JP)

(*) Notice: Subject to any disclaimer, the term of this patent is extended or adjusted under 35 U.S.C. 154(b) by 0 days.

(21) Appl. No.: 14/502,206

(22) Filed: Sep. 30, 2014

(65) Prior Publication Data

US 2015/0018515 A1    Jan. 15, 2015

Related U.S. Application Data

(63) Continuation of application No. PCT/JP2013/059401, filed on Mar. 28, 2013.

(30) Foreign Application Priority Data

Mar. 30, 2012 (JP) ................. 2012-082139
Oct. 12, 2012 (JP) ................. 2012-226995
Jan. 25, 2013 (JP) ................. 2013-012207

(51) Int. Cl.

| | |
|---|---|
| C08G 59/18 | (2006.01) |
| C07D 301/03 | (2006.01) |
| C07D 301/12 | (2006.01) |
| B01J 31/34 | (2006.01) |
| C07D 303/27 | (2006.01) |
| C08G 59/02 | (2006.01) |
| B01J 31/02 | (2006.01) |
| C07D 303/30 | (2006.01) |

(52) U.S. Cl.
CPC ........ *C07D 301/12* (2013.01); *B01J 31/0239* (2013.01); *B01J 31/34* (2013.01); *C07D 303/27* (2013.01); *C07D 303/30* (2013.01); *C08G 59/02* (2013.01); *C08G 59/027* (2013.01); *B01J 2231/72* (2013.01)

(58) Field of Classification Search
None
See application file for complete search history.

(56) References Cited

U.S. PATENT DOCUMENTS

| | | | |
|---|---|---|---|
| 3,728,320 A * | 4/1973 | Vandenberg | C08G 65/08 525/403 |
| 4,552,604 A | 11/1985 | Green | |
| 4,731,373 A | 3/1988 | Barner et al. | |
| 5,110,977 A | 5/1992 | Wilson et al. | |
| 5,185,334 A | 2/1993 | Solomon et al. | |
| 5,187,293 A | 2/1993 | Barner et al. | |
| 5,194,472 A | 3/1993 | Wilson et al. | |
| 5,274,140 A | 12/1993 | Venturello et al. | |
| 5,449,680 A | 9/1995 | Solomon et al. | |
| 5,578,740 A | 11/1996 | Au et al. | |
| 5,908,943 A | 6/1999 | Au et al. | |
| 6,043,383 A | 3/2000 | Kuroda et al. | |
| 6,054,407 A | 4/2000 | Schulz et al. | |
| 2007/0043234 A1 | 2/2007 | Vaultier et al. | |
| 2007/0093667 A1 | 4/2007 | Watanabe et al. | |
| 2009/0082583 A1 | 3/2009 | Watanabe et al. | |
| 2011/0263882 A1 | 10/2011 | Uchida | |

FOREIGN PATENT DOCUMENTS

| | | |
|---|---|---|
| CN | 1201406 A | 12/1998 |
| CN | 101457013 A | 6/2009 |
| CN | 102264712 A | 11/2011 |
| JP | 53-97035 | 8/1978 |
| JP | 56-18972 A | 2/1981 |
| JP | 60-158172 A | 8/1985 |
| JP | 3-501612 A | 4/1991 |
| JP | 4-213465 A | 8/1992 |
| JP | 10-511721 A | 11/1998 |
| JP | 2000-26441 A | 1/2000 |
| JP | 2001-17863 A | 1/2001 |
| JP | 2011-213716 A | 10/2001 |
| JP | 2002-69079 A | 3/2002 |
| JP | 2004-59573 A | 2/2004 |
| JP | 2005-010770 A | 1/2005 |
| JP | 2007-301466 A | 11/2007 |
| JP | 2009-185274 A | 8/2009 |
| JP | 2010-18538 A | 1/2010 |
| JP | 2010-70480 A | 4/2010 |
| JP | 2010-83836 A | 4/2010 |
| JP | 2010-95521 A | 4/2010 |
| JP | 2010-106009 A | 5/2010 |
| JP | 2010-235649 A | 10/2010 |
| JP | 2011-1499 A | 1/2011 |
| JP | 2011-213716 A2 | 10/2011 |
| JP | 2011-225711 A | 11/2011 |
| JP | 2012-116782 A | 6/2012 |
| JP | 2013-112639 A | 6/2013 |
| WO | WO 96/20232 A1 | 7/1996 |
| WO | WO 2004/096440 A1 | 11/2004 |
| WO | WO 2010/073960 A1 | 7/2010 |
| WO | WO 2011/019061 A1 | 2/2011 |
| WO | WO 2012/137225 A1 | 10/2012 |

OTHER PUBLICATIONS

Combined Chinese Office Action and Search Report issued Sep. 11, 2015 in Patent Application No. 201380018506.9 (with English language translation).

(Continued)

*Primary Examiner* — Michael J Feely
(74) *Attorney, Agent, or Firm* — Oblon, McClelland, Maier & Neustadt, L.L.P.

(57) ABSTRACT

A method of producing an epoxy compound, which comprises reacting hydrogen peroxide with a compound having a carbon-carbon double bond, in the presence of at least one of a tungsten compound and a molybdenum compound; and an onium salt comprising 20 or more carbon atoms and one or more of substituents convertible to a functional group containing an active hydrogen or a salt thereof.

21 Claims, No Drawings

(56) References Cited

OTHER PUBLICATIONS

"STN-Registry" STN Columbus, Dec. 10, 2008, 4 Pages.
Santanu Bhattacharya et al., "Surfactant Lipids Containing Aromatic Units Produce Vesicular Membranes with High Thermal Stability", Chemistry and Physics of Lipids, vol. 78, No. 2, 1995, pp. 177-188.
Kazuhiko Sato et al., "A Halide-Free Method for Olefin Epoxidation with 30% Hydrogen Peroxide", Bulletin of the Chemical Society of Japan, vol. 70, No. 4, 1997, pp. 905-915,.
Andrew T. McPhail et al., "Triphase Catalysis", Journal of American Chemical Society, vol. 90, 1975, pp. 5956-5957.
Yasutaka Ishii et al., "Hydrogen Peroxide Oxidation Catalyzed by Heteropoly Acids Combined with Cetylpyridinium Chloride: Epoxidation of Olefins and Allylic Alcohols, Ketonization of Alcohols and Diols, and Oxidative Cleavage of 1,2-Diols and Olefins", *J. Org. Chem.*, vol. 53, 1988, pp. 3587-3593.
International Search Report issued Jul. 2, 2013 in PCT/JP2013/059401.
Carlo Venturello et al., "Quaternary Ammonium Tetrakis(diperoxotungsto)phosphates(3-) as a New Class of Catalysts for Efficient Alkene Epoxidation with Hydrogen Peroxide", J. Org. Chem. , vol. 53, 1988, pp. 1553-1557.
Combined Chinese Office Action and Search Report issued Apr. 14, 2016 in Patent Application No. 201380018506.9 (with English language translation).
Office Action dated Feb. 28, 2017 issued in corresponding Japanese patent application No. 2014-508066 (with English translation).
Office Action dated Feb. 13, 2017 issued in corresponding Taiwanese patent application No. 102111394 (with English translation).

\* cited by examiner

METHOD FOR PRODUCING EPOXY COMPOUND AND CATALYST COMPOSITION FOR EPOXIDATION REACTION

TECHNICAL FIELD

The present invention relates to a method for producing a novel epoxy compound and a novel catalyst composition for an epoxidation reaction.

BACKGROUND ART

An epoxy compound is being widely utilized as an epoxy monomer working out to a raw material of an epoxy resin or as a raw material of various chemical products.

The epoxy resin is a resin obtained by curing an epoxy monomer by using various curing agents. The epoxy resin is a resin excellent in the mechanical property, water resistance, chemical resistance, heat resistance, electric property and the like and is used in a wide range of fields such as electronic material, optical material, building material, adhesive, coating material, laminated plate, molding material, casting material and resist.

Recently, the increased integration in the electronic material field, for example, fields of semiconductor sealing material, printed wiring board, build-up wiring board and solder resist, accompanies requirement to highly purify also a package material typified by an epoxy resin. Furthermore, in the optoelectronics-related field, highly advanced informatization in recent years leads to the development of a technique utilizing optical signals so as to smoothly transmit and process vast amounts of information and amid this trend, development of a high-purity resin excellent in the transparency is demanded.

With such growing needs for a high-purity epoxy resin, high purification is required also of the epoxy monomer working out to a material of the epoxy resin.

A glycidyl ether compound as a representative epoxy monomer, for example, a compound obtained by fusing a glycidyl oxy group to phenols, naphthols, bisphenol A, etc., is excellent in the heat resistance, adhesiveness, chemical resistance, electric properties, mechanical properties and the like and therefore, is an industrial material finding many applications such as adhesive, molding material, sealing material and coating material when crosslinked/cured by a curing agent. As the production method of the glycidyl ether compound, in the case of using phenols as the raw material, a method of reacting epichlorohydrin with the raw material phenols is most widely employed. A specific method for synthesizing a glycidyl ether by using epichlorohydrin is represented, for example, by the following reaction formula:

[Chem. 1]

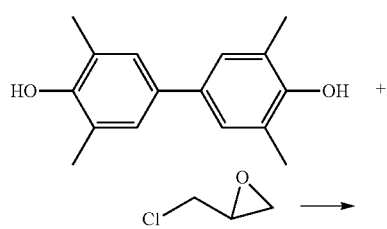

-continued

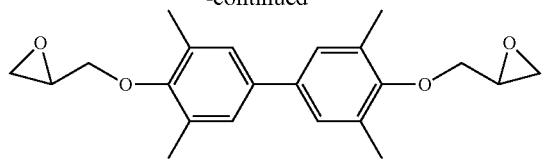

However, in the epoxy compound obtained by the above-described method, a chlorine atom derived from epichlorohydrin is mixed as an impurity in the form of being chemically bonded to the compound. Therefore, the chlorine concentration in the epoxy compound is high. Specifically, chlorine is usually contained at a concentration of 1,000 ppm or more. When an epoxy resin produced from an epoxy compound (epoxy monomer) having such a high chlorine concentration is used for an IC sealing material, there is a problem that corrosion or breakage of wiring is likely to occur due to refinement of the circuit for high integration.

To avoid such a problem, an epoxidation method not using epichlorohydrin is demanded. As the production method to meet this demand, a method of condensing an allyl alcohol by the use of a palladium catalyst to form an allyl ether and then obtaining an epoxy compound by the use of hydrogen peroxide or an organic peroxide has been advocated (see, for example, Patent Document 1). However, this method is not a practical method, because the palladium is very expensive and for preventing the residual palladium from contacting with an oxide such as peroxide to decompose the peroxide, a cumbersome process of purifying and removing the palladium is necessary.

A method of producing an allyloxy form with a low chlorine content and oxidizing the allyloxy form to effect conversion to an epoxy compound, thereby synthesizing a glycidyl ether having a low chlorine content, has been recently developed (see, for example, Patent Documents 2 and 3).

The epoxidation reaction employed in this production method is generally performed by allowing onium salts such as ammonium salt and at least either a tungsten compound or a molybdenum compound to exist together and using hydrogen peroxide as an oxidant (epoxidizing agent) (see, for example, Non-Patent Documents 1 to 3).

This epoxidation reaction generates only water as a byproduct and therefore, is a clean reaction producing less waste, compared with an epoxidation reaction using an organic peroxide typified by peracetic acid. In addition, since aqueous hydrogen peroxide of 30 to 45% is used, the procurement and handling are easy and simple.

However, in this epoxidation reaction, the oxidant is prepared using, as an onium salt usually allowed to coexist as a catalyst, an ammonium salt having a long-chain alkyl group, such as methyltrioctylammonium chloride, or a pyridinium salt having a long-chain alkyl group, such as cetylpyridinium salt. The onium salt having a long-chain alkyl group has a high distribution factor to an organic solvent and poses a problem that it is very difficult to, after the reaction, separate and purify the epoxy compound dissolved in the organic phase from the catalyst composition-derived components, specifically, tungsten, an onium salt, and an onium salt-derived nitrogen-containing compound. Furthermore, when tungsten, a nitrogen-containing compound and the like are removed by a method such as recrystallization and suspension-washing, there is a problem that the purification yield (recovery percentage) of the epoxy compound is low.

Therefore, catalyst-derived heavy metal components such as tungsten and molybdenum, or ionic compounds such as onium salt, remain in the obtained epoxy compound. These components or compounds remain also in an epoxy resin produced from the epoxy compound and adversely affect the product.

Specifically, it has been reported that in the case where a heavy metal such as tungsten remains in the epoxy compound, an epoxy resin produced using the epoxy compound develops significant coloration when left standing under high-temperature conditions (see, for example, Patent Document 4). Also, in the case of using the epoxy resin for an electronic material, a halogen such as chlorine remaining in the epoxy compound gives rise to corrosion of wiring, and the remaining metal or ionic compound such as onium salt gives rise to short circuit or corrosion of wiring.

As the method for solving this problem, several methods have been reported.

For example, in Patent Document 5 or 6, a method where, after the epoxidation ration, the ammonium salt is absorbed and removed by using, as an adsorbent, an ion-exchange resin, a metal oxide or the like, is studied.

Also, in Patent Documents 7 and 8 and Non-Patent Document 4, a method where the ammonium salt employed for the epoxidizing agent is used in the state of being supported on a resin, silica gel or the like and then separated/recovered by filtration, is studied.

In Patent Document 9, a method where an ammonium salt used as the catalyst is precipitated after the epoxidation reaction, is studied.

In addition, in Patent Document 10, a method of disproportionating the catalyst is studied.

Furthermore, in Patent Document 11, a method of removing an ammonium salt by binding a magnetic material thereto is studied.

RELATED ART

Patent Document

Patent Document 1: JP-T-10-511721 (the term "JP-T" as used herein means a published Japanese translation of a PCT patent application)
Patent Document 2: JP-A-2011-213716 (the term "JP-A" as used herein means an "unexamined published Japanese patent application")
Patent Document 3: International Publication No. 2011/019061
Patent Document 4: JP-A-2009-185274
Patent Document 5: JP-A-2010-70480
Patent Document 6: JP-A-2010-235649
Patent Document 7: JP-A-2002-69079
Patent Document 8: JP-A-2001-17863
Patent Document 9: JP-A-2010-83836
Patent Document 10: International Publication No. 2004/096440
Patent Document 11: JP-A-2007-301466

Non-Patent Document

Non-Patent Document 1: J. Org. Chem., vol. 53 pp. 1553-1557 (1988)
Non-Patent Document 2: J. Org. Chem., vol. 53 pp. 3587-3595 (1988)
Non-Patent Document 3: Bull. Chem. Soc. Jpn., 70, 4 (1997)
Non-Patent Document 4: Journal of the American Chemical Society, Vol. 90, pp. 5956-5957 (1975)

SUMMARY OF THE INVENTION

Problems that the Invention is to Solve

However, in the method described in Patent Document 5 or 6, an adsorbent must be charged in an amount of 15 wt % or more based on the epoxy compound and in addition, an operation of separating the adsorbent is required.

Furthermore, use of an adsorbent leads to a fear of reduction in productivity due to adsorption loss of the epoxy compound to the adsorbent or elution and mixing of an ion exchange resin-derived organic impurity or a metal oxide-derived metal.

In the case of fixing the catalyst component on a support as described in Patent Documents 7 and 8 or Non-Patent document 4, the activity of the catalyst is reduced, and there arises a new problem, for example, that a large amount of a catalyst is required, the usable solvent is limited so as to avoid swelling of the resin on which the catalyst is supported, or the catalyst thermal stability deteriorates.

In Patent Document 9, it is stated that the tungsten amount can be reduced only to about 600 ppm at the most by a precipitation operation alone.

In the method described in Patent Document 10, the disproportionation involves a problem, for example, that the reaction rate is reduced or the method cannot be applied to a monomer having good crystallinity.

The method described in Patent Document 11 has a problem that the catalyst synthesis is cumbersome.

In this way, it has been difficult with all of those conventional methods to produce an epoxy compound reduced in the content of a heavy metal component such as tungsten or a nitrogen-containing compound derived from an onium salt.

The oxide such as hydrogen peroxide causes decomposition, heat generation, oxygen generation or the like upon contact with a foreign material such as metal, activated carbon, silica gel and glass piece and therefore, mixing of such a foreign material in the epoxidation reaction solution is preferably avoided, but it is difficult to completely prevent mixing of a foreign material in the production process, and taking safety measures is required.

An object of the present invention is to provide a method for producing an epoxy compound having a very small content of a heavy metal such as tungsten, preferably further having a small content of an onium salt-derived nitrogen-containing compound (hereinafter, simply referred to as the nitrogen content), more preferably further having a small chlorine content, without requiring a cumbersome purification process and the like.

Means for Solving the Problems

The present inventors have designed a compound by incorporating a new concept, that is, introduction of a structure convertible to an easily removable compound, into an onium salt caused to coexist as a catalyst, and used the compound for the epoxidation reaction.

Specifically, the reaction was performed in coexistence of an onium salt having, in the molecule, at least one or more substituents that are convertible to an active hydrogen-containing functional group or a salt thereof. As a result, it has been found that an objective epoxy compound is obtained and when conversion to an active hydrogen-containing functional group or a salt thereof is effected after the epoxidation reaction, the epoxidizing agent-derived components are separated and removed from the epoxy compound, resulting in obtaining an epoxy compound with high purity. The present invention has been accomplished based on this finding.

That is, the gist of the present invention resides in the followings.

[1] A method for producing an epoxy compound, comprising reacting hydrogen peroxide with a compound having a carbon-carbon double bond in the presence of at least one of a tungsten compound and a molybdenum compound; and an onium salt having 20 or more carbon atoms and containing one or more substituents convertible to an active hydrogen-containing functional group or a salt thereof.

[2] The method for producing an epoxy compound as described in the [1] above, wherein said active hydrogen-containing functional group is a hydroxyl group, a carboxyl group, an amino group, a mercapto group, a sulfonic acid group or a phosphoric acid group.

[3] The method for producing an epoxy compound as described in the [1] or [2] above, wherein at least one of phosphoric acids and phosphonic acids (excluding an onium salt) is further allowed to coexist in said reaction.

[4] The method for producing an epoxy compound as described in any one of the [1] to [3] above, wherein said reaction is a two-phase reaction of an aqueous phase and an organic phase and the pH of said aqueous phase is from 2 to 6.

[5] The method for producing an epoxy compound as described in any one of the [1] to [4] above, wherein said onium salt is an ammonium salt, a pyridinium salt, an imidazolinium salt or a phosphonium salt.

[6] The method for producing an epoxy compound as described in any one of the [1] to [5] above, wherein said substituent convertible to an active hydrogen-containing functional group or a salt thereof is an alkoxycarbonyl group or an acyloxy group.

[7] The method for producing an epoxy compound as described in any one of the [1] to [6] above, wherein said onium salt is a compound represented by any one of the following formulae (1) to (3):

[Chem. 2]

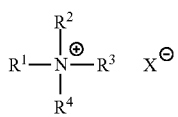

(1)

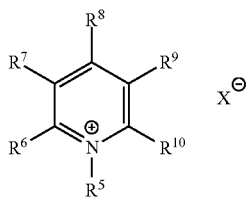

(2)

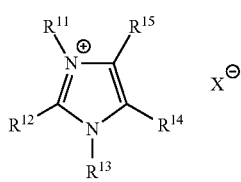

(3)

(in formulae (1) to (3), each of any one or more of $R^1$ to $R^4$, any one or more of $R^5$ to $R^{10}$ and any one or more of $R^{11}$ to $R^{15}$ independently represents —Y—CO—O—Z or —Y—O—CO—Z (wherein Y represents a direct bond or a divalent aliphatic hydrocarbon group having a carbon number of 1 to 25, in which a part of carbon atoms may be substituted with a heteroatom and which may have a substituent, and Z represents a monovalent aliphatic hydrocarbon group having a carbon number of 1 to 25, in which a part of carbon atoms may be substituted with a heteroatom, or a monovalent aromatic hydrocarbon group having a carbon number of 4 to 25, which may have a substituent), each of $R^1$ to $R^5$, $R^{11}$ and $R^{13}$, when these are not —Y—CO—O—Z or —Y—O—CO—Z, independently represents an alkyl group having a carbon number of 1 to 25, in which a part of carbon atoms may be substituted with a heteroatom and which may have a substituent, or a benzyl group, each of $R^6$ to $R^{10}$, $R^{12}$, $R^{14}$ and $R^{15}$, when these are not —Y—CO—O—Z or —Y—O—CO—Z, independently represents a hydrogen atom, a halogen atom, a cyano group, a nitro group, an alkyl group having a carbon number of 1 to 25, in which a part of carbon atoms may be substituted with a heteroatom and which may have a substituent, a phenyl group, a phenoxy group, a benzyl group, an N-alkylcarbamoyl group or an N-alkylsulfamoyl group, $R^1$ to $R^{15}$ may combine in the same compound to form a ring, provided that the total number of carbon atoms contained in $R^1$ to $R^4$ in formula (1) is 20 or more, the total number of carbon atoms contained in $R^5$ to $R^{10}$ in formula (2) is 15 or more, and the total number of carbon atoms contained in $R^{11}$ to $R^{15}$ in formula (3) is 17 or more, and $X^-$ represents a monovalent anion).

[8] The method for producing an epoxy compound as described in any one of the [1] to [7] above, wherein in said production method, after the reaction, said substituent convertible to an active hydrogen-containing functional group or a salt thereof is hydrolyzed with a basic compound.

[9] The method for producing an epoxy compound as described in any one of the [1] to [8] above, wherein said compound having a carbon-carbon double bond is washed with an acidic aqueous solution and then subjected to the reaction.

[10] The method for producing an epoxy compound as described in any one of the [1] to [8] above, wherein said compound having a carbon-carbon double bond is washed with an aqueous chelating agent solution and then subjected to the reaction.

[11] The method for producing an epoxy compound as described in any one of the [1] to [10] above, wherein in said production method, a chelating agent is allowed to coexist in the reaction.

[12] A method for producing an epoxy resin by polymerizing an epoxy compound, the production method of an epoxy resin comprising: producing an epoxy compound by the method claimed in any one of the [1] to [11] above; and polymerizing the epoxy compound obtained above.

[13] A catalyst composition for an epoxidation reaction, comprising:

at least one of a tungsten compound and a molybdenum compound, and an onium salt having a carbon number of 20 or more and containing one or more substituents convertible to an active hydrogen-containing functional group or a salt thereof.

[14] The catalyst composition for an epoxidation reaction as described in the [13] above, wherein said active hydrogen-containing functional group is a hydroxyl group, a carboxyl group, an amino group, a mercapto group, a sulfonic acid group or a phosphoric acid group.

[15] The catalyst composition for an epoxidation reaction as described in the [13] or [14] above, which further comprises at least one of phosphoric acids and phosphonic acids (excluding an onium salt).

[16] The catalyst composition for an epoxidation reaction as described in any one of the [13] to [15] above, wherein said onium salt is an ammonium salt, a pyridinium salt, an imidazolinium salt or a phosphonium salt.

[17] The catalyst composition for an epoxidation reaction as described in any one of the [13] to [16] above, wherein said substituent convertible to an active hydrogen-containing functional group or a salt thereof is an alkoxycarbonyl group or an acyloxy group.

[18] The catalyst composition for an epoxidation reaction as described in any one of the [13] to [17] above, which further comprises a carboxylic acid (excluding an onium salt having a carboxy group).

[19] The catalyst composition for an epoxidation reaction as described in any one of the [13] to [18] above, wherein said onium salt is a compound represented by any one of the following formulae (1) to (3):

[Chem. 3]

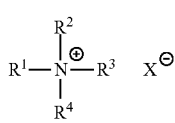
(1)

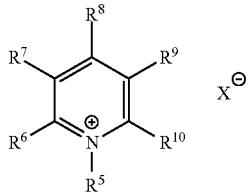
(2)

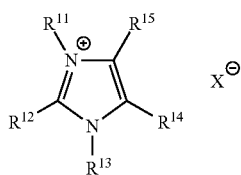
(3)

(in formulae (1) to (3), each of any one or more of $R^1$ to $R^4$, any one or more of $R^5$ to $R^{10}$ and any one or more of $R^{11}$ to $R^{15}$ independently represents —Y—CO—O—Z or —Y—O—CO—Z (wherein Y represents a direct bond or a divalent aliphatic hydrocarbon group having a carbon number of 1 to 25, in which a part of carbon atoms may be substituted with a heteroatom and which may have a substituent, and Z represents a monovalent aliphatic hydrocarbon group having a carbon number of 1 to 25, in which a part of carbon atoms may be substituted with a heteroatom, or a monovalent aromatic hydrocarbon group having a carbon number of 4 to 25, which may have a substituent), each of $R^1$ to $R^5$, $R^{11}$ and $R^{13}$, when these are not —Y—CO—O—Z or —Y—O—CO—Z, independently represents an alkyl group having a carbon number of 1 to 25, in which a part of carbon atoms may be substituted with a heteroatom and which may have a substituent, or a benzyl group, each of $R^6$ to $R^{10}$, $R^{12}$, $R^{14}$ and $R^{15}$, when these are not —Y—CO—O—Z or —Y—O—CO—Z, independently represents a hydrogen atom, a halogen atom, a cyano group, a nitro group, an alkyl group having a carbon number of 1 to 25, in which a part of carbon atoms may be substituted with a heteroatom and which may have a substituent, a phenyl group, a phenoxy group, a benzyl group, an N-alkylcarbamoyl group or an N-alkylsulfamoyl group, $R^1$ to $R^{15}$ may combine in the same compound to form a ring, provided that the total number of carbon atoms contained in $R^1$ to $R^4$ in formula (1) is 20 or more, the total number of carbon atoms contained in $R^5$ to $R^{16}$ in formula (2) is 15 or more, and the total number of carbon atoms contained in $R^{11}$ to $R^{15}$ in formula (3) is 17 or more, and $X^-$ represents a monovalent anion).

[20] An onium salt represented by the following formula (8) to (10), (12) or (31):

[Chem. 4]

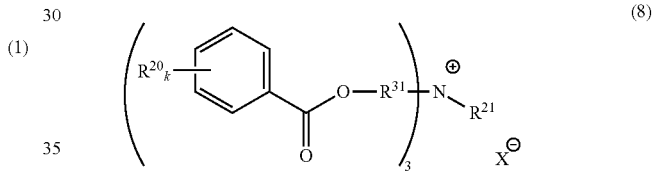
(8)

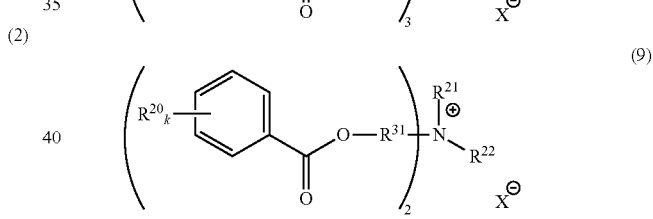
(9)

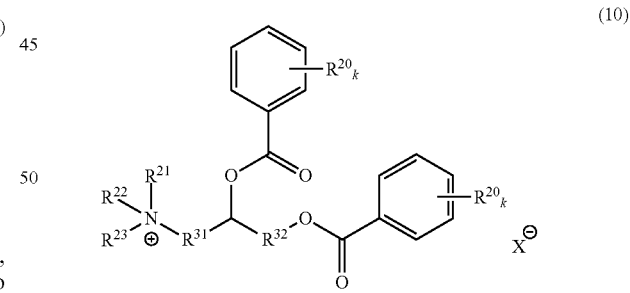
(10)

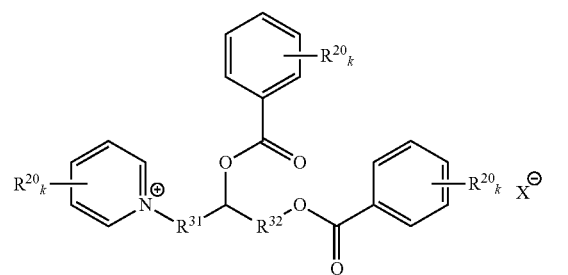
(12)

-continued

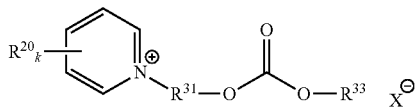
(31)

(in formulae (8) to (10), (12) and (31), $R^{20}$ represents a hydrogen atom, a halogen atom, a cyano group, a nitro group, an alkyl group having a carbon number of 1 to 25, in which a part of carbon atoms may be substituted with a heteroatom, a phenyl group, a phenoxy group, a benzyl group, an alkoxycarbonyl group, an N-alkylcarbamoyl group or an N-alkylsulfamoyl group; each of $R^{21}$ to $R^{23}$ independently represents an alkyl group having a carbon number of 1 to 25, in which a part of carbon atoms may be substituted with a heteroatom, or a benzyl group; $R^{20}$ to $R^{23}$ may combine in the same compound to form a ring; k represents an integer of 1 to 4;

each of $R^{31}$ and $R^{32}$ independently represents a divalent aliphatic hydrocarbon group having a carbon number of 1 to 25, in which a part of carbon atoms may be substituted with a heteroatom;

$R^{33}$ represents a monovalent aliphatic hydrocarbon group having a carbon number of 1 to 25, in which a part of carbon atoms may be substituted with a heteroatom, or a monovalent aromatic hydrocarbon group having a carbon number of 4 to 25, which may have a substituent;

provided that a plurality of k, $R^{20}$ or $R^{31}$ present in the same compound may be the same or different and the total number of carbon atoms contained in the cation moiety in the formulae is 20 or more; and $X^-$ represents a monovalent anion).

[21] A composition comprising:
an epoxy compound α represented by the following formula (32), and
a compound β having a structure where one or more glycidyl groups contained in said epoxy compound α are substituted with a 3-acyloxy-2-hydroxypropyl group (wherein said acyl group is a group represented by —CO—$R^{35}$ or —CO—Z):

[Chem. 5]

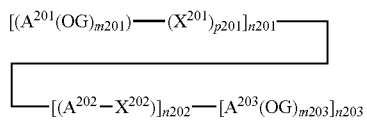
(32)

(in formula (32), G represents a glycidyl group (2,3-epoxypropanyl group), and said glycidyl group may be substituted with an alkyl group, a phenyl group or an alkoxycarbonyl group;

$A^{201}$ represents an (m201+1)-valent aromatic or aliphatic hydrocarbon group that may have a substituent, $A^{202}$ represents a divalent aromatic or aliphatic hydrocarbon group that may have a substituent, and $A^{203}$ represents an (m203+1)-valent aromatic or aliphatic hydrocarbon group that may have a substituent;

each of $X^{201}$ and $X^{202}$ independently represents a direct bond or a divalent linking group that may have a substituent;

p201 represents 0 or 1;

each of m201 and m203 independently represents an integer of 1 or more;

n201 represents an integer of 1 or more, n202 represents 0 or an integer of 1 or more, and n203 represents 0 or 1;

provided that in the case of n202=n203=0, when p201=0, $A^{201}$ becomes m201-valent and when p201=1, $X^{201}$ is a hydrogen atom or a monovalent group; and provided that a plurality of G, $A^{201}$, $A^{202}$, $X^{201}$, $X^{202}$, m201 or p201 contained in one molecule may be the same or different), wherein in —CO—$R^{35}$ and —CO—Z, Z represents a monovalent aliphatic hydrocarbon group having a carbon number of 1 to 25, in which a part of carbon atoms may be substituted with a heteroatom, or a monovalent aromatic hydrocarbon group having a carbon number of 4 to 25, which may have a substituent, and $R^{35}$ represents a group represented by any one of the following formulae (18) to (20):

[Chem. 6]

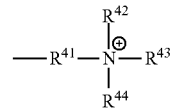
(18)

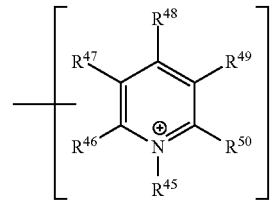
(19)

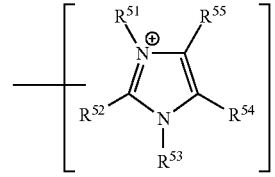
(20)

(in formula (18),
$R^{41}$ represents a direct bond or a divalent aliphatic hydrocarbon group having a carbon number of 1 to 25, in which a part of carbon atoms may be substituted with a heteroatom, and each of $R^{42}$ to $R^{44}$ independently represents an alkyl group having a carbon number of 1 to 25, in which a part of carbon atoms may be substituted with a heteroatom, or a benzyl group;

in formula (19),
any one of $R^{45}$ to $R^{50}$ represents a direct bond or a divalent aliphatic hydrocarbon group having a carbon number of 1 to 25, in which a part of carbon atoms may be substituted with a heteroatom, provided that in the case where $R^{45}$ is a direct bond or a divalent aliphatic hydrocarbon group having a carbon number of 1 to 25, in which a part of carbon atoms may be substituted with a heteroatom, each of $R^{46}$ to $R^{50}$ independently represents a hydrogen atom, a halogen atom, a cyano group, a nitro group, an alkyl group having a carbon number of 1 to 25, in which a part of carbon atoms may be substituted with a heteroatom, a phenyl group, a phenoxy group, an N-alkylcarbamoyl group or an N-alkylsulfamoyl group, and in the case where any one of $R^{46}$ to $R^{50}$ is a direct bond or a divalent aliphatic hydrocarbon group having a carbon number of 1 to 25, in which a part of carbon atoms may be substituted with a heteroatom, each of the other four independently represents a hydrogen atom, a halogen atom, a cyano group, a nitro group, an alkyl group having a carbon number of 1 to 25, in which a part of carbon atoms may be substituted with a heteroatom, a phenyl group, a phenoxy group, a benzyl group, an N-alkylcarbamoyl group or an N-alkylsulfamoyl group, and $R^{45}$ represents an alkyl group having a carbon number of 1 to 25, in which a part of carbon atoms may be substituted with a heteroatom, or a benzyl group; and in formula (20), any one of $R^{51}$ to $R^{55}$ represents a direct bond or a divalent aliphatic hydrocarbon group having a carbon number of 1 to 25, in which a part of carbon atoms may be substituted with a heteroatom, provided that in the case where either one of $R^{51}$ and $R^{53}$ is a direct bond or a divalent aliphatic hydrocarbon group having a carbon number of 1 to 25, in which a part of carbon atoms may be substituted with a heteroatom, the other represents an alkyl group having a carbon number of 1 to 25, in which a part of carbon atoms may be substituted with a heteroatom, or a benzyl group, and each of $R^{52}$, $R^{54}$ and $R^{55}$ independently represents a hydrogen atom, a halogen atom, a cyano group, a nitro group, an alkyl group having a carbon number of 1 to 25, in which a part of carbon atoms may be substituted with a heteroatom, a phenyl group, a phenoxy group, a benzyl group, an N-alkylcarbamoyl group or an N-alkylsulfamoyl group, and in the case where any one of $R^{52}$, $R^{54}$ and $R^{55}$ is a direct bond or a divalent aliphatic hydrocarbon group having a carbon number of 1 to 25, in which a part of carbon atoms may be substituted with a heteroatom, each of the other two independently represents a hydrogen atom, a halogen atom, a cyano group, a nitro group, an alkyl group having a carbon number of 1 to 25, in which a part of carbon atoms may be substituted with a heteroatom, a phenyl group, a phenoxy group, a benzyl group, an N-alkylcarbamoyl group or an N-alkylsulfamoyl group, and each of $R^{51}$ and $R^{53}$ independently represents an alkyl group having a carbon number of 1 to 25, in which a part of carbon atoms may be substituted with a heteroatom, or a benzyl group;

the total number of carbon atoms contained in $R^{41}$ to $R^{44}$ in formula (18) is 20 or more, the total number of carbon atoms contained in $R^{45}$ to $R^{50}$ in formula (19) is 15 or more, and the total number of carbon atoms contained in $R^{51}$ to $R^{55}$ in formula (20) is 17 or more; and $R^{41}$ to $R^{55}$ may combine in the same compound to form a ring).

[22] The composition as described in the [21] above, wherein said epoxy compound α is a compound represented by any one of the following formulae (13) to (15):

$$(A^1)\text{-}(OG)_{m1} \tag{13}$$

(in formula (13), G represents a glycidyl group (2,3-epoxypropanyl group), and said glycidyl group may be substituted with an alkyl group, a phenyl group or an alkoxycarbonyl group; $A^1$ represents an m1-valent aromatic or aliphatic hydrocarbon group that may have a substituent; and m1 represents an integer of 1 or more; provided that a plurality of G contained in one molecule may be same or different);

$$(GO)_{m2}\text{-}(A^{21})\text{-}[X^2\text{-}(A^{22})]_{n2}\text{—}X^2\text{-}(A^{21})\text{-}(OG)_{m2} \tag{14}$$

(in formula (14), G represents a glycidyl group, and said glycidyl group may be substituted with an alkyl group, a phenyl group or an alkoxycarbonyl group; $A^{21}$ represents an (m2+1)-valent aromatic or aliphatic hydrocarbon group that may have a substituent; $A^{22}$ represents a divalent aromatic or aliphatic hydrocarbon group that may have a substituent; the $A^{21}$ and $A^{22}$ connected through $X^2$ or a plurality of adjacent $A^{22}$ may combine with each other to form a ring; $X^2$ represents a direct bond or a divalent linking group that may have a substituent; m2 represents an integer of 1 or more; and n2 represents 0 or an integer of 1 or more; provided that a plurality of G, $A^{21}$, $A^{22}$, $X^2$ or m2 contained in one molecule may be same or different);

$$\text{H-}[(A^3(OG)_{m3})\text{-}X^3]_{n3}\text{-H} \tag{15}$$

(in formula (15), G represents a glycidyl group, and said glycidyl group may be substituted with an alkyl group, a phenyl group or an alkoxycarbonyl group; $A^3$ represents an (m3+2)-valent aromatic or aliphatic hydrocarbon group that may have a substituent; $X^3$ represents a direct bond, an alkylene group that may have a substituent, or —$R^{41}$-phenylene-$R^{42}$-, wherein each of $R^{41}$ and $R^{42}$ independently represents an alkylene group; m3 represents an integer of 1 or more; and n3 represents an integer of 2 or more; provided that a plurality of G, $A^3$, $X^3$ or m3 contained in one molecule may be same or different).

[23] The composition as described in the [21] or [22] above, wherein the abundance ratio of said compound β to said epoxy compound α contained in said composition is from 0.05 to 10.0 mol %.

[24] The composition as described in any one of the [21] to [23] above, wherein said compound β is a compound where in formula (13) to (15) or (32), one or more -OG groups are substituted with a group represented by the following formula (16) or (17) and one or more -OG groups may be substituted with a group represented by the following formula (33):

[Chem. 7]

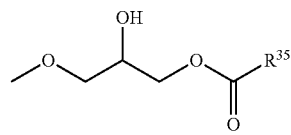

(16)

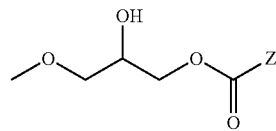

(17)

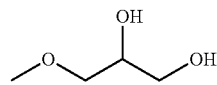

(33)

(in formula (16), $R^{35}$ represents a group represented by any one of the formulae (18) to (20) as described above; and in formula (17), Z represents a monovalent aliphatic hydrocarbon group having a carbon number of 1 to 25, in which a part of carbon atoms may be substituted with a heteroatom, or a monovalent aromatic hydrocarbon group having a carbon number of 4 to 25, which may have a substituent).

Advantage of the Invention

According to the present invention, an epoxy compound having a very small content of a heavy metal such as tungsten can be obtained. Also, a high-purity epoxy compound having very small onium salt and chlorine contents can be produced by a simple method without requiring a cumbersome process such as purification.

Furthermore, the production method of the present invention can be applied also to the production of an epoxy compound incapable of being purified by distillation or crystallization and has excellent general versatility. In the case where an epoxy compound obtained by the method of the present invention is used for an electronic material, an optical material, etc. or used as a medical/agrochemical raw material, problems attributable to impurities can be reduced, and a high-purity and high-quality product can be obtained.

In addition, even if a foreign material such as metal, activated carbon, silica gel and glass piece is mixed in the reaction system, decomposition, heat generation, oxygen generation and the like can be suppressed, and in turn, an epoxy compound can be safely produced despite use of hydrogen peroxide.

MODE FOR CARRYING OUT THE INVENTION

The mode for carrying out the present invention is described in detail below, but the constituent requirements described below are an example of the embodiment of the present invention, and the present invention is not limited to the following contents and can be implemented by making various modifications therein without departing from the gist of the present invention.

The production method of an epoxy compound of the present invention is characterized by reacting hydrogen peroxide with a compound having a carbon-carbon double bond (hereinafter, sometimes referred to as "olefin compound") in the presence of at least either a tungsten compound or a molybdenum compound and an onium salt having 20 or more carbon atoms and containing one or more substituents that are convertible to an active hydrogen-containing functional group or a salt thereof. In the description of the present invention, the "at least either a tungsten compound or a molybdenum compound" is sometimes referred to as "catalytic metal component"; the "onium salt having 20 or more carbon atoms and containing one or more substituents that are convertible to an active hydrogen-containing functional group or a salt thereof" is sometimes simply referred to as "onium salt"; the composition containing these "catalytic metal component" and "onium salt" is sometimes referred to as "catalyst composition for an epoxidation reaction" or simply as "catalyst composition"; and the composition obtained by oxidizing the catalyst composition above with hydrogen peroxide is sometimes referred to as "reaction active species composition".

In the present invention, hydrogen peroxide acts as an oxidant for oxidizing the catalyst composition.

As the hydrogen peroxide, aqueous hydrogen peroxide is usually used, and a commercially available aqueous hydrogen peroxide may be used directly or after dilution with water. The concentration of the aqueous hydrogen peroxide is usually 1 wt % or more, preferably 20 wt % or more, and usually 60 wt % or less, and considering the availability, safety problem, productivity and the like, is more preferably from 30 to 45 wt %.

The amount of the hydrogen peroxide used is usually 0.5 times by mol or more, preferably 1 times by mol or more, and usually 10 times by mol or less, preferably 3 times by mol or less, per mol of the double bond in the olefin compound used as a raw material.

<Catalyst Composition>

The catalyst composition of the present invention indicates a mixture of the later-described catalytic metal component and an onium salt. The method for preparing the catalyst composition may be appropriately selected according to the reactant or its reactivity and is not particularly limited, but either a method of mixing a catalytic metal component and an onium salt in the reaction system or a method of mixing a catalytic metal component and an onium salt outside the reaction system and using the mixture for the reaction may be employed. Also, the method for adding the later-described phosphoric acids may be either a mixing method in the reaction system or a previous mixing method outside the reaction system.

In the case of mixing a catalytic metal component and an onium salt in the reaction system, the mixing method and mixing order are not particularly limited, but specifically, the later-described catalytic metal component and an onium salt are usually added to a reaction system containing an olefin compound, whereby the composition can be prepared. The addition order thereof is not particularly limited, and either a catalytic metal component or an onium salt may be added first, or these may be added simultaneously.

Also, a catalytic metal component and an onium salt may be previously mixed outside the reaction system and then used. In this case, the mixing method, mixing order, and use mode of the mixture are not particularly limited, but a catalytic metal component and an onium salt may be mixed and used directly, or a composite of a catalyst component and an onium salt, which is produced in the catalyst composition, may be isolated and used. Among others, a method of mixing a catalytic metal component and an onium salt and using the mixture directly without performing isolation or activation is easy and therefore, preferable.

It is considered that in the reaction system, a catalytic metal component and an onium salt in the catalyst composition of the present invention form a composite, preferably further form a composite with at least either one of the later-described phosphoric acids and phosphonic acids, and this composite is oxidized with hydrogen peroxide and becomes a "reaction active species composition" to act as a reaction active species of the epoxidation reaction in the present invention.

Also, the reaction active species composition may be activated by partially adding hydrogen peroxide to the above-described mixture of a catalytic metal component and an onium salt (that is, the "catalyst composition") and then added to the reaction system.

<Catalytic Metal Component>

As the catalytic metal component of the present invention, at least either a tungsten compound or a molybdenum compound is used. Specifically, a tungstic acid or a salt of tungstic acid (hereinafter referred to as tungstic acids), a molybdic acid or a salt of molybdic acid (hereinafter referred to as molybdic acids), or a mixture thereof is used. Among these, tungstic acids are preferred in view of cost and availability.

The tungstic acids specifically include, for example, tungstic acid; a tungstate such as sodium tungstate, potassium tungstate, calcium tungstate and ammonium tungstate; a hydrate of the tungstate above; a phosphotungstic acid such as 12-tungstophosphoric acid and 18-tungstophosphoric acid; a silicotungstic acid such as 12-tungstosilicic acid; a 12-tungstoboric acid; and metallic tungsten. Among others, tungstic acid, a tungstate and a phosphotungstic acid are preferred, and in view of availability, tungstic acid, sodium tungstate, calcium tungstate and 12-tungstophosphoric acid are more preferred.

The molybdic acids include molybdic acid: a molybdate such as sodium molybdate, potassium molybdate and ammonium molybdate; and a hydrate of the molybdate above.

Among these tungstic acids and molybdic acids, tungstic acid, sodium tungstate and a hydrate thereof, and calcium tungstate and a hydrate thereof are preferred in view of availability, and tungstic acid is more preferred in view of ease of recovery and regeneration, tungstic acid is more preferred.

One of these catalytic metal components may be used alone, or two or more thereof may be used in appropriate combination.

The amount of the catalytic metal component used in the present invention can be appropriately adjusted according to the property of the substrate or the like employed and is not particularly limited but, in terms of the catalytic metal atom (for example, in the case of tungstic acids, in terms of tungsten atom), is usually 0.001 mol or more, preferably 0.005 mol or more, more preferably 0.01 mol or more, and usually 1.0 mol or less, preferably 0.50 mol or less, more preferably 0.10 mol or less, per mol of the double bond contained in the olefin compound used as a raw material. If the amount used is less than this lower limit, the reaction may not proceed, whereas if the amount used exceeds the upper limit above, this may be disadvantageous in view of cost.

<Onium Salt>

The onium salt used in the present invention is an onium salt having 20 or more carbon atoms and containing one or more substituents that are convertible to an active hydrogen-containing functional group or a salt thereof.

This onium salt has properties of being oil-soluble at the time of epoxidation reaction, soluble in a reaction solvent, distributed in the organic phase side when the system is separated into an aqueous phase and an organic phase, and stable under epoxidation reaction conditions or kept from extreme reduction in the catalytic ability even when the structure is changed during the epoxidation reaction. In order to be soluble in a reaction solvent and distributed in the organic phase, high lipophilicity is required and for this purpose, the onium salt must contain 20 or more carbon atoms.

Also, the onium salt is characterized by containing a substituent capable of, after the completion of epoxidation reaction, affording conversion to a water-soluble compound having an active hydrogen-containing functional group or a salt by a simple method under mild conditions causing no decomposition of the epoxy group of an epoxy compound produced by the reaction.

The cation species (hereinafter, simply referred to as "onium") of the onium salt for use in the present invention is not particularly limited as long as it satisfies the above-described conditions. That is, the onium is an onium having 20 or more carbon atoms and containing one or more substituents that are convertible to an active hydrogen-containing functional group or a salt thereof, and specific oniums include usually ammonium, a nitrogen-containing heterocyclic quaternary cation such pyridinium and imidazolinium, phosphonium, etc. (in other words, the onium salt includes an ammonium salt, a pyridinium salt, an imidazolinium salt, and a phosphonium salt). Because of ease of synthesis, ammonium, pyridinium or imidazolinium is preferably used.

The anion species of the onium salt for use in the present invention is not particularly limited but is a monovalent anion and specifically includes a hydrogen sulfate ion, a monomethyl sulfate ion, a halide ion, a nitrate ion, an acetate ion, a hydrogen carbonate ion, a dihydrogen phosphate ion, a sulfonate ion, a carboxylate ion, a hydroxide ion, etc. From the standpoint that the anion species does not attach to the epoxy group of an epoxy compound as a reaction product or to the carbon-carbon double bond of an olefin compound as a raw material compound or the preparation is easy, the anion is preferably a monomethyl sulfate ion, a hydrogen sulfate ion, an acetate ion, a dihydrogen phosphate ion or a hydroxide ion, The onium salt for use in the present invention contains, in its onium moiety, one or more substituents that are convertible to an active hydrogen-containing functional group or a salt thereof. The active hydrogen-containing functional indicates a functional group capable of dissociating to release a hydrogen ion, and the salt thereof indicates a compound where another cation species becomes a counter anion instead of the dissociated hydrogen ion. The active hydrogen-containing functional group is not particularly limited and is preferably a hydroxyl group, a carboxyl group, an amino group, a mercapto group, a sulfonic acid group, a phosphoric acid group, or a salt thereof, more preferably a carboxyl group or a hydroxyl group, still more preferably a hydroxyl group.

The substituent convertible to an active hydrogen-containing functional group or a salt thereof means a substituent that can be converted to the above-described active hydrogen-containing functional group or a salt thereof by applying at least either a physical operation or a chemical operation. Specifically, the substituent indicates a substituent that can be converted by a reaction with a base, a reaction with an acid, a chemical reaction such as catalytic hydrogenation, heating, a photoreaction, an enzyme reaction, microwave irradiation, etc. The substituent is preferably a substituent convertible under mild conditions, more preferably a substituent convertible under the conditions not involving a reaction with the epoxy group, still more preferably, for example, an alkoxycarbonyl group, an acyloxy group, a carbamate group, an imide group, an amide group, an ether group, a silyl ether group, an acetal group, a ketal group, a hemiacetal group, a sulfonic acid ester group, a thioether group, a thioester group, a thiocarbamate group, a thioacetal group, a phosphoric acid ester group, or a benzyl ether group.

In addition, a substituent having a structure where in the process of the onium salt-containing reaction active species composition reacting with an olefin compound, an active hydrogen-containing functional group or a salt thereof is produced from the above-described substituent convertible to an active hydrogen-containing functional group or a salt thereof, for example, a ketone group (ketone structure) that are converted to an ester group by a Baeyer-Villiger oxidation reaction during the reaction above, a nitrile group and a benzyl group, is also encompassed, as an example, by the substituent convertible to an active hydrogen-containing functional group or a salt thereof.

Among others, an alkoxy carbonyl group and an acyl group are preferred, because these can be hydrolyzed simply by the contact with a basic aqueous solution without decomposing the epoxy group and converted to a hydroxyl group, a carboxylic acid group or a salt thereof and their synthesis is also easy. An alkoxycarbonyl is more preferred.

The number of the above-described substituents is 1 or more but from the standpoint of removal efficiency in the washing, is preferably 2 or more.

The onium salt-containing reaction active species composition for use in the present invention is preferably dissolved in at least either an olefin compound as a reaction raw material or a solvent used at the time of epoxidation reaction. Therefore, the onium salt must have a highly lipophilic moiety in its structure. The specific structure or form is not particularly limited as long as it does not inhibit the reaction and is stable to the epoxidation reaction or maintains the catalytic activity even when the structure is changed during the epoxidation reaction. The structure may be any of an aliphatic group, an aromatic group and a compound having both groups, and the form may also be any of linear, branched and cyclic structures. Furthermore, the structure may contain, as a constituent atom, a heteroatom such as oxygen and nitrogen. It may be sufficient if both a compound produced by the after-treatment, that is, a compound having a substituent convertible to an active hydrogen-containing functional group, and a compound composed of other moieties can be removed under the conditions not involving decomposition of the epoxy group.

As the onium salt for use in the present invention, an onium salt represented by any one of the following formulae (1) to (3) is preferably used:

[Chem. 8]

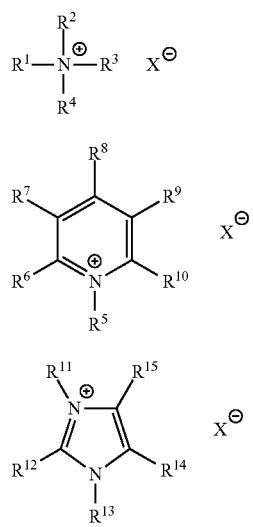

(in formulae (1) to (3), each of any one or more of $R^1$ to $R^4$, any one or more of $R^5$ to $R^{10}$ and any one or more of $R^{11}$ to $R^{15}$ independently represents —Y—CO—O—Z or —Y—O—CO—Z (wherein Y represents a direct bond or a divalent aliphatic hydrocarbon group having a carbon number of 1 to 25, in which a part of carbon atoms may be substituted with a heteroatom and which may have a substituent, and Z represents a monovalent aliphatic hydrocarbon group having a carbon number of 1 to 25, in which a part of carbon atoms may be substituted with a heteroatom, or a monovalent aromatic hydrocarbon group having a carbon number of 4 to 25, which may have a substituent), each of $R^1$ to $R^5$, $R^{11}$ and $R^{13}$, when these members are not —Y—CO—O—Z or —Y—O—CO—Z, independently represents an alkyl group having a carbon number of 1 to 25, in which a part of carbon atoms may be substituted with a heteroatom and which may have a substituent, or a benzyl group, each of $R^6$ to $R^{10}$, $R^{12}$, $R_{14}$ and $R^{15}$, when these members are not —Y—CO—O—Z or —Y—O—CO—Z, independently represents a hydrogen atom, a halogen atom, a cyano group, a nitro group, an alkyl group having a carbon number of 1 to 25, in which a part of carbon atoms may be substituted with a heteroatom and which may have a substituent, a phenyl group, a phenoxy group, a benzyl group, an N-alkylcarbamoyl group or an N-alkylsulfamoyl group, $R^1$ to $R^{15}$ may combine in the same compound to form a ring, or when $R^1$ to $R^{15}$ are an alkyl group having a carbon number of 1 to 25, in which a part of carbon atoms may be substituted with a heteroatom and which may have a substituent, each of these members may have, as the substituent, another onium salt represented by any one of formulae (1) to (3), provided that the total number of carbon atoms contained in $R^1$ to $R^4$ in formula (1) is 20 or more, the total number of carbon atoms contained in $R^5$ to $R^{10}$ in formula (2) is 15 or more, and the total number of carbon atoms contained in $R^{11}$ to $R^{15}$ in formula (3) is 17 or more, and $X^-$ represents a monovalent anion).

In formula (1), any one or more of $R^1$ to $R^4$ represents —Y—CO—O—Z or —Y—O—CO—Z. Also, the total number of carbon atoms contained in R' to $R^4$ is 20 or more.

Similarly to formula (1), any one or more of $R^5$ to $R^{10}$ in formula (2) represents —Y—CO—O—Z or —Y—O—CO—Z. Also, the total number of carbon atoms contained in $R^5$ to $R^{10}$ is 15 or more.

Similarly, any one or more of $R^{11}$ to $R^{15}$ in formula (3) represents —Y—CO—O—Z or —Y—O—CO—Z. Also, the total number of carbon atoms contained in $R^{11}$ to $R^{15}$ is 17 or more.

Y represents a direct bond or a divalent aliphatic hydrocarbon group having a carbon number of 1 to 25, in which a part of carbon atoms may be substituted with a heteroatom and which may have a substituent, and the aliphatic hydrocarbon group may have any of linear, branched and cyclic structures.

The divalent aliphatic hydrocarbon group specifically includes a linear aliphatic hydrocarbon group such as methylene, ethylene, tetramethylene and hexamethylene, a branched aliphatic hydrocarbon group formed by further bonding an alkyl chain to the hydrocarbon group above, and a cyclic aliphatic hydrocarbon group such as cyclohexene. In the case where Y is a divalent aliphatic hydrocarbon group having a carbon number of 1 to 25, a part of carbon atoms thereof may be substituted with a heteroatom. Specifically, the methylene group in the structure of such a divalent aliphatic hydrocarbon group may be substituted with a heteroatom-containing structure such as —O—, —S—, —SO—, —SO$_2$—, —NH—, —NR$^{16-}$ (R$^{16}$ represents a monovalent aliphatic hydrocarbon group having a carbon number of 1 to 25 or a monovalent aromatic hydrocarbon group), —CONR$^{17}$— (R$^{17}$ represents a hydrogen atom, a monovalent aliphatic hydrocarbon group having a carbon number of 1 to 25 or a monovalent aromatic hydrocarbon group), —NHCONH—, —CONHCO— and —SO$_2$NR$^{17}$— (R$^{17}$ has the same meaning as above). Incidentally, the "hydrocarbon group in which a part of the carbon atoms may be substituted with a heteroatom" as used in the description of the present invention always has the same meaning as above. Y is preferably ethylene, propylene, tetramethylene, hexamethylene or —$CH_2CH_2$—O—$CH_2CH_2$—.

In the case where Y is a divalent aliphatic hydrocarbon group having a carbon number of 1 to 25, in which a part of carbon atoms may be substituted with a heteroatom and which may have a substituent, the substituent includes, for example, —O—CO—Z and —CO—O—Z (wherein Z has the same meaning as in formulae (1) to (3). In this case, each of the compounds represented by formula (1) to (3), where any one of $R^1$ to $R^{15}$ is —Y—CO—O—Z or —Y—O—CO—Z, has —O—CO—Z or —CO—O—Z and additionally has —O—CO—Z or —CO—O—Z as the substituent of the aliphatic hydrocarbon group in Y.

Z represents a monovalent aliphatic hydrocarbon group having a carbon number of 1 to 25, in which a part of carbon atoms may be substituted with a heteroatom, or a monovalent aromatic hydrocarbon group having a carbon number of 4 to 25. The monovalent aliphatic hydrocarbon group having a carbon number of 1 to 25 may have any of linear, branched and cyclic structures. This aliphatic hydrocarbon group specifically includes a linear aliphatic hydrocarbon group such as methyl, ethyl, propyl, butyl, hexyl butyl and octyl, a branched aliphatic hydrocarbon formed by further bonding an alkyl chain to the hydrocarbon group above, and a cyclic aliphatic hydrocarbon group such as cyclohexyl. The monovalent aromatic hydrocarbon group having a carbon number of 4 to 25 includes, for example, a monovalent benzene ring that may have an alkyl group or a halogen atom as a substituent, and a naphthalene ring.

In the case of a monovalent aliphatic hydrocarbon group having a carbon number of 1 to 25, a part of carbon atoms in the structure thereof may be substituted with a heteroatom. Specifically, the methylene group in the structure of the aliphatic hydrocarbon group may be substituted with a heteroatom-containing structure such as —$NR^{16}$— ($R^{16}$—O—, —S—, —SO—, —$SO_2$—, —NH—, represents a monovalent aliphatic hydrocarbon group having a carbon number of 1 to 25 or a monovalent aromatic hydrocarbon group), —$CONR^{17}$— ($R^{17}$ represents a hydrogen atom, a monovalent aliphatic hydrocarbon group having a carbon number of 1 to 25 or a monovalent aromatic hydrocarbon group), —NHCONH—, —CONHCO— and —$SO_2NR^{17}$— ($R^{17}$ has the same meaning as above).

The monovalent aromatic hydrocarbon group having a carbon number of 4 to 25 includes, for example, a phenyl group, a benzyl group, and a naphthyl group, and these groups may have a substituent including, for example, a halogen atom, a cyano group, a nitro group, an alkyl group having a carbon number of 1 to 25, in which a part of carbon atoms may be substituted with a heteroatom, a phenyl group, a phenoxy group, a benzyl group, an alkoxycarbonyl group, an N-alkylcarbamoyl group and an N-alkylsulfamoyl group. Among these, in view of productivity of the onium salt, a phenyl group is preferred.

In the case where Y of —Y—CO—O—Z in the formulae above represents a hydrocarbon group, the carbon number thereof is preferably 3 or more in view of stability of the onium salt during the epoxidation reaction.

The onium salts where $R^1$ to $R^{15}$ are not —Y—CO—O—Z or —Y—O—CO—Z are described below.

Out of $R^1$ to $R^{15}$, each of $R^1$ to $R^5$, $R^{11}$ and $R^{13}$, when these members are not —Y—CO—O—Z or —Y—O—CO—Z, independently represents an alkyl group having a carbon number of 1 to 25, in which a part of carbon atoms may be substituted with a heteroatom and which may have a substituent, or a benzyl group.

Each of $R^6$ to $R^{10}$, $R^{12}$, $R^{14}$ and $R^{15}$, when these members are not —Y—CO—O—Z or —Y—O—CO—Z, independently represents a hydrogen atom, a halogen atom, a cyano group, a nitro group, an alkyl group having a carbon number of 1 to 25, in which a part of carbon atoms may be substituted with a heteroatom and which may have a substituent, a phenyl group, a phenoxy group, an N-alkylcarbamoyl group or an N-alkylsulfamoyl group.

$R^1$ to $R^{15}$ may combine in the same compound to form a ring.

In the case where $R^1$ to $R^{15}$ are an alkyl group having a carbon number of 1 to 25, in which a part of carbon atoms may be substituted with a heteroatom and which may have a substituent, each of these members may have, as the substituent, another onium salt represented by any one of formulae (1) to (3). That is, the onium salt may be a compound where a plurality of compounds represented by any one of formulae (1) to (3) are connected through $R^1$ to $R^{15}$. At this time, the structures of the plurality of onium salts may be the same or different. This compound specifically includes a 1,2-ethanediaminium salt, a 4,4'-bipyridinium salt, etc.

In the case where each of $R^1$ to $R^{15}$ is an alkyl group having a carbon number of 1 to 25, a part of carbon atoms in the structure thereof may be substituted with a heteroatom. Specifically, the methylene group may be substituted with a heteroatom-containing structure such as —O—, —S—, —SO—, —$SO_2$—, —NH—, —$NR^{16}$— ($R^{16}$ represents a monovalent aliphatic hydrocarbon group having a carbon number of 1 to 25 or a monovalent aromatic hydrocarbon group), —$CONR^{17}$— ($R^{17}$ represents a hydrogen atom, a monovalent aliphatic hydrocarbon group having a carbon number of 1 to 25 or a monovalent aromatic hydrocarbon group), —NHCONH—, —CONHCO— and —$SO_2NR^{17}$— ($R^{17}$ has the same meaning as above).

Among others, each of $R^1$ of $R^5$, $R^{11}$ and $R^{13}$ is preferably a methyl group, an ethyl group, a propyl group, an isopropyl group, a tert-butyl group, an octyl group, an octadecyl group or a benzyl group, more preferably a methyl group or an ethyl group.

Each of $R^6$ o $R^{10}$, $R^{12}$, $R^{14}$ and $R^{15}$ is preferably a hydrogen atom, a chlorine atom, a methyl group, an ethyl group, a propyl group, an isopropyl group, a tert-butyl group, an octyl group, an octadecyl group, a halogen atom or a phenyl group, more preferably a hydrogen atom, a tert-butyl group or a phenyl group.

$X^-$ represents an anion species of the onium salt and is a monovalent anion. The anion species is specifically a hydrogen sulfate ion, a monomethyl sulfate ion, a halide ion, a nitrate ion, an acetate ion, a hydrogen carbonate ion, a dihydrogen phosphate ion, a sulfonate ion, a carboxylate ion or a hydroxide ion, and from the standpoint that the anion does not attach to the epoxy group or the carbon-carbon double bond or the preparation is easy, a monomethyl sulfate ion, a hydrogen sulfate ion, a chloride ion, an acetate ion, a dihydrogen phosphate ion or a hydroxide ion is preferred.

Out of the compounds represented by formula (1), specific compounds that can be suitably used as the onium salt of the present invention include the compounds represented by the following formulae (8) to (11), (34) and (35). Here, the compounds represented by the following formulae (8) to (10) are novel compounds suitable as the onium salt of the present invention.

These compounds are preferable in that the compound has a plurality of ester structures in the molecule and not only can be converted to a water-soluble compound after hydrolysis but also can be easily synthesized from an easily available raw material, and among others, (8) to (11) are preferred in view of ease of instrumental analysis such as high-performance liquid chromatograph and ease of production control.

[Chem. 9]

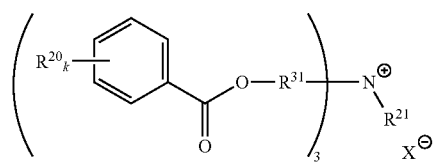
(8)

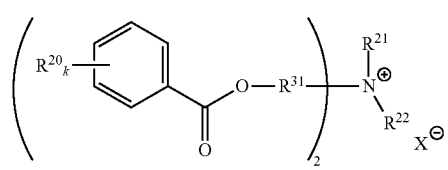
(9)

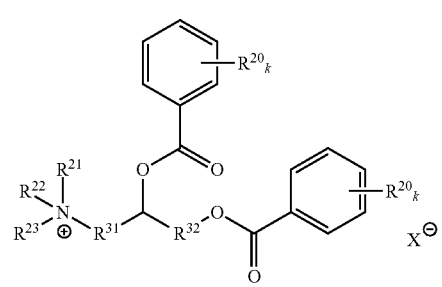
(10)

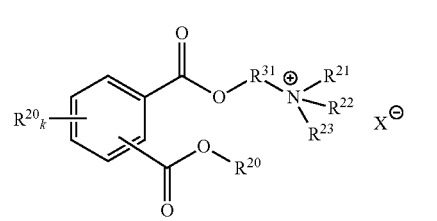
(11)

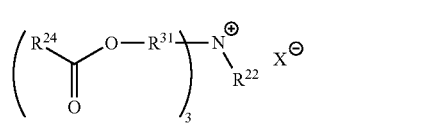
(34)

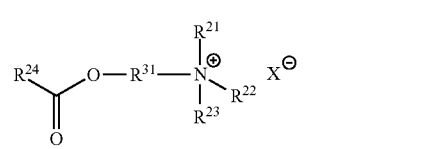
(35)

(in formulae (8) to (11), (34) and (35), $R^{20}$ represents a hydrogen atom, a halogen atom, a cyano group, a nitro group, an alkyl group having a carbon number of 1 to 25, in which a part of carbon atoms may be substituted with a heteroatom, a phenyl group, a phenoxy group, a benzyl group, an alkoxycarbonyl group, an N-alkylcarbamoyl group or an N-alkylsulfamoyl group; each of $R^{21}$ to $R^{23}$ independently represents an alkyl group having a carbon number of 1 to 25, in which a part of carbon atoms may be substituted with a heteroatom, or a benzyl group; $R^{24}$ represents an alkyl group having a carbon number of 1 to 25, in which a part of carbon atoms may be substituted with a heteroatom; $R^{20}$ to $R^{24}$ may combine in the same compound to form a ring; k represents an integer of 1 to 4;

each of $R^{31}$ and $R^{32}$ independently represents a divalent aliphatic hydrocarbon group having a carbon number of 1 to 25, in which a part of carbon atoms may be substituted with a heteroatom;

provided that a plurality of k, $R^{20}$ or $R^{31}$ present in the same compound may be the same or different and the total number of carbon atoms contained in the cation moiety in the formula is 20 or more; and $X^-$ represents a monovalent anion).

As to the compound represented by formula (2), specific compounds that can be suitably used as the onium salt of the present invention include the compounds represented by the following formulae (12) and (31). Here, the compounds represented by the following formulae (12) and (31) are novel compounds suitable as the onium salt of the present invention.

[Chem. 10]

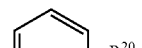
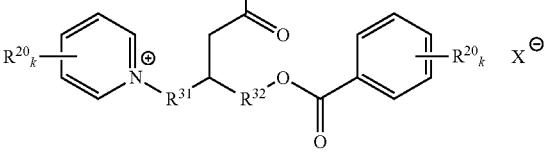
(12)

(in formula (12), $R^{20}$ represents a hydrogen atom, a halogen atom, a cyano group, a nitro group, an alkyl group having a carbon number of 1 to 25, in which a part of carbon atoms may be substituted with a heteroatom, a phenyl group, a phenoxy group, a benzyl group, an alkoxycarbonyl group, an N-alkylcarbamoyl group or an N-alkylsulfamoyl group; $R^{20}$ may combine in the same compound to form a ring; k represents an integer of 1 to 4; provided that a plurality of k or $R^{20}$ present in the same compound may be the same or different;

each of $R^{31}$ and $R^{32}$ independently represents a divalent aliphatic hydrocarbon group having a carbon number of 1 to 25, in which a part of carbon atoms may be substituted with a heteroatom; the total number of carbon atoms contained in the cation moiety in the formula is 20 or more; and $X^-$ represents a monovalent anion).

[Chem. 11]

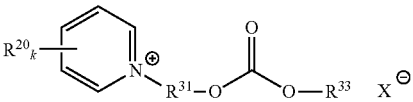
(31)

(in formula (31), $R^{20}$ represents a hydrogen atom, a halogen atom, a cyano group, a nitro group, an alkyl group having a carbon number of 1 to 25, in which a part of carbon atoms may be substituted with a heteroatom, a phenyl group, a phenoxy group, a benzyl group, an alkoxycarbonyl group, an N-alkylcarbamoyl group or an N-alkylsulfamoyl group and may combine in the same compound to form a ring; k represents an integer of 1 to 4; provided that a plurality of $R^{20}$ present in the same compound may be the same or different;

$R^{31}$ represents a divalent aliphatic hydrocarbon group having a carbon number of 1 to 25, in which a part of carbon atoms may be substituted with a heteroatom;

$R^{33}$ represents a monovalent aliphatic hydrocarbon group having a carbon number of 1 to 25, in which a part of carbon atoms may be substituted with a heteroatom, or a monovalent aromatic hydrocarbon group having a carbon number of 4 to 25, which may have a substituent;

the total number of carbon atoms contained in the cation moiety in the formula is 20 or more; and $X^-$ represents a monovalent anion).

In formulae (8) to (12), (31), (34) and (35), $R^{20}$ is preferably a hydrogen atom or an alkyl group having a carbon number of 1 to 4; each of $R^{21}$ to $R^{23}$ is preferably an alkyl group having a carbon number of 1 to 18, more preferably an alkyl group having a carbon number of 1 to 8; $R^{24}$ is preferably an alkyl group having a carbon number of 1 to 8; each of $R^{31}$ and $R^{32}$ is independently preferably an alkylene group having a carbon number of 1 to 11, more preferably an alkylene group having a carbon number of 1 to 5, still more preferably an ethylene group or an ethylene group substituted with a propane-1,2-diyl group; $R^{31}$ and $R^{32}$ may combine to form a cyclic structure such as pyranose ring; $R^{33}$ is preferably an alkyl group having a carbon number of 1 to 16; k is preferably 1; and $X^-$ is preferably a monomethyl sulfate ion, a hydrogen sulfate ion, a dihydrogen phosphate ion or a chlorine ion.

One of the onium salts may be used alone, or two or more thereof may be used in appropriate combination.

The use amount of the onium salt based on the catalytic metal component may be appropriately adjusted according the properties of the substrate or the like used and is not particularly limited but is usually from 0.1 to 10 times by mol, preferably from 0.3 to 5.0 times by mol, more preferably from 0.2 to 2.0 times by mol, per one atom of the catalytic metal component used.

<Synthesis Method of Onium Salt>

The above-described onium salts can be synthesized by alkylating the respective corresponding tertiary amines, pyridines, imidazoles, etc. The reagent employed for the alkylation is not particularly limited, but $R^{18}$-A (wherein A represents a halogen atom such as chlorine, bromine and iodine, an aromatic sulfonyl such as p-toluenesulfonyl and methanesulfonyl, an aliphatic sulfonyl, a sulfuric acid ester, a carbonic acid ester or an oxylanyl group, and $R^{18}$ represents $R^1$ to $R^4$, $R^5$, $R^{11}$ or $R^{13}$ in formulae (1) to (3) or a substituent convertible to $R^1$ to $R^4$, $R^5$, $R^{11}$ or $R^{13}$) is used.

Specific examples of $R^{18}$-A include an alkyl halide compound such as methyl iodide, ethyl iodide, ethyl bromide, octyl chloride and cetyl chloride; a sulfonyl compound such as methanesulfonic acid octyl ester and p-toluenesulfonic acid benzyl ester; a sulfonic acid ester such as dimethyl sulfate and diethyl sulfate; a carbonic acid ester such as dimethyl carbonate and diethyl carbonate; and an oxylanyl compound such as glycidol and epichlorohydrin.

The alkylation reaction may also use a base. Specific examples of the base used include an inorganic base such as potassium carbonate, sodium carbonate, cesium carbonate, sodium hydrogen carbonate, potassium hydrogen carbonate, sodium hydroxide and potassium hydroxide; and an organic base such as ammonia, methylamine and ethylamine. Among these, potassium carbonate, sodium carbonate, sodium hydrogen carbonate, potassium hydrogen carbonate and potassium sulfate are preferred, and potassium carbonate is more preferred.

The alkylation reaction may also use an organic solvent. The solvent used for the reaction may be removed by distillation after the reaction or after the later-described post-reaction treatment, or the solution after the post treatment may be subjected as it is to the epoxidation reaction. Specific examples of the organic solvent used include esters such as ethyl acetate, aliphatic hydrocarbons such as heptane, hexane and cyclohexane, aromatic hydrocarbons such as benzene, toluene, xylene and pyridine, aprotic solvents such as acetonitrile, tetrahydrofuran, dioxane and 1,2-dimethoxyethane, ketones such as acetone and methyl ethyl ketone, aprotic polar solvents such as N,N'-dimethylformamide, N-methylpyrrolidone and dimethyl sulfoxide, an halogen-containing solvents such as chloroform, dichloromethane, 1,2-dichloroethane and chlorobenzene. Among these, toluene, hexane and heptane are preferred, and toluene is more preferred.

After the completion of alkylation reaction, inorganic materials produced by the reaction may be appropriately removed by an appropriate such as filtration and washing.

In the case of performing the alkylation by using $R^{18}$-A, the onium produced often forms a salt having $A^-$ as the counter ion. Also, in the case of performing a washing operation, the onium often form a salt with a hydroxide ion in water or an ion in the cleaning water. Such a counter ion can be converted to a desired counter ion by an operation such as washing or ion exchange resin treatment. For example, in the case of performing methylation by using dimethyl sulfate, a monomethyl sulfate salt is formed, but this salt can be formed into hydrogen sulfate salt by the washing with aqueous sulfuric acid.

The method for introducing the substituent —Y—CO—O—Z or —Y—O—CO—Z (Y and Z have the same meanings as above) into the onium salt includes, for example, the following methods:

1) a method of reacting A-Y—CO—O—Z or A-Y—O—CO—Z (A has the same meaning as above) with the above-described tertiary amines, pyridines or imidazoles as a raw material of the onium salt and thereby introducing the ester group;

2) a method of esterifying amines, pyridines or imidazoles each having —Y—CO₂H to form —Y—CO—O—Z and alkylating the ester as above to give an onium salt;

a method of esterifying amines, pyridines or imidazoles each having —Y—OH to form —Y—O—CO—Z and alkylating the ester as above to give an onium salt; or a method of subjecting amines, pyridines or imidazoles each having —Y—CO—O—$R^{19}$ ($R^{19}$ represents an alkyl group having a carbon number of 1 to 12) to a transesterification reaction to form —Y—CO—O—Z and alkylating the ester as above to give an onium salt;

3) a method of esterifying an onium salt containing —Y—CO₂H to form —Y—CO—O—Z;

a method of esterifying an onium salt containing —Y—OH to form —Y—O—CO—Z; or a method of subjecting an onium salt containing —Y—CO—O—$R^{19}$ to a transesterification reaction to form —Y—CO—O—Z; and 4) a method of alkylating amines, pyridines or imidazoles each having —Y—CO—O—Z or —Y—O—CO—Z to give an onium salt; or a method using, as a raw material, an ammonium salt, a pyridinium salt or imidazolinium salt each having —Y—CO—O—Z or —Y—O—CO—Z.

Of these, the method for esterification to —Y—CO—O—H in 2) and 3) includes a method of effecting the halogenation to form —Y—CO—O-T (T represents a halogen atom) and then reacting with a corresponding alcohol Z—OH, a method of dehydrating and condensing Z—OH in the presence of an acid catalyst or by using a condensing agent such as DDC and CDI, and a method of subjecting —Y—CO—O—$R^{19}$ to a transesterification reaction. The methods of effecting the dehydration/condensation and transesterification include a method of reacting a corresponding alcohol Z—OH in the presence of an acid catalyst. On this occasion, it is preferable to perform the transesterification reaction while removing the produced water or $R^{19}$—OH by distillation, adsorption or other methods.

The method of esterifying —Y—OH includes a method of reacting the alcohol with a corresponding acid chloride Z—CO-T (T represents a halogen atom), and a method of dehydrating and condensing Z—CO—O—H in the presence of an acid catalyst or by using a condensing agent such as DCC and CDI. The method of subjecting —Y—CO—O—$R^{19}$ to a transesterification reaction includes a method of reacting a corresponding alcohol Z—OH in the presence of an acid catalyst. On this occasion, it is preferable to perform the transesterification reaction while removing the produced water or $R^{19}$—OH by distillation, adsorption or other methods. Among these methods, in view of the cost, a method of introducing the ester group by performing dehydration/condensation or transesterification in the presence of an acid catalyst is preferred in industry.

Examples of the synthesis method 3) for an onium salt include a method where a commercially available surfactant having a long-chain alkyl-di(hydroxyethyl)ammonium salt structure is esterified to give an onium salt.

At this time, as the acid catalyst used, for example, a mineral acid such as sulfuric acid, nitric acid and hydrochloric acid; an organic acid such as benzenesulfonic acid, p-toluenesulfonic acid, methanesulfonic acid, ethanesulfonic acid, trifluoromethanesulfonic acid, trichloromethanesulfonic acid, trifluoroacetic acid, trichloroacetic acid and acetic acid; a tungstic acid, a molybdic acid or a heteropolyphosphoric acid thereof, such as $H_3PW_{12}O_{40}$, $H_4SiW_{12}O_{40}$, $H_4TiW_{12}O_{40}$, $H_5CoW_{12}O_{40}$, $H_5FeW_{12}O_{40}$, $H_6P_2W_{18}O_{62}$, $H_7PW_{11}O_{33}$, $H_4TiMo_{12}O_{40}$, $H_3PMo_{12}O_{40}$, $H_7PMo_{11}O_{39}$, $H_6P_2Mo_{18}O_{62}$, $H_4PMoW_{11}O_{40}$, $H_4PVMo_{11}O_{40}$, $H_4SiMo_{12}O_{40}$, $H_5PV_2Mo_{10}O_{40}$, $H_3PMo_6W_6O_{40}$, $H_{0.5}Cs_{2.5}PW_{12}O_{40}$ and hydrates thereof; a cation-exchange resin such as Amberlyst IR120; and an H-type zeolite such as H—ZSM-5 can be used. Among these, sulfuric acid is preferred in view of the cost, but in the case where a sulfate is precipitated to reduce the reactivity, it is preferably to use an organic acid such as p-toluenesulfonic acid and methanesulfonic acid, if desired. As for the use amount of such a catalyst, the catalyst may be used in an amount of 0.1 to 100 wt %, preferably from 1 to 20 wt %, based on the substrate.

Although not limited in particular, the solvent used is not especially limited as long as it does not participate in the reaction, and includes aromatic hydrocarbons such as benzene, toluene and xylene, and aliphatic hydrocarbons such as hexane, heptane, octane and dodecane.

The amount of the solvent used is not particularly limited but if a salt of the substrate and the acid catalyst is precipitated from the system, the reaction rate may decrease. Therefore, it is preferable to appropriately adjust the amount according to the properties of the substrate or acid.

The onium salt obtained through the above-described process may be once isolated, purified and then used for the epoxidation reaction or may be used without isolation and purification but is preferably used for the epoxidation reaction without isolation and purification, because this is advantageous in view of production efficiency and also the onium salt can be used for the reaction by suppressing its decomposition. In the case where the "active hydrogen-containing functional group" is an alkoxycarbonyl group or an acyloxy group, the composition may contain a carboxylic acid or an alcohol, which is a decomposition product of the onium salt.

<Phosphoric Acids and Phosphonic Acids>

The catalyst composition of the present invention may contain, and in view of reactivity, preferably contains, at least either phosphoric acids and phosphonic acids (excluding an onium salt). At least either phosphoric acids or phosphonic acids may be sufficient if it is present together with the catalytic metal component and the onium salt at the time of production and reaction of an epoxy compound, and may be mixed in the reaction system or may be previously mixed outside the reaction system.

Phosphoric acids specifically include, for example, an inorganic phosphoric acid such as phosphoric acid, polyphosphoric acid and pyrophosphoric acid; an inorganic phosphate such as sodium phosphate, potassium phosphate, ammonium phosphate, sodium hydrogenphosphate, potassium hydrogenphosphate, ammonium hydrogenphosphate, sodium dihydrogenphosphate, potassium dihydrogenphosphate and calcium dihydrogenphosphate; and phosphoric acid esters such as monomethyl phosphate, dimethyl phosphate, trimethyl phosphate, triethyl phosphate and triphenyl phosphate. Incidentally, in the case of phosphoric acid esters, this indicates phosphoric acid esters excluding an onium salt having a phosphoric acid ester group as the "substituent convertible to an active hydrogen-containing functional group or a salt thereof".

The phosphoric acids are preferably an inorganic phosphoric acid and preferably phosphoric acid.

The phosphonic acids include an aminomethylphosphonic acid, a phenylphosphonic acid, etc.

Among these, inexpensive phosphoric acid is preferred.

The use amount of at least either phosphoric acids or phosphonic acids is not particularly limited, and the proper use amount differs according to the kind of at least either phosphoric acids or phosphonic acids used or the kind of the catalytic metal component. The use amount is adjusted such that the pH of the aqueous phase of the later-described reaction system falls in an appropriate range, but in general, the equivalent of phosphorus contained in the at least either phosphoric acids or phosphonic acids is usually from 0.1 to 10 times by mol, preferably from 0.2 to 5.0 times by mol, more preferably from 0.2 to 3.0 times by mol, per one atom of the metal in the catalytic metal component used.

<Reaction Solvent in Epoxidation Reaction>

The mode of the reaction for producing an epoxy compound from an olefin compound in the present invention (hereinafter, sometimes referred to as "epoxidation reaction of the present invention") is not particularly limited but is usually performed in a two-phase reaction system of an aqueous phase and an organic phase. Because, by performing the reaction in a two-phase reaction system, the epoxy compound produced by the reaction of the present invention swiftly dissolves in the organic phase and as described later, the aqueous phase usually exhibits acidity, making it possible to prevent the epoxy ring of the produced epoxy compound from decomposition due to ring opening, rearrangement, etc.

The epoxidation reaction of the present invention may use a reaction solvent, if desired. In the case where the olefin compound used for the reaction or the epoxy compound produced is liquid under the reaction conditions, the compound may be used for the reaction without using a reaction solvent. Because, hydrogen peroxide usually contains water and by the mixing thereof, a two-phase reaction system can be formed. In the case where the olefin compound is solid, a reaction solvent is preferably used, and the compound may be dissolved or suspended in the solvent but usually, is preferably dissolved in a reaction solvent under the reaction temperature condition.

The reaction solvent used is not particularly limited as long as it does not participate in the reaction, and an organic solvent forming a two-phase system with water is preferred. The organic solvent includes aromatic hydrocarbons such as benzene, toluene and xylene, aliphatic hydrocarbons such as hexane, heptane, octane and dodecane, alcohols such as methanol, ethanol, isopropanol, butanol, hexanol and cyclohexanol, halogen-based solvents such as chloroform, dichloromethane and dichloroethane, ethers such as tetrahydrofuran and dioxane, ketones such as methyl ethyl ketone, methyl isobutyl ketone, cyclopentanone and anone, nitriles such as acetonitrile and butyronitrile, ester compounds such as ethyl acetate, butyl acetate and methyl formate, amides such as N,N'-dimethylformamide and N,N'-dimethylacetamide, ureas such as N,N'-dimethylimidazolidinone, and a mixture of such solvents, with aromatic hydrocarbons, aliphatic hydrocarbons, and a mixture of such a solvent being preferred. Furthermore, water and toluene, which are stable to the reaction and have a boiling point higher than the reaction temperature, are more preferred.

In the case of using a reaction solvent, the use amount thereof differs depending on the solubility of the compound, but since the reaction rate may decrease as the amount of the reaction solvent increases, the use amount of the reaction solvent is usually from 0.1 times or more and 10 times or less, preferably 5 times or less, more preferably 3 times or less, based on the olefin compound.

At the time of reaction, water may be further added. Hydrogen peroxide added usually contains water and therefore, even when water is not added, an aqueous phase is formed, but water may be added, if desired. In the case of adding water, the amount of water added is from 0.1 to 10 times, preferably from 0.1 to 5 times, more preferably from 0.1 to 3 times, based on the olefin compound.

In the present invention, the use amount of each of the catalytic metal component, onium salt and at least either phosphoric acids or phosphonic acids is as described above, but the mole fraction of catalytic metal component/onium salt is usually 0.2 or more, preferably 0.3 or more, more preferably 0.5 or more, and usually 4 or less, preferably 3 or less, more preferably 2 or less.

The mole fraction of catalytic metal component/(at least either phosphoric acids or phosphonic acids) is usually 0.2 or more, preferably 0.3 or more, more preferably 0.5 or more, and usually 4 or less, preferably 3 or less, more preferably 2 or less.

At least either phosphoric acids or phosphonic acids is preferably added such that the pH of the aqueous phase of the reaction solution falls in a proper range, but the pH is adjusted by adding an acid or a base, if desired.

The structure of the catalytic metal component such as tungsten acids in the present invention changes according to its pH and changes in the reaction activity. Therefore, the pH is preferably adjusted appropriately depending on the reactivity of olefin compound, the stability of epoxy group, the distribution or solubility of the compound to water, etc.

The pH of the aqueous phase of the reaction solution differs depending on the stability of epoxy compound or the solubility in water but is usually 2 or more, preferably 2.5 or more, and usually 6 or less, preferably 5 or less.

In the case where the reaction solution is a two-phase system of an aqueous phase and an organic phase, when the pH of the aqueous phase is excessively acidic, a ring-opening reaction or a rearrangement reaction of the epoxy group readily proceeds, and when the onium salt has an alkoxycarbonyl group, an acyloxy group, etc., such a group is hydrolyzed and may arise a problem, for example, the reactivity is reduced. Also, when the pH of the aqueous phase is excessively basic, there may arise a problem, for example, the reaction is extremely retarded, the hydrogen peroxide decomposes, or the alkoxycarbonyl group or acyloxy group hydrolyses.

In order to adjust the pH of the aqueous phase of the reaction solution, an acid such as phosphoric acid, aminomethylphosphonic acid, phenylphosphonic acid, sulfuric acid, nitric acid, hydrochloric acid and perchloric acid; an inorganic base such as sodium hydroxide, potassium hydroxide, sodium carbonate, potassium carbonate, sodium hydrogen carbonate, potassium hydrogen carbonate, phosphoric acid, disodium hydrogenphosphate and dipotassium hydrogenphosphate, or an organic base such as ammonia, methylamine and ethylamine, may be added, if desired, <Production Method of Epoxy Compound>

The production method of the present invention is specifically described below.

<Raw Material>

The compound having a carbon-carbon double bond used as a raw material in the present invention is not particularly limited as long as it is a compound having one or more carbon-carbon double bonds in the molecule, but the compound includes, for example, a compound represented by the following formula (30):

[Chem. 12]

$$[(A^{201}(OR)_{m201})-(X^{201})_{p201}]_{n201}-[(A^{202}-(X^{202})]_{n202}-[A^{203}(OR)_{m203}]_{n203} \quad (30)$$

(in formula (30), R represents an allyl group, the allyl group may be substituted with an alkyl group, a phenyl group or an alkoxycarbonyl group, $A^{201}$ represents an (m201+1)-valent aromatic or aliphatic hydrocarbon group that may have a substituent, $A^{202}$ represents a divalent aromatic or aliphatic hydrocarbon group that may have a substituent, and $A^{203}$ represents an (m203+1)-valent aromatic or aliphatic hydrocarbon group that may have a substituent, incidentally, in the following, the "aromatic or aliphatic hydrocarbon group" encompasses those having both hydrocarbon skeletons, for example, a group having, in the molecule, both structures of an aromatic ring and an aliphatic ring, each of $X^{201}$ and $X^{202}$ independently represents a direct bond or a divalent linking group that may have a substituent, p201 represents 0 or 1, each of m201 and m203 independently represents an integer of 1 or more, and n201 represents an integer of 1 or more, n202 represents 0 or an integer of 1 or more, and n203 represents 0 or 1, provided that in the case of n202=n203=0, when p201=0, $A^{201}$ becomes m201-valent and when p201=1, $X^{201}$ is a hydrogen atom or a monovalent group, and provided that a plurality of R, $A^{201}$, $A^{202}$, $X^{201}$, $X^{202}$, m201 or p201 contained in one molecule may be the same or different).

Among the compounds represented by formula (30), compounds represented by the following formulae (4) to (6) are preferred:

$$(A^1)\text{-}(OR)_{m1} \quad (4)$$

(in formula (4), R represents an allyl group, the allyl group may be substituted with an alkyl group, a phenyl group or an alkoxycarbonyl group, $A^1$ represents an m1-valent aromatic or aliphatic hydrocarbon group, and m1 represents an integer of 1 or more, provided that a plurality of R contained in one molecule may be the same or different).

The aromatic hydrocarbon group represented by $A^1$ includes an m1-valent group obtained by removing m1 hydrogens from an aromatic hydrocarbon having a carbon number of 6 to 14, such as benzene ring, naphthalene ring and anthracene ring, and is preferably a benzene ring having a carbon number of 6.

The aliphatic hydrocarbon group includes a group where the corresponding hydroxy group (that is, $(A^1)\text{-}(OH)_{m1}$) is a linear fatty acid polyhydric alcohol such as diethylene glycol, propane-1,3-diol, butane-1,4-diol and polyvinyl alcohol; a linear polyhydric alcohol having a branched substituent, such as neopentyl glycol, 2-methylpropanediol, 2,2-dimethylpropanediol and pentaerythritol; a polyhydric alcohol having an ether group in the molecular chain, such as diethylene glycol, triethylene glycol and polytetramethylene glycol (PTMG); alicyclic diols such as carbonate polyol (e.g., ethanediol carbonate, butanediol carbonate, ethanediol polycarbonate, butanediol polycarbonate), cyclopentanediol, cyclopentanedimethanol, cyclopentanediethanol, cyclohexanediol, cyclohexanedimethanol, cyclohexanediethanol, norbomanediol, norbornanedimethanol, norbomanediethanol and adamantanediol; a polyhydric alcohol having an ether group in the ring structure, such as erythritan, isosorbide and 1,4-dioxane-2,5-dimethanol; sugars such as glycoside, mannitol and sorbitol, in which a part of hydroxyl groups may be protected; or alkanolamines such as triethanolamine; (that is, a structure obtained by removing a hydroxyl group from these compounds).

The substituent other than the OR group, which may be substituted on the aromatic or aliphatic hydrocarbon group represented by $A^1$ includes an alkyl group having a carbon number of 1 to 4, such as methyl group, ethyl group and propyl group; an alkyloxy group having a carbon number of 1 to 4, such as methoxy group, ethoxy group and propyloxy group; a nitro group; etc. In the case of having a substituent other than the OR group, the upper limit of the number thereof, that is, the upper limit of the number of substituents substitutable on the group represented by $A^1$, is usually 4 or less, preferably 3 or less, and usually 1 or more.

m1 represents an integer of 1 or more and is preferably an integer of 2 or more, and the upper limit thereof is dependent on the number of hydrogen atoms substitutable on the group represented by $A^1$ but is usually 4 or less, preferably 2.

Preferred examples of the compound represented by formula (4) include those represented by any one of the formula group (7) below, and the compound may have, on the benzene ring, a substituent other than the OR group, for example, a tert-butyl group. The compound may also be a nuclear hydrogenated product where the aromatic ring is partially or wholly reduced. Furthermore, examples of the compound where $A^1$ is an aliphatic hydrocarbon group include isosorbide, 1,4-cyclohexanedimethanol, and 2,3-norbornane diol.

[Chem. 13]

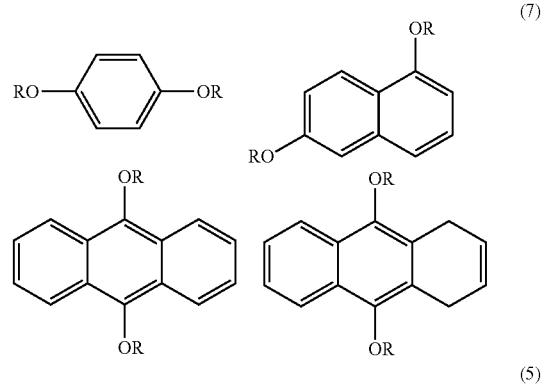

$$(RO)_{m2}\text{—}(A^{21})\text{—}[X^2\text{—}(A^{22})]_{n2}\text{—}X^2\text{—}(A^{21})\text{—}(OR)_{m2} \quad (5)$$

(in formula (5), R represents an allyl group, the allyl group may be substituted with an alkyl group, a phenyl group or an alkoxycarbonyl group, $A^{21}$ represents an (m2+1)-valent aromatic or aliphatic hydrocarbon group that may have a substituent, $A^{22}$ represents a divalent aromatic or aliphatic hydrocarbon group that may have a substituent, the substituents $A^{21}$ and $A^{22}$ connected through $X^2$ or a plurality of adjacent substituents $A^{22}$ may combine with each other to form a ring, $X^2$ represents a direct bond or a divalent linking group that may have a substituent, m2 represents an integer of 1 or more, and n2 represents 0 or an integer of 1 or more, provided that a plurality of R, $A^{21}$, $A^{22}$, $X^2$ or m2 contained in one molecule may be the same or different).

Each of $A^{21}$ and $A^{22}$ represents an (m1+2)-valent or divalent aromatic or aliphatic hydrocarbon group, and the hydrocarbon group may have a substituent.

The aromatic or aliphatic hydrocarbon group represented by $A^{21}$ and $A^{22}$ includes a group derived from the same hydrocarbon as $A^1$ in formula (4), and the carbon number thereof is also the same. The substituent that may be substituted on the group represented by $A^{21}$ or $A^{22}$ includes an alkyl group having a carbon number of 1 to 4, such as methyl group, ethyl group and propyl group; an alkyloxy group having a carbon number of 1 to 4, such as methoxy group, ethoxy group and propyloxy group; a nitro group; etc., with an alkyl group being preferred.

In the case where each of $A^{21}$ and $A^{22}$ has a substituent other than the group specified in formula (5), the upper limit of the number thereof, which is the upper limit of the number of substituents substitutable on the group represented by $A^{21}$, is usually 4 or less, preferably 3 or less.

$X^2$ represents a direct bond or a divalent linking group that may have a substituent, and the divalent linking group includes, for example, a methylene group, a dimethylmethylene group, a ditrifluoromethylmethylene group, an ethylene group, a propylene group, a 2,2-propylene group, —C(CH$_3$)=CH—, and an alicyclic hydrocarbon having a carbon number of 7 to 10 and having a crosslinked and condensed ring structure where a methylene group, a cyclohexylene group, —CO—, —O—, —S—, —SO2-, —SO—, —COO—, —C=C—, —C—O—C—, —CH(CN)—, —N=CH—, tetrahydrodicyclopentadiene, etc. is substituted with a cyclic structure (e.g., phenyl group). Incidentally, the divalent linking group may have an optional substituent. In the case where $X^2$ is an alkylene group, the alkylene group may have, as a substituent, an $(RO)_{m2}$-$(A^{21})$ group (wherein R, $A^{21}$ and m2 have the same meanings as in formula (5), and preferable ranges are also the same). That is, the compound represented by formula (5) may further have an $(RO)_{m2}$-$(A^{21})$- group, other than two $(RO)_{m2}$-$(A^{21})$- groups specified in the formula.

Among others, $X^2$ is preferably a direct bond, a divalent alkylene group having a carbon number of 1 to 4 (the alkylene group may be substituted with an aromatic hydrocarbon group, and the carbon number of the aromatic hydrocarbon group is preferably from 6 to 10), or an alicyclic hydrocarbon having a carbon number of 7 to 10 and having a crosslinked and condensed ring structure, more preferably a direct bond or an alkylene group having a carbon number of 1 to 2 (the alkylene group may be substituted with an aromatic hydrocarbon group, and the carbon number of the aromatic hydrocarbon group is preferably from 6 o 8).

Furthermore, the adjacent substituents $A^{21}$ and $A^{22}$ connected through $X^2$ or a plurality of adjacent substituents $A^{22}$ may combine with each other to form a ring. Specifically, an example thereof is a case where $A^{21}$ and $A^{22}$ or two $A^{22}$ combine through a methylene group or an ether group, and the group includes a 5- or 6-membered hydrogen ring, an oxygen atom-containing 6-membered ring, etc.

m2 represents an integer of 1 or more, and the upper limit thereof is dependent on the number of hydrogen atoms substitutable on the group represented by $A^{21}$ but is usually 4 or less, preferably 2 or less.

n2 represents 0 or an integer of 1 or more, and the upper limit thereof is usually 5, preferably 2.

Among the compounds represented by formula (5), a compound represented by the following formula (5-1) is preferred:

[Chem. 14]

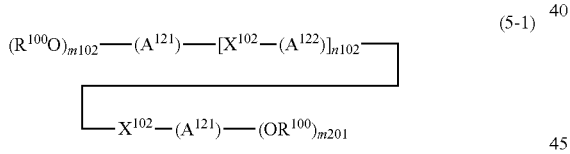

(5-1)

(in formula (5-1), $R^{100}$ represents an allyl group that may have a substituent, the substituent is an alkyl group having a carbon number of 1 to 6, a phenyl group or an alkoxycarbonyl group having a carbon number of 2 to 7, $A^{121}$ represents an {(m102)+1}-valent aromatic hydrocarbon group having a carbon number of 6 to 14, which may have a substituent, $A^{122}$ represents a divalent aromatic hydrocarbon group having a carbon number of 6 to 14, which may be substituted, the substituents $A^{121}$ and $A^{122}$ connected through $X^{102}$ or a plurality of substituents $A^{122}$ may combine with each other to form a ring, $X^{102}$ represents a direct bond, a methylene group, a dimethylmethylene group, a ditrifluoromethylmethylene group, an ethylene group, —C(CH$_3$)=CH—, a methylene group that may be substituted with a phenyl group or $(R^{100})_{m2}$-$(A^{121})$-, a cyclohexylene group, —CO—, —O—, —SO$_2$—, —COO—, —N=CH— or a tetrahydrodicyclopentadienylene group, provided that a plurality of $R^{100}$, $A^{121}$, $A^{122}$, $X^{102}$ or m102 contained in one molecule may be the same or different, m102 represents an integer of 1 to 4, and n102 represents an integer of 0 to 5).

In formula (5-1), among the substituents that may be substituted on $R^{100}$, a methyl group, a phenyl group, a methoxycarbonyl group and an ethoxycarbonyl group are preferred, but $R^{100}$ is preferably an unsubstituted allyl group.

$X^{102}$ is preferably a direct bond, a divalent alkylene group having a carbon number of 1 to 4 (the alkylene group may be substituted with an aromatic hydrocarbon group, and the carbon number of the aromatic hydrocarbon group is preferably from 6 to 10), or an alicyclic hydrocarbon having a carbon number of 7 to 10 and having a crosslinked and condensed ring structure, more preferably a direct bond or an alkylene group having a carbon number of 1 to 2 (the alkylene group may be substituted with an aromatic hydrocarbon group, and the carbon number of the aromatic hydrocarbon group is preferably from 6 o 8).

m102 is preferably 1 or 2, and n102 is preferably 0, 1 or 2.

Specific examples of the compound represented by formula (5) include compounds represented by the following structural formulae (n represents an integer of 1 or more), and nuclear hydrogenated products thereof where the aromatic ring is partially or wholly reduced. Also, these compounds may have, on the benzene ring, a substituent other than the OR group and the methyl specified.

<Specific Examples of Compound Represented by Formula (5)>

[Chem. 15]

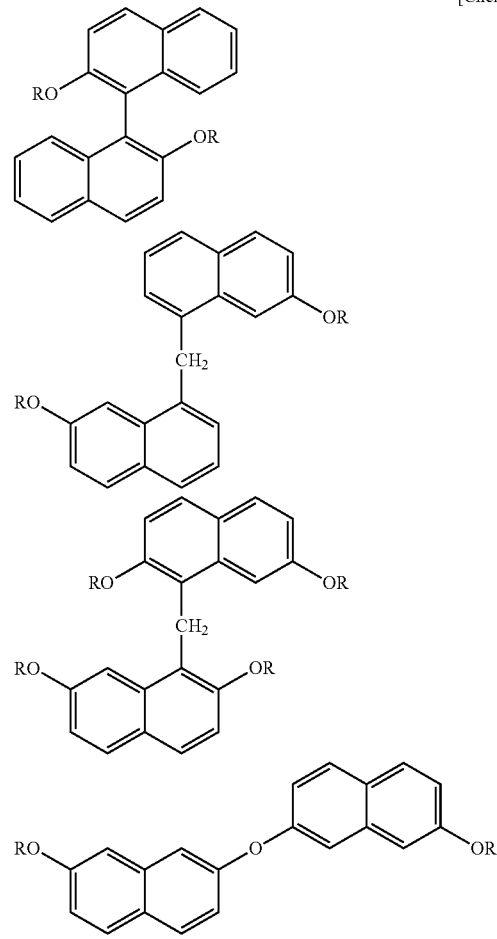

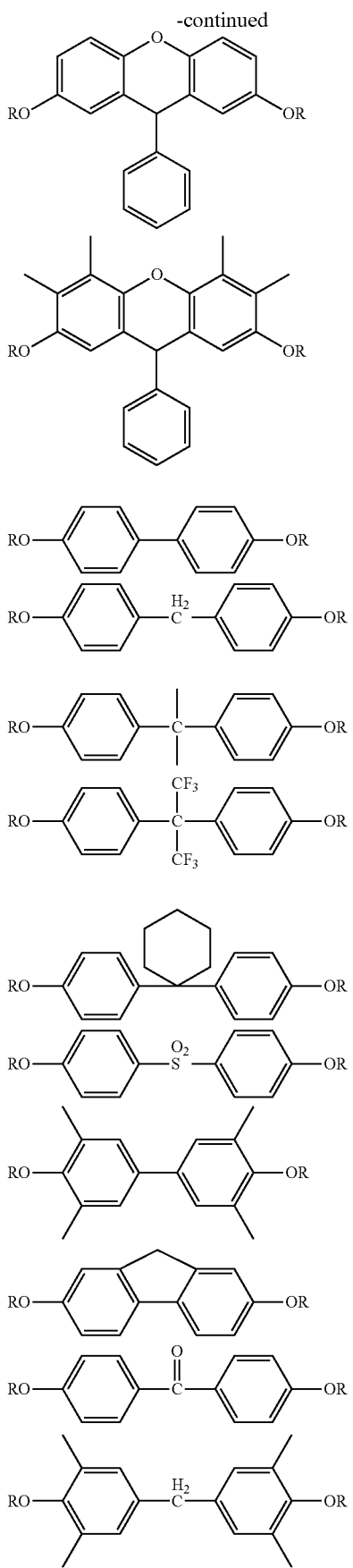

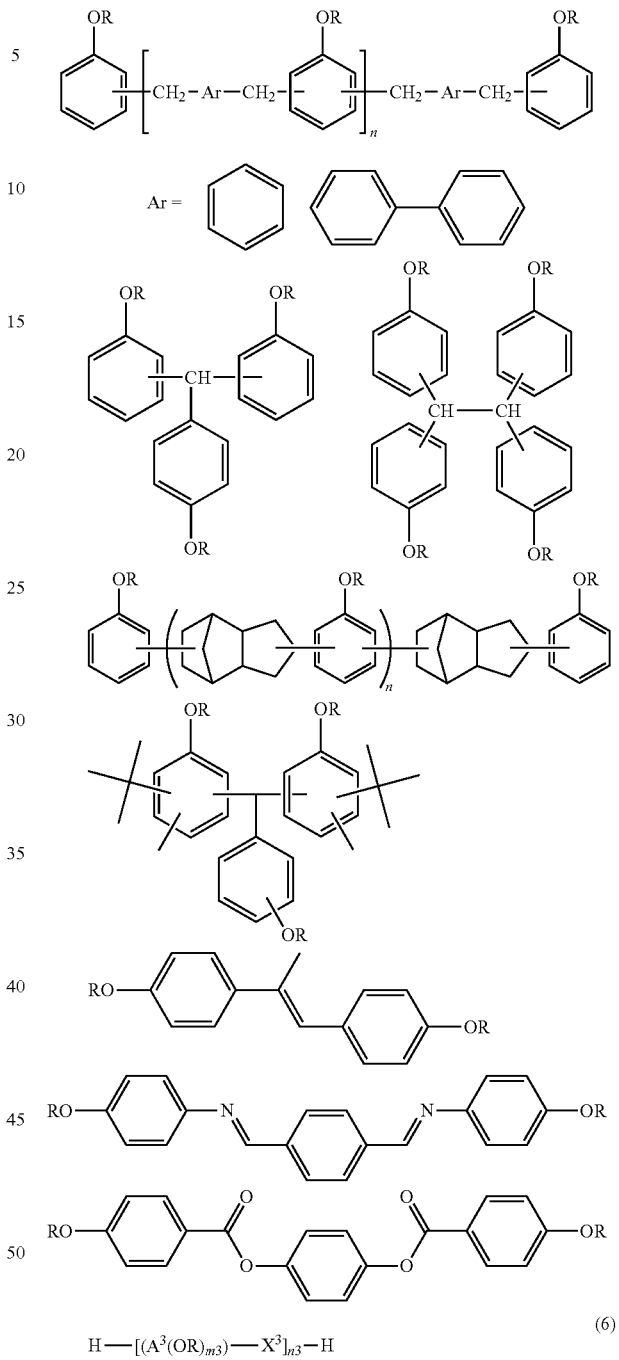

$$H\!-\!\!-\![(A^3(OR)_{m3})\!-\!\!-\!X^3]_{n3}\!-\!\!-\!H \quad (6)$$

(wherein R represents an allyl group, the allyl group may be substituted with an alkyl group, a phenyl group or an alkoxycarbonyl group, $A^3$ represents an (m3+2)-valent aromatic or aliphatic hydrocarbon group that may have a substituent, $X^3$ represents a direct bond, an alkylene group that may have a substituent, or —$R^{61}$-phenylene-$R^{62}$—, each of $R^{61}$ and $R^{62}$ independently represents an alkylene group, m3 represents an integer of 1 or more, and n3 represents an integer of 2 or more, provided that a plurality of G, $A^3$, $X^3$ or m3 contained in one molecule may be the same or different).

The aromatic or aliphatic hydrocarbon group represented by $A^3$ includes a group derived from the same hydrocarbon as $A^1$ in formula (4), and the carbon number thereof is also the same.

$X^3$ represents a direct bond, an alkylene group that may have a substituent, or —$R^{61}$-phenylene-$R^{62}$—, wherein each of $R^{61}$ and $R^{62}$ independently represents an alkylene group. The alkylene group represented by $X^3$, which may have a substituent, includes the same alkylene group as $X^2$ in formula (5), and among others, is preferably an alkylene group having a carbon number of 1 to 4, preferably a carbon number of 1 or 2. Each of $R^{61}$ and $R^{62}$ in —$R^{61}$-phenylene-$R^{62}$— is independently an alkylene group having a carbon number of 1 to 4, preferably a carbon number of 1 or 2.

m3 represents an integer of 1 or more, and the upper limit thereof is dependent on the number of hydrogen atoms substitutable on the group represented by $A^3$ but is usually 4 or less, preferably 2 or less. n3 represents an integer of 2 or more and is usually 20 or less, preferably 10 or less.

Specific examples of the compound represented by formula (6) include compounds represented by the following structural formulae (in the formulae, n and n' have the same meaning as n3), and nuclear hydrogenated products thereof where the aromatic ring is partially or wholly reduced. Also, these compounds may have, on the benzene ring, a substituent other than the —OR group and the methyl group specified.

<Specific Examples of Compound Represented by Formula (6)>

[Chem. 17]

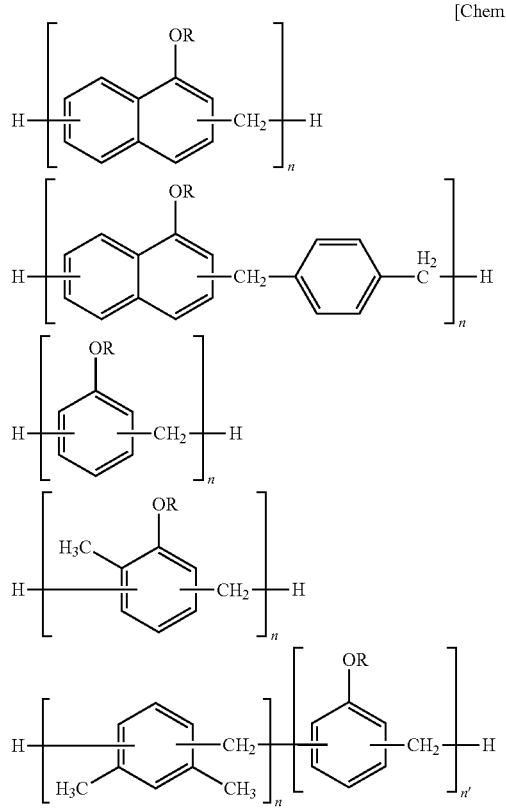

Another example of the compound having a carbon-carbon double bond, which is used as a raw material in the present invention, includes a cyclic olefin compound represented by the following formula (36):

[Chem. 18]

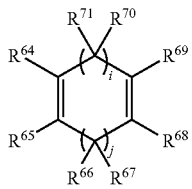

(36)

(in formula (36), each of i and j independently represents an integer of 1 to 4, and each of $R^{64}$ to $R^{71}$ independently represents a hydrogen atom, a halogen atom, an alkyl group that may have a substituent, an aromatic hydrocarbon group that may have a substituent, a nitro group, an alkoxyl group, a carbonyl group, an acyloxy group, or a carboxyl group or a salt thereof, provided that out of $R^{64}$ to $R^{71}$, any two or more members may combine with each other to form a ring).

Each of $R^{64}$ to $R^{71}$ independently represents a hydrogen atom, a halogen atom, an alkyl group that may have a substituent, an aromatic hydrocarbon group that may have a substituent, a nitro group, an alkoxyl group, a carbonyl group, an alkoxycarbonyl group, an acyloxy group, or a carboxyl group or a salt thereof.

The halogen atom includes, for example, a fluorine atom, a chlorine atom, and a bromine atom.

The alkyl group is preferably an alkyl group having a carbon number of 1 to 20, and examples thereof include a linear or branched alkyl group such as methyl group, ethyl group, n-propyl group, isopropyl group, n-butyl group, sec-butyl group, tert-butyl group, pentyl group, hexyl group, heptyl group, octyl group, nonyl group, decyl group, cetyl group and stearyl group; and a cycloalkyl group such as cyclobutyl group, cyclopentyl group, cyclohexyl group and cyclooctyl group. This alkyl group may have a substituent, and the substituent includes, for example, a halogen atom such as fluorine atom, chlorine atom and bromine atom; an alkoxyl group such as methoxy group, ethoxy group, propoxy group, isopropoxy group and butoxy group; a nitro group; a carboxyl group; an alkoxycarbonyl group such as methoxycarbonyl group and ethoxycarbonyl group; and an acyloxy group such as acetyloxy group and propionyloxy group.

The aromatic hydrocarbon group includes, for example, a phenyl group and a naphthyl group.

The aromatic hydrocarbon group may have a substituent, and the substituent includes, for example, a halogen atom such as fluorine atom, chlorine atom and bromine atom; an alkoxyl group such as methoxy group, ethoxy group, propoxy group, isopropoxy group and butoxy group; a nitro group; a carboxyl group; an alkoxycarbonyl group such as methoxycarbonyl group and ethoxycarbonyl group; an acyl group such as acetyl group, propionyl group and benzoyl group; and an acyloxy group such as acetyloxy group and propionyloxy group.

The alkoxyl group includes, for example, a methoxy group, an ethoxy group, a propoxy group, an isopropoxy group, and a butoxy group.

The acyloxy group includes, for example, an acetyloxy group, a propionyloxy group, and a benzoyloxy group.

The salt of a carboxyl group includes, for example, an alkali metal salt such as sodium salt and potassium salt.

Incidentally, out of $R^{64}$ to $R^{71}$, any two or more members may combine with each other to form a ring.

Each of i and j independently represents an integer of 1 to 4, preferably from 1 to 3, more preferably 1 or 2, and most preferably 2.

The cyclic olefin represented by formula (36) includes, for example, cyclic non-conjugated olefins such as 1,4-cyclohexadiene, 1,5-cyclooctadiene, 1,5,9-cyclododecatriene, 1,5-dimethyl-1,5-cyclooctadiene, dicyclopentadiene and 2,5-norbornadiene.

The compound further includes, for example, a styrene compound represented by the following formula (37):

[Chem. 19]

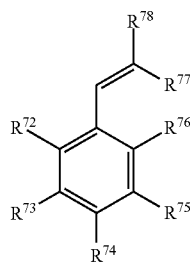

(37)

(in formula (37), each of $R^{72}$ to $R^{76}$ independently represents a hydrogen atom, a linear or branched alkyl group having a carbon number of 1 to 8, an alkoxy group having a carbon number of 1 to 8, a cycloalkyl group having a carbon number of 3 to 7, an aromatic hydrocarbon group, an aralkyl group, an acyl group, a hydroxy group, a halogen atom, a carboxyl group or an acyloxy group, and each of $R^{77}$ and $R^{78}$ independently represents a hydrogen atom, a linear or branched alkyl group having a carbon number of 1 to 8, an alkoxy group having a carbon number of 1 to 8, an alkoxycarbonyl group having a carbon number of 2 to 8, a cycloalkyl group having a carbon number of 3 to 7, an aromatic hydrocarbon group, an aralkyl group, an acyl group, a carboxyl group or an acyloxy group, provided that any two or more members out of $R^{72}$ to $R^{78}$ may combine with each other to form a ring).

Specific examples of the styrenes represented by formula (37) include styrene, 4-methylstyrene, 4-fluorostyrene, 2,4-difluorostyrene, 3-chlorostyrene, 4-chlorostyrene, 4-bromostyrene, 4-nitrostyrene, 4-vinylbenzoic acid, α-methylstyrene, β-methylstyrene, 1-phenyl-1-cyclohexene, indene, and dihydronaphthalene.

The olefin compound for use in the present invention may be subjected to, if desired, a pretreatment such as removal of impurities when using the compound for the epoxidation reaction of the present invention.

The epoxidation reaction using hydrogen peroxide is sometimes affected by a foreign material coming from the raw material, the solvent, the reaction vessel, the incidental equipment such as pipe and feed pump, etc., for example, a metal, activated carbon, silica gel or glass piece. The oxide of hydrogen oxide, etc. may decompose upon contact with the foreign material above to generate heat of reaction or oxygen and involve a danger. It is preferable to keep the reaction solution from mixing or effect of such a foreign material. Specifically, in order to remove those foreign materials, it is preferred that the olefin compound is filtered, the olefin compound is washed with an acidic aqueous solution, the olefin compound is washed with a chelating agent (a compound capable of forming a chelate with a metal; specifically, a metal masking agent), or the reaction is performed by allowing a chelating agent to exist together at the time of epoxidation reaction.

The acid employed in the acidic aqueous solution for washing the olefin compound used as the raw material is not particularly limited in its kind but, specifically, includes an inorganic acid such as hydrochloric acid, sulfuric acid, nitric acid and phosphoric acid; and an inorganic acid such as acetic acid and citric acid.

The pH of the acidic aqueous solution is not particularly limited and differs according to the stability of the olefin compound used, but the washing is performed at a pH of usually 1 or more, preferably 3 or more, and usually 5 or less, preferably 4 or less. Various salts may be added for the purpose of adjusting the pH, for example, sodium sulfate, sodium acetate, sodium phosphate, disodium hydrogenphosphate, or sodium citrate may be added.

Specifically, a mixed aqueous solution of acetic acid and sodium sulfate is preferred. For example, an aqueous solution containing 4% acetic acid and 1% sulfuric acid and having a pH of about 4 is more preferred. By performing the washing treatment above, the metal is solubilized in water and removed together with the aqueous phase.

The aqueous solution containing a chelating agent is not particularly limited as long as it is an aqueous solution containing a compound having a metal chelating ability, but an aqueous solution containing a so-called metal masking agent is preferred. The metal masking agent includes, for example, ethylenediaminetetraacetic acid, pyrophosphoric acid, etc. described in JP-T-2002-501005. A method of washing the compound with water containing at least either ethylenediaminetetraacetic acid or pyrophosphoric acid is preferred. By performing this treatment, the metal is solubilized in water and removed together with the aqueous phase.

Also, the chelating agent may be used by adding it to the reaction system, and a method of adding at least either ethylenediaminetetraacetic acid or pyrophosphoric acid to the reaction solution is preferred. Because, the chelating agent as the metal masking agent chelates metals, whereby decomposition of peroxide can be suppressed.

<Reaction Operation>

The specific method for the reaction operation in the production method of the present invention is not particularly limited, but hydrogen peroxide, at least either a tungsten compound or a molybdenum compound, an onium salt, and if desired, at least either phosphoric acids or phosphonic acids are added to the olefin compound, and if desired, the above-described organic solvent and a buffer solution are added.

The additions and mixing order of respective components are not particularly limited as long as the reaction is not inhibited, but heat generation is involved at the time of epoxidation reaction and decomposition of hydrogen peroxide and therefore, from the standpoint of controlling the reaction progress or heat generation, a method where hydrogen oxide is gradually added after adding respective components or where hydrogen peroxide in an amount necessary to oxidize at least either a tungsten compound or a molybdenum compound is previously added to form at least either a tungsten peroxide or a molybdenum peroxide and then the remaining hydrogen peroxide is gradually added, is preferred. The method for adding hydrogen peroxide may be addition in parts or may be continuous and gradual addition. From a safety aspect, the hydrogen peroxide is preferably added additionally according to the progress of reaction so as to prevent unreacted hydrogen peroxide from residing in the reaction system.

<Reaction Conditions>

The reaction temperature in the production method of the present invention is not particularly limited as long as the reaction is not inhibited, but the reaction temperature is usually 10° C. or more, preferably 35° C. or more, more preferably 60° C. or more, and usually 90° C. or less, preferably 80° C. or less, more preferably 75° C. or less. Because, if the reaction temperature is less than the lower limit above, the reaction rate may be reduced, whereas if the reaction temperature exceeds the upper limit above, this may be not preferred from a safety aspect.

The reaction time can be appropriately selected according to, for example, the reaction temperature, the amount of catalyst, or the kind of raw material and is not particularly limited but is usually 1 hour or more, preferably 3 hours or more, more preferably 4 hours or more, and usually 48 hours or less, preferably 36 hours or less, more preferably 24 hours or less.

From a safety aspect, the reaction in the production method of the present invention is preferably performed under atmospheric pressure in a nitrogen stream.

Although this is not particularly limited, the production method of the present invention is usually performed in a two-phase reaction system of an aqueous phase and an organic phase.

The appropriate pH during the reaction depends on the structure of the reaction raw material. For example, a cyclic olefin is easily epoxidized, but the epoxy produced tends to undergo transition or cleavage, and therefore, a reaction under nearly neutral conditions is preferred. On the other hand, an allyloxy ether is hardly epoxidized as compared with a cyclic olefin and is less likely to undergo cleavage and for this reason, there is a tendency that acidic conditions more than in the case of a cyclic olefin are preferred. The pH is not particularly limited, but the pH of the aqueous phase is usually 2 or more, preferably 2.5 or more, and usually 6 or less. At the time of reaction, the pH varies depending on the amount of hydrogen peroxide in the aqueous phase, or the produced epoxy is cleaved under acidic conditions in the latter half of the reaction. Therefore, it is preferable to appropriately add an acid or a base according to the progress of the reaction and thereby keep the pH in an optimal range.

In the production method of the present invention, a buffer solution can also be used. As for the kind of the buffer solution, a buffer solution according to the objective pH may be appropriately used, as long as it does not inhibit the reaction. Examples of the buffer solution include an aqueous phosphate solution and as the combination of a hydrogen phosphate salt, a dihydrogen phosphate salt or a phenylphosphoric acid, include citric acid/sodium citrate, and acetic acid/sodium acetate. Depending on the case, the buffer solution may be formed by the combination with the above-described tungstic acids.

In the production method of the present invention, a co-oxidant may also be used for the purpose of allowing the smooth progress of the reaction. Specifically, a carboxylic acid, preferably an aliphatic carboxylic acid having a carbon number of 1 to 10, may be incorporated into the catalyst composition. The co-oxidant may be added to the composition or, for example, in the case of an onium salt having an ester group, the co-oxidant may be generated by hydrolysis of the ester group.

In addition, similarly, a surfactant or a nitrogen-containing compound such as amines and pyridine ring compound may be incorporated into the oxidant composition.

<Substrate Removal Step: After-Treatment Step>

In the production method of the present invention, an after-treatment is performed after the completion of epoxidation reaction to convert the substituent contained in the onium salt to an active hydrogen-containing functional group or a salt thereof. The onium salt after conversion of the substituent transfers from the organic phase to the aqueous phase in the reaction system and therefore, can be easily separated from the epoxy compound present in the organic phase. The epoxy compound as the product may be, if desired, further purified.

The method for converting the substituent contained in the onium salt to an active hydrogen-containing functional group or a salt thereof is not limited as long as the object of the present invention is not impaired, but the method includes, for example, a method of converting the substituent by adding an acidic aqueous solution or a basic aqueous solution to an extent not decomposing the epoxy compound, a method of converting the substituent by catalytic hydrogenation, a method of converting the substituent by heating, a method of converting the substituent by using an auxiliary agent or enzyme capable of selectively converting the substituent, a method of converting the substituent by photoreaction, and a method of converting the substituent by microwave irradiation.

After the conversion to an active hydrogen-containing functional group or a salt thereof, the onium salt transfers into water in the reaction system and as the method for separating the onium salt from the epoxy compound, a separation method according to the physical properties of the onium salt, not involving decomposition of the epoxy compound, is employed. The separation method includes, for example, liquid separation, washing, suspension-washing, adsorption, filtration, and distillation.

This is specifically described below by referring to, for example, the case of using an onium salt having an alkoxycarbonyl group or an acyloxy group.

After the completion of epoxidation reaction, the aqueous phase is subjected to disposal, water washing and, if desired, addition of a reductant for performing a quenching treatment of excessive hydrogen peroxide. The reductant is not particularly limited but includes sodium sulfite, sodium thiosulfate, hydrazine, oxalic acid, etc. Also, the quenching treatment of excessive hydrogen peroxide by the addition of a reductant may be performed after a treatment of converting the onium salt above to a water-soluble salt.

Subsequently, a treatment of converting the onium salt to a water-soluble salt is performed. Specifically, the treatment is preferably for hydrolysis of the ester group contained in the alkoxycarbonyl group or acyloxy group. The method for hydrolysis is not particularly limited but usually, a method using a basic compound is employed. The basic compound specifically includes a metal hydroxide such as sodium hydroxide, potassium hydroxide, magnesium hydroxide and calcium hydroxide, a metal carbonate such as sodium carbonate and potassium carbonate, a phosphate such as sodium phosphate and sodium hydrogenphosphate, and a basic solid such as alumina. For the reason that the operation is simple and easy, hydrolysis by a basic aqueous solution is preferred, and this hydrolysis specifically includes hydrolysis by an aqueous sodium hydroxide solution or an aqueous potassium hydroxide solution. Incidentally, in the case where the hydrolyzed compound of the onium salt has a property as a surfactant, the base treatment operation is preferably performed after distilling off or while distilling off the reaction solvent, because the hydrolysate of the onium salt can be easily separated from the product.

The concentration, pH and temperature of the basic aqueous solution are not particularly limited but can be selected in the range where the epoxy compound is not decomposed. Specifically, as for the concentration of the aqueous solution, a basic aqueous solution with a normality of 0.1 to 5N, preferably from 0.3 to 3N, more preferably from 0.5 to 2N, is used. The pH of the aqueous solution is usually from 10 to 12. As for the temperature of the aqueous solution, the treatment is performed usually at 0° C. or more, preferably at 20° C. or more, and usually at 60° C. or less, preferably at 45° C. or less. After the hydrolysis of the ester group, the resulting water-soluble onium salt is removed by washing. In association therewith, the catalytic metal component is also removed by the washing.

In the thus-obtained epoxy compound, the contents of the metal derived from the catalytic metal component, for example, tungsten, and the onium salt are small. Also, although this may vary according to the chlorine content of the compound used for the reaction, the epoxy compound is generally characterized in that the chlorine content is small compared with an epoxy compound synthesized using epichlorohydrin.

<Purification>

The epoxy compound obtained by the method above may be, if desired, further purified. The specific purification method is not particularly limited, and a known method may be appropriately used. In the case where the epoxy compound is a solid, the purification method includes crystallization, suspension-washing, liquid separation, adsorption, etc., and in the case where the epoxy compound is a liquid, the purification method includes liquid separation, washing, adsorption, and distillation.

The purification by liquid separation or washing includes a case of combining water and an organic solvent insoluble or sparingly soluble in water, and a case of combining a plurality of organic solvents incapable of intermixing with each other. The combination of water and an organic solvent insoluble or sparingly soluble in water includes, for example, a combination of water with an organic solvent such as ethyl acetate, toluene, diethyl ether, diisopropyl ether and n-hexane.

The combination of a plurality of organic solvents incapable of intermixing with each other includes, for example, a combination of N,N'-dimethylformamide and at least one member out of n-heptane, n-hexane, n-pentane, diisopropyl ether and xylene, a combination of dimethylsulfoxide and at least one member out of n-heptane, n-hexane, n-pentane, diisopropyl ether, diethyl ether and xylene, a combination of acetonitrile and at least one member out of n-heptane, n-hexane, n-pentane, cyclohexane and cyclopentane, and a combination of methanol and at least one member out of n-heptane, n-hexane and n-pentane.

The purification by crystallization may be performed by any of, for example, a method of crystallizing the epoxy compound by cooling while distilling off the solvent under reduced pressure or without distilling off the solvent, a method of precipitating the epoxy compound by adding a so-called poor solvent, a method of precipitating the epoxy compound by combining a solvent allowing for high solubility of the compound, a so-called good solvent, and a poor solvent, and a solvent of crystallizing the epoxy compound by adding water after the completion of reaction. The solvent may be any of an organic solvent, water, a mixture thereof, a combination of organic solvents, and the like, and a better solvent is selected according to the solubility of the compound. The organic solvent includes esters such as ethyl acetate, aliphatic hydrocarbons such as heptane, hexane and cyclohexane, aromatic hydrocarbons such as benzene, toluene and xylene, aprotic solvents such as acetonitrile, tetrahydrofuran, dioxane and 1,2-dimethoxyethane, alcohols such as methanol, ethanol, 2-propanol and n-butanol, ketones such as acetone and methyl ethyl ketone, and aprotic polar solvents such as N,N'-dimethylformamide, N-methylpyrrolidone and dimethylsulfoxide.

The purification by suspension-washing uses a solvent allowing for low solubility of the compound, a so-called poor solvent. The preferable poor solvent differs depending on the compound but includes a solvent having high polarity, e.g., alcohols such as methanol, and conversely, an aliphatic hydrocarbon having low polarity, such as butane, hexane and cyclohexane.

The water-soluble solvent includes tetrahydrofuran, 1,3-dioxolane, N,N,N-dimethylformamide, dimethylsulfoxide, etc., and such a solvent can be used by mixing it with water. If the amount of the solvent is too small, the purification effect is insufficient, and if the amount of the solvent is too large, this leads to reduction in the recovery percentage. After the completion of suspension-washing, the solid material is recovered by filtration and dried, whereby the target compound can be obtained.

In the purification by adsorption, chlorine-containing impurities are removed, and the adsorbent includes activated carbon, activated earth, molecular sieve, activated alumina, zeolite, ion exchange resin, etc.

Among these purification methods, in view of the operation, a liquid separation method is preferred irrespective of the condition of the epoxy compound. In the case where the epoxy compound is a solid, a crystallization method is effective.

<Epoxy Composition>

The epoxy compound is obtained through the above-described epoxidation reaction, the step of separating/removing the catalytic metal component, onium salt, etc., and, if desired, the purification step.

The epoxy composition obtained by the production method of the present invention is obtained as a composition having an extremely reduced content of a metal derived from the catalytic metal, and the content of the metal is usually 200 ppm or less, preferably 100 ppm or less, more preferably 10 ppm or less, still more preferably 1 ppm or less.

Similarly, in the epoxy composition obtained by the production method of the present invention, the nitrogen content derived from the onium salt is small, and the content is usually 500 ppm or less, preferably 200 ppm or less, more preferably 10 ppm or less.

In the epoxy composition obtained by the production method of the present invention, the content of a halogen atom is small, and the content is usually 200 ppm or less, preferably 50 ppm or less, more preferably 10 ppm or less. The production method of the present invention can be used for the production of the later-described epoxy resin and in addition, for the production of a medical intermediate, etc. having an epoxy structure. Also, the epoxy composition of the present invention can be used as the later-described epoxy resin and in addition, as a medical intermediate, etc. having an epoxy structure. The intermediate includes, for example, an antifungal or antidiabetic intermediate having a halogen-substituted styrene oxide structure. The epoxy composition obtained by the method of the present invention has a small impurity content and therefore, is relieved of the fear of toxicity attributable to impurities.

The epoxy compound in the present invention (hereinafter, sometimes referred to as the epoxy compound α) is not particularly limited as long as it is a compound having one or more epoxy groups in the molecule, but the specific epoxy compound includes a compound represented by the following formula (32):

[Chem. 20]

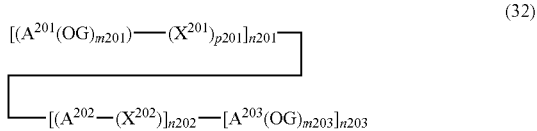

(32)

(in formula (32), G represents a glycidyl group (2,3-epoxy-propanyl group), and the glycidyl group may be substituted with an alkyl group, a phenyl group or an alkoxycarbonyl group;

$A^{201}$ represents an (m201+1)-valent aromatic or aliphatic hydrocarbon group that may have a substituent, $A^{202}$ represents a divalent aromatic or aliphatic hydrocarbon group that may have a substituent, and $A^{203}$ represents an (m203+1)-valent aromatic or aliphatic hydrocarbon group that may have a substituent;

each of $X^{201}$ and $X^{202}$ independently represents a direct bond or a divalent linking group that may have a substituent;

p201 represents 0 or 1;

each of m201 and m203 independently represents an integer of 1 or more;

n201 represents an integer of 1 or more, n202 represents 0 or an integer of 1 or more, and n203 represents 0 or 1;

provided that in the case of n202=n203=0, when p201=0, $A^{201}$ becomes m201-valent and when p201=1, $X^{201}$ is a hydrogen atom or a monovalent group; and provided that a plurality of G; $A^{201}$, $A^{202}$, $X^{201}$, $X^{202}$, m201 or p201 contained in one molecule may be the same or different).

In formula (32), G represents a glycidyl group (2,3-epoxypropanyl group). The glycidyl group may be substituted with an alkyl group, a phenyl group or an alkoxycarbonyl group, and of these substituents, a methyl group, a phenyl group, a methoxycarbonyl group and an ethoxycarbonyl group are preferred. In particular, G is preferably an unsubstituted glycidyl group.

Incidentally, $A^{201}$ to $A^{203}$, $X^{201}$, $X^{202}$, n201 to n203, m201, m203 and p201 in formula (32) have the same meanings as in formula (30), and preferable ranges are also the same.

Among the compounds represented by formula (32), the compounds represented by the following formulae (13) to (15) are preferred.

$(A^1)$-$(OG)_{m1}$ (13)

(in formula (13), G represents a glycidyl group (2,3-epoxypropanyl group), and the glycidyl group may be substituted with an alkyl group, a phenyl group or an alkoxycarbonyl group; $A^1$ represents an m1-valent aromatic or aliphatic hydrocarbon group that may have a substituent; and m1 represents an integer of 1 or more, provided that a plurality of G contained in one molecule may be the same or different).

Here, specific examples and preferable range of G are the same as those in formula (32), and specific examples and preferable range of $A^1$ are the same as those in formula (4).

$(GO)_{m2}$-$(A^{21})$-$[X^2$-$(A^{22})]_{n2}$-$X^2$-$(A^{21})$-$(OG)_{m2}$ (14)

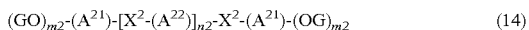

(in formula (14), G represents a glycidyl group, and the glycidyl group may be substituted with an alkyl group, a phenyl group or an alkoxycarbonyl group; $A^{21}$ represents an (m2+1)-valent aromatic or aliphatic hydrocarbon group that may have a substituent; $A^{22}$ represents a divalent aromatic or aliphatic hydrocarbon group that may have a substituent; the substituents $A^{21}$ and $A^{22}$ connected through $X^2$ or a plurality of adjacent substituents $A^{22}$ may combine with each other to form a ring; $X^2$ represents a direct bond or a divalent linking group that may have a substituent; m2 represents an integer of 1 or more; and n2 represents 0 or an integer of 1 or more; provided that a plurality of G, $A^{21}$, $A^{22}$, $X^2$ or m2 contained in one molecule may be same or different).

Here, specific examples and preferable range of G are the same as those in formula (32), and specific examples and preferable ranges of $A^{21}$, $A^{22}$, $X^2$, m2 and n2 are the same as those in formula (5).

H—$[(A^3(OG)_{m3}$-$X^3]_{n3}$-H (15)

(in formula (15), G represents a glycidyl group, and the glycidyl group may be substituted with an alkyl group, a phenyl group or an alkoxycarbonyl group; $A^3$ represents an (m3+2)-valent aromatic or aliphatic hydrocarbon group that may have a substituent; $X^3$ represents a direct bond, an alkylene group that may have a substituent, or —$R^{61}$-phenylene-$R^{62}$-, wherein each of $R^{61}$ and $R^{62}$ independently represents an alkylene group; m3 represents an integer of 1 or more; and n3 represents an integer of 2 or more; provided that a plurality of G, $A^3$, $X^3$ or m3 contained in one molecule may be same or different).

Here, specific examples and preferable range of G are the same as those in formula (32), and specific examples and preferable ranges of $A^3$, $X^3$, m3 and n3 are the same as those in formula (6).

The epoxy compound α obtained by the production method of the present invention is usually obtained as a composition containing a compound β having a structure where one or more glycidyl groups contained in the epoxy compound α are substituted with a 3-acyloxy-2-hydroxypropyl group (wherein the acyl group is a group represented by —CO—$R^{35}$ or —CO—Z).

These compounds are produced by the reaction of an onium salt and an epoxy compound under base conditions, which occurs mainly at the time of after-treatment step after the reaction.

Z represents a monovalent aliphatic hydrocarbon group having a carbon number of 1 to 25, in which a part of carbon atoms may be substituted with a heteroatom, or a monovalent aromatic hydrocarbon group having a carbon number of 4 to 25, which may have a substituent.

$R^{35}$ represents a group represented by any one of the following (18) to (20):

[Chem. 21]

(18)

(19)

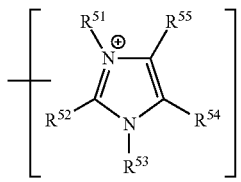

(20)

(in formula (18), $R^{41}$ represents a direct bond or a divalent aliphatic hydrocarbon group having a carbon number of 1 to 25, in which a part of carbon atoms may be substituted with a heteroatom, and each of $R^{42}$ to $R^{44}$ independently represents an alkyl group having a carbon number of 1 to 25, in which a part of carbon atoms may be substituted with a heteroatom, or a benzyl group;

in formula (19), any one of $R^{45}$ to $R^{50}$ represents a direct bond or a divalent aliphatic hydrocarbon group having a carbon number of 1 to 25, in which a part of carbon atoms may be substituted with a heteroatom, provided that in the case where $R^{45}$ is a direct bond or a divalent aliphatic hydrocarbon group having a carbon number of 1 to 25, in which a part of carbon atoms may be substituted with a heteroatom, each of $R^{46}$ to $R^{50}$ independently represents a hydrogen atom, a halogen atom, a cyano group, a nitro group, an alkyl group having a carbon number of 1 to 25, in which a part of carbon atoms may be substituted with a heteroatom, a phenyl group, a phenoxy group, a benzyl group, an N-alkylcarbamoyl group or an N-alkylsulfamoyl group, and in the case where any one of $R^{46}$ to $R^{50}$ is a direct bond or a divalent aliphatic hydrocarbon group having a carbon number of 1 to 25, in which a part of carbon atoms may be substituted with a heteroatom, each of other four members independently represents a hydrogen atom, a halogen atom, a cyano group, a nitro group, an alkyl group having a carbon number of 1 to 25, in which a part of carbon atoms may be substituted with a heteroatom, a phenyl group, a phenoxy group, a benzyl group, an N-alkylcarbamoyl group or an N-alkylsulfamoyl group, and $R^{45}$ represents an alkyl group having a carbon number of 1 to 25, in which a part of carbon atoms may be substituted with a heteroatom, or a benzyl group; and in formula (20), any one of $R^{51}$ to $R^{55}$ represents a direct bond or a divalent aliphatic hydrocarbon group having a carbon number of 1 to 25, in which a part of carbon atoms may be substituted with a heteroatom, provided that in the case where either one of $R^{51}$ and $R^{53}$ is a direct bond or a divalent aliphatic hydrocarbon group having a carbon number of 1 to 25, in which a part of carbon atoms may be substituted with a heteroatom, the other represents an alkyl group having a carbon number of 1 to 25, in which a part of carbon atoms may be substituted with a heteroatom, or a benzyl group, and each of $R^{52}$, $R^{54}$ and $R^{55}$ independently represents a hydrogen atom, a halogen atom, a cyano group, a nitro group, an alkyl group having a carbon number of 1 to 25, in which a part of carbon atoms may be substituted with a heteroatom, a phenyl group, a phenoxy group, a benzyl group, an N-alkylcarbamoyl group or an N-alkylsulfamoyl group, and in the case where any one of $R^{52}$, $R^{54}$ and $R^{55}$ is a direct bond or a divalent aliphatic hydrocarbon group having a carbon number of 1 to 25, in which a part of carbon atoms may be substituted with a heteroatom, each of other two members independently represents a hydrogen atom, a halogen atom, a cyano group, a nitro group, an alkyl group having a carbon number of 1 to 25, in which a part of carbon atoms may be substituted with a heteroatom, a phenyl group, a phenoxy group, a benzyl group, an N-alkylcarbamoyl group or an N-alkylsulfamoyl group, and each of $R^{51}$ and $R^{53}$ independently represents an alkyl group having a carbon number of 1 to 25, in which a part of carbon atoms may be substituted with a heteroatom, or a benzyl group;

the total number of carbon atoms contained in $R^{41}$ to $R^{44}$ in formula (18) is 20 or more, the total number of carbon atoms contained in $R^{45}$ to $R^{50}$ in formula (19) is 15 or more, and the total number of carbon atoms contained in $R^{51}$ to $R^{55}$ in formula (20) is 17 or more; and $R^{41}$ to $R^{55}$ may combine in the same compound to form a ring).

Incidentally, the groups represented by formulae (18) to (20) correspond to the onium moiety of the onium salts represented by formulae (1) to (3).

That is, out of $R^{42}$ to $R^{55}$ in formulae (18) to (20), $R^x$ (x represents any one of 42 to 55) not bonded to —CO— of —CO—$R^{35}$ has the same meaning, out of $R^1$ to $R^{15}$ in formulae (1) to (3), as the group except for —Y—CO—O—Z or —Y—O—CO—Z, and preferable groups are also the same.

On the other hand, out of $R^{42}$ to $R^{55}$ in formulae (18) to (20), $R^y$ (y represents any one of 42 to 55) and $R^{41}$ bonded to —CO— of —CO—$R^{35}$ have the same meaning as —Y— in formulae (1) to (3), and preferable groups are also the same.

The compound β includes a compound where in formula (13) to (15) or (32), one or more -OG groups are substituted with a group represented by the following formula (16) or (17) and one or more -OG groups may be substituted with a group represented by the following formula (33):

[Chem. 22]

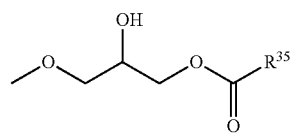
(16)

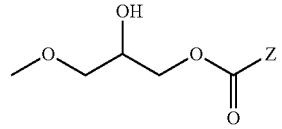
(17)

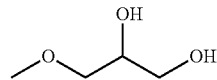
(33)

(in formula (16), $R^{35}$ represents a group represented by any one of formulae (18) to (20); and in formula (17), Z represents a monovalent aliphatic hydrocarbon group having a carbon number of 1 to 25, in which a part of carbon atoms may be substituted with a heteroatom, or a monovalent aromatic hydrocarbon group having a carbon number of 4 to 25, which may have a substituent).

Here, Z has the same meaning as Z in formulae (1) to (3).

The epoxy composition of the present invention includes, for example, a composition containing an epoxy compound α represented by the following structural formula (21) (hereinafter, sometimes referred to as "compound (21)"):

[Chem. 23]

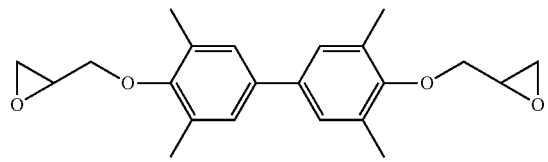

(21)

and a compound β represented by the following formula (22) (hereinafter, sometimes referred to as "compound (22)") or a compound γ represented by the following formula (23) (hereinafter, sometimes referred to as "compound (23)"):

[Chem. 24]

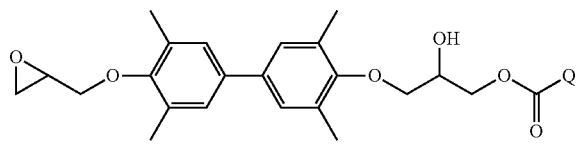

(22)

In formula (22), Q represents $R^{35}$ or —Z in formula (16) or (17). Incidentally, the compound β may be a compound where the glycidyl ether group of the compound represented by formula (22) is substituted with a group represented by formula (33). Furthermore, the epoxy composition may contain a compound where either one or both of glycidyl ether groups of a compound represented by structural formula (21) are ring-opened and changed to a group represented by formula (33).

[Chem. 24]

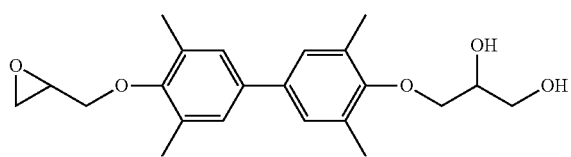

(23)

The amount of the compound β (ester form) produced differs depending on the compound structure, reaction conditions and after-treatment conditions but is usually 0.05 mol % or more, and 10 mol % or less, preferably 5 mol % or less, based on the compound α.

The amount of the compound γ (diol form) produced differs depending on the compound structure, reaction conditions and after-treatment conditions but is usually 0.05 mol % or more, and 10 mol % or less, based on the compound α.

The content of such a compound may be reduced in the above-described after-treatment or purification step, but a small amount of the compound remains in the epoxy compound α.

If the amount produced is smaller than the lower limit above, the adhesiveness of an epoxy resin obtained from the epoxy composition may be reduced, whereas if the amount produced exceeds the upper limit above, the number of reaction points at the time of polymerization of the epoxy composition is small, which may lead to reduction in the productivity of an epoxy resin.

In the present invention, the abundance ratio of the compound β to the compound α may be determined by NMR.

Specifically, the abundance ratio can be determined by comparing the integrated value of proton peaks that are easy to specify and integrate, with the integrated value of peaks of the epoxy compound α. For example, in the case of the ester compound β, the abundance ratio can be determined by comparing the integrated value of proton peaks derived from an alcohol or carboxylic acid forming the ester, with the integrated value of peaks of the epoxy compound α.

Also, the abundance ratio of the compound γ to the compound α can be determined by LC (liquid chromatograph).

Specifically, the LC area ratio of the compound α and the compound γ determined by LC analysis is corrected by taking into account the difference factor between the compound α and the compound γ, that is, the difference in the UV absorption amount, and is thereby converted to a weight ratio or a molar ratio, and the abundance ratio can be determined therefrom.

Incidentally, when the LC analysis is not easy for the reason that exact measurement is difficult because of weak UV absorption of the compound α or compound γ or exact measurement at the same UV wavelength is difficult, the area ratio may be determined by GC (gas chromatograph) analysis. Specifically, the GC area ratio of the compound α and the compound γ determined by GC analysis is corrected by taking into account the difference in the factor of the compound α and the compound γ, that is, the difference in the sensitivity, and thus converted to a weight ratio or a molar ratio, whereby the abundance ratio can be determined.

The compound β has one or more hydroxyl groups obtained by ring opening resulting from addition of one or more epoxy groups to a carboxylic acid. The hydroxyl group contained in an epoxy compound is known to contribute to adhesiveness of an epoxy resin. In an epoxy compound produced by an epichlorohydrin method, a hydroxyl group is contained in a ratio of around 10% and is known to contribute to the adhesiveness. The conventional epoxidation reaction using an onium salt cannot produce a compound corresponding to the compound β and therefore, the content of a hydroxyl group-containing component in the obtained epoxy composition is very small, leaving the fear of insufficient adhesiveness. The epoxy composition obtained by the production method of the present invention contains a given amount of the compound β and therefore, is excellent in terms of lack of the fear above.

<Production Method of Epoxy Resin>

An epoxy resin can be produced by polymerizing the epoxy compound obtained by the production method of the present invention or the epoxy composition of the present invention. The polymerization reaction may be performed by applying a known method and specifically, can be performed, for example, by the method described in JP-A-2007-246819.

<Epoxy Resin>

The high-purity epoxy resin obtained by the method of the present invention can be used in the fields of electronic material, optical material, adhesive, building, etc. Use of the resin makes it possible to avoid corrosion or short circuit occurring due to impurities when used as an electronic component material such as semiconductor sealing material, printed wiring board, build-up wiring board and solder resist, or reduce or avoid the deterioration of coloration when used as an optical material such as sealant of a lighting unit.

Incidentally, the catalyst composition for an epoxidation reaction of the present invention can be utilized also as an oxidant for an oxidation reaction other than an epoxidation reaction, preferably at the time of oxidation of an olefin.

EXAMPLES

The present invention is described in greater detail below by referring to Examples, but the present invention should not be construed as being limited to these Examples.

<$^1$H-NMR Analysis Conditions>
Apparatus: AVANCE400, manufactured by BRUKER, 400 MHz
Solvent: deuterium chloroform containing 0.03 vol % tetramethylsilane
Cumulated number: 128 times
The date in Examples show the δ value in $^1$H-NMR (400 MHz, CDCl$_3$).
Also, the underline in the NMR date described in Examples indicates the proton position identified.

<LC Analysis Conditions>
LC Apparatus: SPD-10Avp, manufactured by Shimadzu Corporation
Temperature: 35° C.
Column: Mightysil RP-18GP aqua 150-4.6 (5 μm) (produced by Kanto Chemical Co., Inc.)
(The following conditions are designated as Analysis Condition 1 and unless otherwise indicated, LC analysis was performed under this condition.)
Detector: UV 280 nm
Eluent: acetonitrile/aqueous 0.1% trifluoroacetic acid solution=90/10 (vol %)
Flow rate: 0.5 ml/min
(The following conditions are designated as Analysis Condition 2.)
Detector: UV 254 nm
Eluent: acetonitrile/aqueous 0.1% trifluoroacetic acid solution 60/40→100/0 (vol %), 20 minutes, and thereafter, kept at 100/0 (vol %) for 10 minutes
Flow rate: 0.5 ml/min <LC-Mass Analysis Conditions>
LC Apparatus: Waters Acquity
Temperature: 40° C.
Column: UPLC BEH C$_{18}$ 2.1×100 mm (1.7 μm)
Eluent: acetonitrile/aqueous 20 mM ammonium acetate solution=50/50 (vol %)→100/0 in 10 min, kept at 100/0 for 10 min
Flow rate: 0.25 ml/min
MS Apparatus: Waters LCT Premier XE
Ionization method: ESI(+) method <GC Analysis Conditions>
Apparatus: GC-1700, manufactured by Shimadzu Corporation
Column: ZB-5 (30 m×0.25 mmφ, 0.25 μm), manufactured by phenomenex
Detector: hydrogen flame ion detector (FID)
Carrier gas (nitrogen flow rate): 28 ml/min
Column temperature: raised from 100° C. to 300° C. at 10° C./min
INJ Temperature: 250° C.
DET Temperature: 300° C.

<GC/Mass Analysis Conditions>
GC Apparatus: GC-2010, manufactured by Shimadzu Corporation
MS Apparatus: GCMS-QP2010Plus, manufactured by Shimadzu Corporation
Column: DB-5 25 M×0.25 (0.25μ)
Ionization method: EI method and CI method <RI Analysis Conditions>
RI Apparatus: JASCO RI-930, manufactured by JASCO Corporation
Temperature: 35° C.
Column: ODS-3 150-4.6 (5 μm) (manufactured by GL Sciences Inc.
Eluent: acetonitrile
Flow rate: 0.5 ml/min As for the chlorine content (ppm by weight), the combined total chlorine amount of inorganic and organic components was measured by the following method. The sample was burned, absorbed by an absorbing liquid and then measured by ion chromatography. The burning apparatus used was AQF-100 manufactured by Mitsubishi Chemical Corporation, and the ion chromatograph used was DX-500 manufactured by DIONEX. In the ion chromatograph, Ion Pac AS12A manufactured by DIONEX was used for the column, and the detection was performed by measuring the electrical conductivity.

The tungsten content (ppm by weight) was measured by the following method. From 0.1 to 0.5 g of the sample was weighted, 2 ml of sulfuric acid was added, and after heating and carbonization, nitric acid and hydrogen peroxide were further added, followed by heating to effect wet digestion. Thereto, 2 ml of aqueous hydrogen peroxide was added and after heating, the mixture was diluted to about 40 ml total with pure water. Furthermore, 2 ml of aqueous hydrogen peroxide was added, and the mixture was diluted to 50 ml with pure water. The resulting solution was analyzed by ICP-AES (ULTIMA 2C, manufactured by HORIBA Jobin Yvon).

The nitrogen content (ppm by weight) was measured by the following method. 8 mg of the sample was burned in an oxygen and argon atmosphere, and the decomposition gas generated was measured by a trace nitrogen analyzer (Model TN-10, manufactured by Mitsubishi Chemical Analytech Co., Ltd.) using a combustion and reduced pressure chemiluminescence method. Also, as the standard sample, aniline dissolved in toluene was used.

The pH of the aqueous phase was measured using pH test papers, Comparator (produced by Johnson Test Papers), for the pH of 1.0 to 3.5 and the pH of 3.6 to 5.1.

(Epoxidation Reaction Raw Material)
As 3,3',5,5-tetramethyl-4,4'-bis(2-propen-1-yloxy)-1,1'-biphenyl (another name: 3,3',5,5'-tetramethylbiphenyl-4,4'-diallyl ether), a compound synthesized by a method in conformity with Example 2 of JP-A-2011-213716 was used. The compound contained 23 ppm of chlorine, and the purity was 99.9% (LC area %, Analysis Condition 1).

As 1,5-cyclooctadiene, a reagent produced by Tokyo Chemical Industry Co., Ltd. was used.

As for the diol compound γ (Compound 23) contained in the epoxy compound (Compound 21), a specimen was synthesized by the method described in Reference Example 1 and using this specimen, the assignment of NMR peaks and the retention time and UV absorption intensity by LC analysis were confirmed and used for the determination of the content of Compound 23 in Compound 21.

As for the ester compound β (Compound 22) in Examples 12, 14, 16, 18, 20, 22, 25 and 26, a specimen was synthesized according to the method described in Reference Example 2, and the NMR analysis of this specimen was performed to confirm the assignment of each peak of NMR. The NMR analysis of Compound 21 was performed based thereon, and the results were used for the determination of the content of Compound 22 in Compound 21. In other Examples, the content of Compound 22 in Compound 21 was determined by analogy with NMR of the compound obtained in Reference Example 2.

Incidentally, the molecular weight of the ester compound β (Compound 22) in Examples 2, 8 and 9 was confirmed by LC-Mass. m/z: 470.3.

For determining the abundance ratio of the compound β or the compound γ to the compound α, the composition obtained by the epoxidation reaction was subjected to LC analysis (in Example 28, GC analysis) to measure the LC area % of each component.

As for the abundance ratio of the compound γ to the compound α, the peak area ratio of the compound γ to the compound α determined by LC analysis (in Example 28, GC analysis) was corrected for the detection sensitivity of each compound and converted to a molar ratio. The detection sensitivity of each compound was determined by previously preparing a specimen of each compound with a purity of 95% or more and calculating the sensitivity from the approximation (purity/100 estimated by molar number×LC area %) of the net molar number of the compound and the LC peak area thereof.

Subsequently, the composition obtained by the epoxidation reaction was subjected to NMR analysis. The abundance ratio of the compound β was determined by comparing the integrated value of proton peaks of the terminal methyl group of a hexanoic acid ester, the tert-butyl group of a tert-butylbenzoic acid ester, etc., which are easy to specify and integrate, with the integrated value of peaks of the epoxy compound α.

The contents of the compounds β and γ are expressed by the abundance ratio to the epoxy compound α, that is, the molar ratio (mol %) based on the epoxy compound α that is taken as 100.

In Examples, in the process of synthesizing (21) by an epoxidation reaction, a slight amount of a compound (a compound of m/z 370.2 in LC-Mass) considered to result from aldehyde isomerization and subsequent oxidation of an epoxy ring by heat or an acid during the reaction is produced in addition to the compounds β and γ. Both of the compound above and the compound γ have higher polarity than the epoxy compound α (21) and give a faster retention time than the compound α (21) in LC analysis. In Examples, these compounds giving a faster retention time than the epoxy compound α (21) are sometimes collectively referred to as "polar compound".

Example 1

Synthesis of Onium Salt [1]

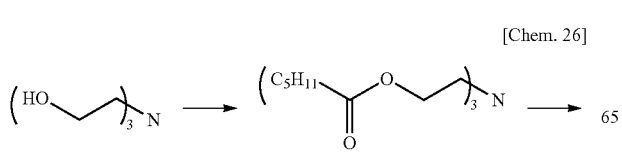

[Chem. 26]

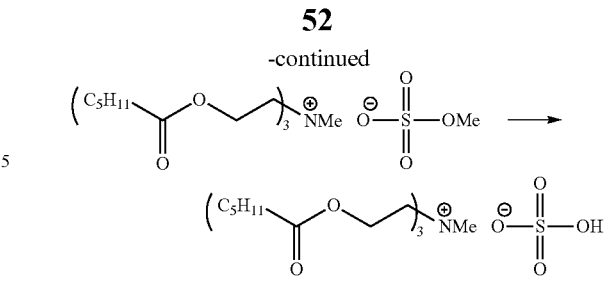

To a mixed solution containing 5.0 g (27 mmol) of triethanolamine hydrochloride, 200 ml of toluene and 10.9 g (4 times mol/substrate) of triethylamine, 10.8 g (3.0 times mol/substrate) of hexanoic acid chloride was added dropwise under ice-water cooling. After the reaction with stirring at room temperature for 1 day, the reaction solution was washed twice with water, i.e., with 150 ml and then with 100 ml, and then concentrated to obtain 9.8 g of crude triethanolamine trihexanoate.

A 7.8 g portion of the crude triethanolamine trihexanoate obtained by the method above was subjected to column purification (200 g of silica gel 60N, developing system: hexane/ethyl acetate=4/1) to obtain 1.63 g of triethanolamine trihexanoat with a purity of 91.2% (GC area %). M+H$^+$: 444.3 (GC-Mass).

The NMR data of the triethanolamine trihexanoate were as follows.

0.90 (9H, t, —CH3), 1.30 (12H, m, CH3-CH2-CH2-), 1.61 (6H, m,—CH2-CH2-CO), 2.30 (6H, t, J=7.56,— CH2-CH2-CO), 2.83 (6H, t, J=6.08, N—CH2-), 4.12 (6H, t, J=6.08, —CH2-O—CO—).

4 ml of toluene, 0.46 g (1.0 times mol/substrate) of dimethyl sulfate and 0.51 g (1.0 times mol/substrate) of potassium carbonate were added to 1.63 g of triethanolamine trihexanoate above and reacted at 80° C. for 5.5 hours. After confirming the conversion of the raw material by the disappearance of the peak attributable to the ethylene moiety of the triethanolamine trihexanoate in NMR analysis, the reaction solution was washed with 5 ml of water, washed three times with 5 ml of 20% sulfuric acid solution, further washed with 5 ml of water and then concentrated to obtain 2.1 g of crude N-methyl-N,N,N-tri[2-(pentylcarbonyloxy) ethyl]ammonium hydrogen sulfate. m/z: 458.3 (LC-Mass) and purity: 75% (RI). This product was used without purification in the epoxidation reaction.

Incidentally, in the following, "N-methyl-N,N,N-tri[2-(pentylcarbonyloxy)ethyl]ammonium hydrogen sulfate" is sometimes referred to as "Onium Salt [1]".

The NMR measurement data of Onium Salt [1] are as follows. N-Methyl-N,N,N-tri[2-(pentylcarbonyloxy)ethyl] ammonium hydrogen sulfate 0.90 (9H, t, —CH3), 1.31 (12H, m, CH3-CH2-CH21), 1.61 (6H, m-CH2-CH2-CO), 2.33 (6H, t, —CH2-CO), 3.38 (3H, s, N—CH3), 3.92 (6H, br, N—CH2-), 4.60 (6H, br, —CH2-O—CO—), 5, 78 (1H, br, HO—SO2).

Example 2

Epoxidation Reaction Using Onium Salt [1]

[Chem. 27]

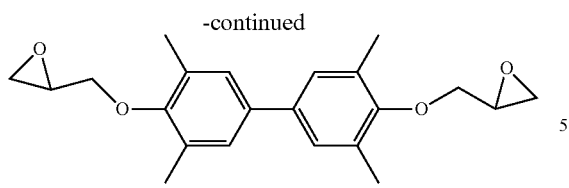

A mixed solution containing 5.0 g (15.5 mmol) of 3,3',5,5-tetramethyl-4,4'-bis(2-propen-1-yloxy)-1,1'-biphenyl, 512 mg (10% mol/substrate) of sodium tungstate dihydrate, 1.97 ml (11% mol/substrate) of an aqueous 8.5% (weight/volume) phosphoric acid solution, 432 mg (5% mol/substrate) of crude N-methyl-N,N,N-tri[2-(pentylcarbonyloxy)ethyl]ammonium hydrogen sulfate, and 3 ml of toluene was heated at 65° C. Under a nitrogen stream, the solution above was added with 0.5 ml (0.5 times mol/substrate) of 45% hydrogen peroxide 6 times every hour and further held at 65 to 68° C. for 7 hours, thereby performing the reaction for a total of 12 hours. It was confirmed by the LC analysis above that 3,3',5,5'-tetramethylbiphenyl-4,4'-diglycidyl ether was produced in a reaction yield of 81% (LC area %).

In addition, 7.0% of 3,3',5,5'-tetramethylbiphenyl-4,4'-monoallyl ether monoglycidyl ether (hereinafter, this compound is sometimes referred to as a monoepoxy compound) as a reaction intermediate, and 9.5% of a polar compound containing the above-described diol compound γ (both are LC area %) were produced.

Here, the "LC area" indicates the peak area of the target compound of analysis, which is obtained by liquid chromatograph (LC) analysis, and "LC area %" indicates the ratio of the peak area of the target compound to the peak area of the total amount of the composition.

After the completion of reaction, 7.5 ml of toluene was additionally added and then, the aqueous phase was separated, washed twice with 5 ml of water and washed in sequence with 5 ml of an aqueous 5% sodium thiosulfate solution and with 5 ml of water. Furthermore, 10 ml of an aqueous 1N sodium hydroxide solution was added and after stirring for 1 hour, the aqueous phase was discharged. The toluene phase was analyzed by NMR, and it was confirmed by the disappearance of the peak attributable to the ethylene moiety of N-methyl-N,N,N-tri[2-(pentylcarbonyloxy)ethyl] ammonium hydrogen sulfate that Onium Salt [1] was hydrolyzed. Washing with the same aqueous sodium hydroxide solution and NMR analysis were repeated three times, and the resulting solution was washed with 10 ml of water. The obtained toluene phase was concentrated to obtain 3.8 g of 3,3',5,5'-tetramethylbiphenyl-4,4'-diglycidyl ether (Compound 21) as a crude crystal. The purity was 86.4%, and the yield was 60%. This crud crystal contained 2.7 mol % of the ester compound β (Compound 22) and 5.2 mol % of the diol compound γ (Compound 23).

The NMR data of the compound before and after the reaction were as follows. 3,3',5,5-Tetramethyl-4,4'-bis(2-propen-1-yloxy)-1,1'-biphenyl 2.32 (12H, s, —CH3), 4.34 (4H, dt, O—CH2-), 5.27 (2H, ddd, —CH=CH2), 5.44 (2H, ddd, —CH=CH2), 6.13 (2H, m,—CH=CH2), 7.18 (4H, s, —C6H2 (Me)2-). 3,3',5,5'-Tetramethylbiphenyl-4,4'-diglycidyl ether (Compound 21)

2.34 (12H, s, —CH3), 2.75 (2H, dd, —CH2-), 2.90 (2H, dd, —CH2-), 3.38 (2H, m, —CH—), 3.73 (2H, dd, —CH2-), 4.07 (2H, dd, —CH2-), 7.18 (4H, s, —C6H2 (Me)2-).

The contents of chlorine, tungsten and nitrogen in the compound were analyzed by the methods described above. The results are shown in Table 1.

Example 3

Synthesis of Onium Salt [2]

[Chem. 28]

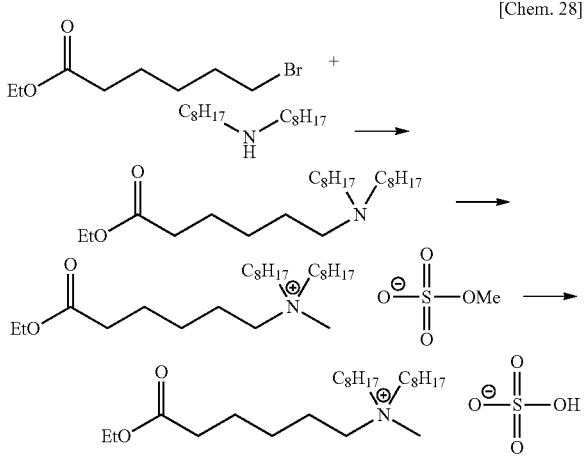

A mixed solution containing 0.92 g (4.1 mmol) of ethyl bromohexanoate, 1.0 g (1 times mol/substrate) of dioctylamine, 5 ml of ethanol and 0.57 g (1 times mol/substrate) of potassium carbonate was relaxed for 10 hours. After additionally adding 0.46 g of ethyl bromohexanoate and 0.29 g of potassium carbonate and relaxing the mixed solution for another 5 hours, 0.25 g of dioctylamine was additionally added, and the mixed solution was relaxed for 12 hours. Disappearance of ethyl bromohexanoate and dioctylamine was confirmed by NMR analysis and thereafter, 0.52 g (1 times mol/substrate) of dimethyl sulfate and 0.57 g (1 times mol/substrate) of potassium carbonate were added and reacted at 60° C. for 2 hours. Subsequently, 0.52 g of dimethyl sulfate and 0.57 g of potassium carbonate were additionally added and reacted at 60° C. for another 2 hours, and furthermore, 0.18 g of dimethyl sulfate and 0.15 g of potassium carbonate were additionally added and reacted at 60° C. for 2 hours. Disappearance of N-(6-ethoxy-6-oxohexyl)-N,N-dioctylamine as a reaction intermediate was confirmed by NMR analysis and thereafter, the insoluble matter was separated by filtration and concentrated to obtain 2.39 g of N-(6-ethoxy-6-oxohexyl)-N-methyl-N,N-dioctylammonium monomethyl sulfate. Yield: 91%.

1.0 g of N-(6-ethoxy-6-oxohexyl)-N-methyl-N,N-dioctylammonium monomethyl sulfate obtained by the method above was dissolved in 2 ml of toluene, and 1 ml of 20% sulfuric acid solution was added, followed by stirring at room temperature for 20 minutes. After discharging the aqueous phase, 1 ml of 20% sulfuric acid solution was again added, followed by stirring at room temperature for 20 minutes. After discharging the aqueous phase, 1 ml of water was added, followed by stirring at room temperature for 20 minutes, and the aqueous phase was discharged. The residue was concentrated to obtain 1.0 g of N-(6-ethoxy-6-oxohexyl)-N-methyl-N,N-dioctylammonium hydrogen sulfate (hereinafter, Onium Salt [2]). This product was used without purification in the epoxidation reaction.

The NMR data of Onium Salt [2] obtained are as follows.

N-(6-Ethoxy-6-oxohexyl)-N-methyl-N,N-dioctylammonium hydrogen sulfate 0.90 (6H, m, —CH3), 1.15-1.5 (25H, m, —CH2—+—CH3), 1.5-1.8 (8H, m, —CH2-), 2.3-2.4 (2H, m, —CH2-CO—), 3.23 (3H, s, N—CH3), 3.2-3.4 (6H, m, N—CH2-), 4.12 (2H, dd, —CH2-O—CO—), 5.66 (1H, br, HO—SO2).

Example 4

Epoxidation Reaction Using Onium Salt [2]

The reaction was performed in the same manner by the same method as in Example 2 by using, as the ammonium salt, N-(6-ethoxy-6-oxohexyl)-N-methyl-N,N-dioctylammonium hydrogen sulfate (5% mol/substrate) in place of N-methyl-N,N,N-tri[2-(pentylcarbonyloxy)ethyl]ammonium hydrogen sulfate. The reaction yield: 80% (LC area %). The obtained crude crystal of Compound 21 contained 1.1 mol % of the ester compound β (Compound 22). The content of tungsten in the compound was measured by the method described above. The measurement results are shown in Table 1.

Example 5

Synthesis of Onium Salt [3]

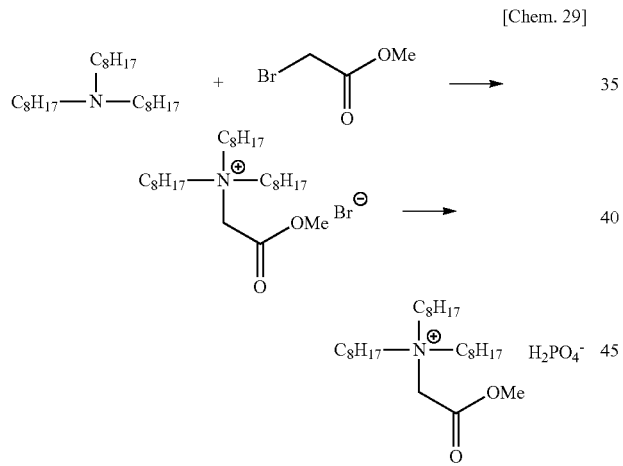

[Chem. 29]

A mixed solution containing 5.0 g (14.1 mol) of trioctylamine, 25 ml of toluene and 1.92 g (1.0 times mol/substrate) of methyl bromoacetate was heated at 40° C. for 4 hours. After confirming disappearance of methyl bromoacetate by NMR analysis, the reaction solution was washed twice with 25 ml of an aqueous 8.5% phosphoric acid solution to obtain a toluene solution of 0.57 mol/L N,N,N-trioctyl-N-(2-methoxy-2-oxoethyl)ammonium phosphate (hereinafter, Onium Salt [3]). This product was used without purification in the epoxidation reaction.

The NMR data of Onium Salt [3] obtained are as follows.

N,N,N-Trioctyl-N-(2-methoxy-2-oxoethyl)ammonium phosphate 0.88 (9H, t, —CH3), 1.20-1.40 (30H, m, —CH2-), 1.76 (6H, m, —CH2-), 3.60-3.67 (6H, m, —CH2-), 3.81 (3H, s, —CH3), 4.85 (2H, s-N—CH2-).

Example 6

Epoxidation Reaction Using Onium Salt [3]

The reaction was performed in the same manner by the same method as in Example 2 by using, as the ammonium salt, N,N,N-trioctyl-N-(2-methoxy-2-oxoethypammonium phosphate (5% mol/substrate). The reaction stopped proceeding 4 hours after the initiation of the reaction, and the reaction yield was 23% (LC area %). The NMR analysis of the reaction mixture was performed by the same method as in Example 2, as a result, disappearance of the 2-methoxy-2-oxoethyl moiety of the N,N,N-trioctyl-N-(2-methoxy-2-oxoethyl)ammonium salt was confirmed, suggesting that decomposition of Onium Salt [3] occurred.

Comparative Example 1

Epoxidation Reaction Using Methyltrioctylammonium Hydrogen sulfate 150.0 g (0.47 mol) of 3,3',5,5-tetramethyl-4,4'-bis(2-propen-1-yloxy)-1,1'-biphenyl was reacted by the same method as in Example 2 by using methyltrioctylammonium hydrogen sulfate (5% mol/substrate) as the ammonium salt. The reaction yield of 3,3',5,5'-tetramethylbiphenyl-4,4'-diglycidyl ether was 84% (LC area %). After the completion of reaction, the reaction solution was treated by the same method to obtain 147 g of 3,3',5,5'-tetramethylbiphenyl-4,4'-diglycidyl ether as a crude crystal. Yield: 76% and purity: 91.2% (LC area %, LC Analysis Condition 2). This crude crystal contained methyltrioctylammonium salt, and the content thereof was estimated by NMR analysis to be 6 mol % (expressed by the ratio based on 3,3',5,5'-tetramethylbiphenyl-4,4'-diglycidyl ether that is taken as 100). The residual amount of each of nitrogen and tungsten was measured by inorganic analysis. The analysis results are shown in Table 1.

Comparative Example 2

After adding 10.5 ml of methanol to 1.5 g of 3,3',5,5'-tetramethylbiphenyl-4,4'-diglycidyl ether obtained by the method of Comparative Example 1, the mixture was stirred and crystalized at 50° C. for 2 hours and cooled to 6° C., and 0.89 g of a crystal was collected by filtration. Yield: 62%. Purity: 95.2% (LC area %, LC Analysis Condition 2). This crystal contained methyltrioctylammonium salt, and the content thereof was 1.75 mol % (the same NMR analysis as above; corresponding to a residual nitrogen amount of 690 ppm).

Example 7

Synthesis Method of Onium Salt [1'] (with the Counter Cation being Monomethylsulfuric Acid A mixed solution containing 20.0 g (207 mmol) of triethanolamine hydrochloride, 60 ml of octane, 43.3 g (3.0 times mol/substrate) of hexanoic acid and 5.28 g of sulfuric acid was heated in an oil bath at 135° C. and reacted for 61 hours while distilling off the occurring water. After allowing the reaction system to cool, 200 ml of ethyl acetate and 400 ml of a saturated sodium bicarbonate solution were added, and the mixture was stirred. Thereafter, the aqueous phase was discharged, and the organic phase was washed with 100 ml of water. The obtained compound was a mixture of hexanoic acid monoester, diester and triester, and the esterification ratio (the proportion of the esterified hydroxyl group determined from the H integration ratio in NMR analysis) was 79%.

The crude triethanolamine trihexanoate obtained by the method above was subjected to column purification (silica gel 60N, 300 g, developing system: hexane/ethyl acetate=10/1→>5/1) to obtain 15.6 g of triethanolamine trihexanoate with a purity of 98.3% (GC). The yield was 33%.

To 0.34 g (0.78 mmol) of triethanolamine trihexanoate obtained above, 1.1 ml of toluene and 0.12 g (1.2 times mol/triethanolamine trihexanoate) of dimethyl sulfate were added and reacted at 90° C. for 2 hours. As a result, N-methyl-N,N,N-tri[2-(pentylcarbonyloxy)ethyl]ammonium monomethyl sulfate (hereinafter, referred to as Onium Salt [1']) in an yield of 84% (molar ratio determined from the H integration degree of ethylene chain in NMR analysis). This reaction solution was used directly without purification in the epoxidation reaction.

Example 8

Epoxidation Reaction Using Onium Salt [1']

A solution prepared by dissolving 5.0 g (15.5 mmol) of 3,3',5,5-tetramethyl-4,4'-bis(2-propen-1-yloxy)-1,1'-biphenyl in 6.3 ml of toluene was washed with 15 ml of an aqueous solution containing 1 wt % of anhydrous sodium sulfate and 1 vol % of acetic acid, then washed with a mixed solution containing 0.23 ml of an aqueous 3 wt % sodium pyrophosphate solution, 0.06 ml of a 10 wt % ethylenediaminetetraacetic acid solution and 15 ml of water, and further washed with 10 ml of water, and to the obtained toluene layer, 511 mg (10% mol/substrate) of sodium tungstate dihydrate, 0.9 ml (5% mol/substrate) of an aqueous 8.5% (weight/volume) phosphoric acid solution, 2 ml of water and a toluene solution of N-methyl-N,N,N-tri[2-(pentylcarbonyloxy)ethyl]ammonium monomethyl sulfate obtained above were added, followed by stirring. Furthermore, an aqueous phosphoric acid solution was added to the resulting mixed solution, whereby the pH of the aqueous phase of the mixed solution was adjusted to 4.8. The amount of the aqueous phosphoric acid solution added here was 0.5 ml (3% mol/substrate). The mixed solution was heated at 65° C. and thereafter, under a nitrogen stream, added with 0.5 ml (0.5 times mol/substrate) of 45% hydrogen peroxide a total of 5 times, that is, at the initiation of reaction and after 1 hour, 2 hours, 3 hours and 6 hours therefrom, at an inner temperature of 65 to 68° C. When the reaction was started, an aqueous 1N sodium hydroxide solution was added in an amount of 0.4 ml after 1.5 hours, 0.1 ml after 4.5 hours, and 0.1 ml after 6.5 hours, to adjust the pH of the aqueous solution to a range of 3.0 to 3.5. The reaction was performed for a total of 8 hours at an inner temperature of 65 to 68° C., and it was confirmed by the LC analysis above that 3,3',5,5'-tetramethylbiphenyl-4,4'-diglycidyl ether was produced in a reaction yield of 82% (LC area %). In addition, production of 11% (LC area %) of a monoepoxy compound as a reaction intermediate and 6% (LC area %) of a polar compound was confirmed.

After the completion of reaction, 7.5 ml of toluene was additionally added and then, the aqueous phase was separated, washed three times with 5 ml of water. Furthermore, 10 ml of an aqueous 1N sodium hydroxide solution was added and after stirring for 1 hour, the aqueous phase was discharged. Washing with the same aqueous sodium hydroxide solution was repeated three times, and the resulting solution was washed with 10 ml of water. The obtained organic phase was concentrated to obtain 4.5 g of 3,3',5,5'-tetramethylbiphenyl-4,4'-diglycidyl ether (Compound 21) with a purity of 83% (LC area %) as a crystal. The yield was 69%. This crystal contained 2.4 mol % of the ester compound β (Compound 22) and 3.5 mol % of the diol compound γ (Compound 23). The contents of chlorine, tungsten and nitrogen in the compound were analyzed by the methods described above. The measurement results are shown in Table 1.

Example 9

After adding 15 ml of methanol to 2.0 g of 3,3',5,5'-tetramethylbiphenyl-4,4'-diglycidyl ether obtained by the method above, the mixture was stirred and crystalized at 50° C. for 1 hour to obtain 1.8 g of a crystal of 3,3',5,5'-tetramethylbiphenyl-4,4'-diglycidyl ether (Compound 21) with a purity of 91% (LC area %). Recovery percentage: 98%. This crystal contained 0.3 mol % of the ester compound β (Compound 22).

Example 10

Synthesis of Onium Salt [4]

The reaction was performed by the same method as in Example 8 without performing the addition of an aqueous sodium hydroxide solution during the reaction. It was confirmed that 3,3',5,5'-tetramethylbiphenyl-4,4'-diglycidyl ether was produced in a reaction yield of 77% (LC area %). In addition, production of 9% (LC area %) of a monoepoxy compound as a reaction intermediate and 12% (LC area %) of the compound γ resulting from ring opening of an epoxy ring due to an acid was confirmed.

Example 11

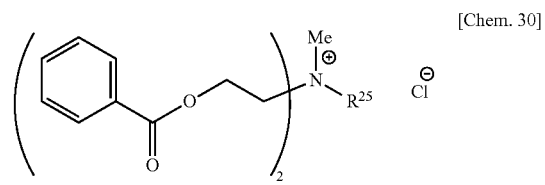

[Chem. 30]

(In the structural formula above, $R^{25}$ represents a C8-C18 alkyl group.)

While heating a mixed solution containing 12.0 g of Ethoquad C/12 produced by Lion Akzo Corporation (N-alkyl(C8-C-18)-N,N-bis(2-hydroxyethyl)-N-methylammonium chloride; containing about 20% of isopropanol) and 200 ml of toluene, 50 ml of a mixed solution of toluene and isopropanol was distilled off. Thereafter, 5.0 g of triethylamine was added and after adding 6.7 g of benzoyl chloride at an inner temperature of 60 to 80° C., the reaction was performed at an inner temperature of 65° C. for 30 minutes and at 80° C. for 2 hours. As for the change over time of the reaction system, about 0.1 ml of the reaction mixture was dissolved in 1 ml of methanol, the unreacted benzoyl chloride was converted to benzoic acid methyl eater, and LC analysis was performed under Analysis Condition 2. Triethylamine and benzoyl chloride were gradually added at 80° C., and the point where consumption of benzoyl chloride was stopped was designated as the end point. The amounts of the additionally added triethylamine and benzoyl chloride were 4.8 g and 3.6 g, respectively.

After the completion of reaction, 100 ml of toluene and 100 ml of water were added to the reaction system and after stirring, the aqueous phase turned white turbid was discharged. When the aqueous phase was left standing still, an organic phase was liberated and therefore, this organic phase was combined with the separated organic phase and washed with 100 ml of water to obtain 13 g of a benzoic acid ester form of Ethoquad C/12, which is N-alkyl-N,N-bis[2-(phenylcarbonyloxy)ethyl]-N-methylammonium chloride. The purity was 82% (LC area %, LC Analysis Condition 2), and the product contained 11% (LC area %) of benzoic acid. The carbon number of the alkyl chain was estimated to be about 14 on average from the H integration value in NMR (hereinafter, referred to as Onium Salt [4]).

The NMR data of Onium Salt [4] obtained are as follows.
N-Alkyl-N,N-bis[2-(phenylcarbonyloxy)ethyl]-N-methyl-ammonium chloride 0.88 (3H, —CH3), 1.0-1.4 (about 20H, br, —CH2-), 1.76 (2H, m, —CH2-), 2.00 (2H, m, —CH2-), 3.63 (3H, s, N—CH3), 3.63 (2H, m-CH2-), 4.38 (4H, m, N—CH2-), 4.91 (4H, m, —CH2-CO), 7.42 (4H, dd, -Ph), 7.56 (2H, dd, -Ph), 8.00 (4H, d, -Ph).

Example 12

Epoxidation Reaction Using Onium Salt [4]

A solution prepared by dissolving 10.0 g (31.0 mmol) of 3,3',5,5-tetramethyl-4,4'-bis(2-propen-1-yloxy)-1,1'-biphenyl in 10 ml of toluene was washed with 30 ml of an aqueous solution containing 1 wt % of anhydrous sodium sulfate and 1 vol % of acetic acid, then washed with a mixed solution containing 0.26 ml of an aqueous 3 wt % sodium pyrophosphate solution, 0.12 ml of a 10% ethylenediaminetetraacetic acid solution and 30 ml of water, and further washed with 30 ml of water, and to the obtained organic phase, 1.02 g (10% mol/substrate) of sodium tungstate dihydrate, 1.79 ml (5% mol/substrate) of an aqueous 8.5% (weight/volume) phosphoric acid solution, 2 ml of water and 1.0 g of the benzoic acid ester form of Ethoquad C/12 obtained above were added, followed by stirring. Under a nitrogen stream, 0.5 ml (0.5 times mol/substrate) of 45% hydrogen peroxide was added at an inner temperature of 65 to 68° C., and thereafter, 1.79 ml (5% mol/substrate) of an aqueous phosphoric acid solution was further added to the resulting mixed solution, whereby the pH of the aqueous solution of the mixed solution was adjusted to 3.5. While heating the mixed solution at 65° C., 0.5 ml (0.5 times mol/substrate) of 45% hydrogen peroxide was added a total of 5 times, that is, after 1 hour, 2 hours, 3 hours and 6 hours therefrom, and 0.1 g of the benzoic acid ester form of Ethoquad C/12 was additionally added after 8 hours. The reaction was performed for a total of 12 hours at an inner temperature of 65 to 68° C., and it was confirmed by the LC analysis above that 3,3',5,5'-tetramethylbiphenyl-4,4'-diglycidyl ether was produced in a reaction yield of 82% (LC area %). In addition, production of 8% (LC area %) of a monoepoxy compound as a reaction intermediate and 5% (LC area %) of a polar compound was confirmed.

After the completion of reaction, the aqueous phase was discharged, and the residue was washed twice, that is, with 20 ml of water and with 2 ml of saturated brine, further washed twice with 20 ml of water, and then cooled to precipitate the reaction content as a solid. The supernatant water and the toluene mixed solution were discharged by decantation, and the remaining solvent was distilled off by blowing nitrogen, as a result, a solid of the reaction content was obtained.

The obtained solid was added with 20 ml of an aqueous 1N sodium hydroxide solution and after stirring for 1 hour, the aqueous phase was discharged. After repeating the same operation three times, the resulting solution was washed with 2 ml of an aqueous 5% sodium thiosulfate solution and 20 ml of water and further washed with 20 ml of water, and the obtained solid was dried to obtain 8.2 g of 3,3',5,5'-tetramethylbiphenyl-4,4'-diglycidyl ether (Compound 21) with a purity of 94% (LC area %) as a crude crystal (yield: 70%). This crud crystal contained 0.6 mol % of the ester compound β (Compound 22) and 6.8 mol % of the diol compound γ (Compound 23).

The content of tungsten in the compound was analyzed by the method described above. The measurement results are shown in Table 1.

Example 13

Synthesis of Onium Salt [5]

[Chem. 31]

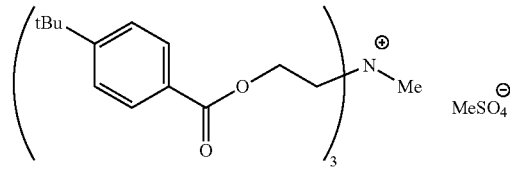

A mixed solution containing 80 g (0.44 mmol) of 4-tert-butylbenzoic acid, 240 ml of toluene and 0.68 g (0.015 times mol/substrate) of triethylamine was heated at 75° C. and thereafter, 64.1 g (1.2 times mol/substrate) of thionyl chloride was added over 1.5 hours. The reaction was performed at 75° C. for another 1.5 hours. After the completion of reaction, 100 ml of toluene was added under atmospheric pressure, 50 ml of toluene was further added under reduced-pressure conditions, and excess thionyl chloride was distilled off to obtain 90.8 g of 4-tert-butylbenzoyl chloride.

To a mixed solution containing 2.0 g (10.8 mmol) of triethanolamine hydrochloride, 20 ml of toluene and 4.36 g (4 times mol/substrate) of triethylamine, 7.0 g (3.0 times mol/substrate) of 4-tert-butylbenzoyl chloride obtained by the method above was added dropwise under ice-water cooling. After the reaction with stirring at 60° C. for 5 hours, 1.42 (1.3 times mol/substrate) of triethylamine and 0.4 g of triethanolamine hydrochloride were additionally added and reacted with stirring at 80° C. for 10 hours. After the completion of reaction, the reaction solution was washed three times with 20 ml of water and then concentrated. The obtained crude triethanolamine trihexanoate was added with 40 ml of hexane for crystallization, and the crystal was collected by filtration to obtain 5.12 g of triethanolamine tri-4-tert-butylbenzoate. Purity: 98.2% (LC Analysis Condition 2) and yield: 63%.

A 0.54 g (0.85 mmol) portion of the triethanolamine tri-4-tert-butylbenzoate obtained by the method above was added with 1.6 ml of toluene and heated at 80° C., and the reaction was performed for 3.5 hours while adding in parts 135 mg (1.2 times mol/substrate) of dimethyl sulfate. Production of N-methyl-N,N,N-tri[2-(4-tert-butylphenylcarbonyloxy)ethyl]ammonium monomethyl sulfate (hereinafter, referred to as Onium Salt [5]) at a conversion ratio of 91% (LC area %, LC Analysis Condition 2) was confirmed. This reaction solution was used directly without purification in the epoxidation reaction.

The NMR data of Onium Salt [5] obtained are as follows.
N-Methyl-N,N,N-tri[2-(4-tert-butylphenylcarbonyloxy)ethyl]ammonium monomethyl sulfate
1.28 (27H, s, t-Bu), 3.58 (3H, s, —CH3), 3.67 (3H, s, CH3OSO2-), 4.26 (6H, br, N—CH2-), 4.92 (6H, br, —CH2-CO), 7.38 (6H, dd, —Ar), 7.88 (6H, dd, —Ar).

Example 14

Epoxidation Reaction Using Onium Salt [5]

5.0 g (15.5 mmol) of 3,3',5,5-tetramethyl-4,4'-bis(2-propen-1-yloxy)-1,1'-biphenyl pretreated by the same method as above, 3.8 ml of toluene, 512 mg (10% mol substrate) of sodium tungstate dihydrate, 1.61 ml (9% mol/substrate) of an aqueous 8.5% (weight/volume) phosphoric acid solution, 3.4 ml of water and a toluene solution of N-methyl-N,N,N-tri[2-(4-tert-butylphenylcarbonyloxy)ethyl]ammonium monomethyl sulfate obtained above were previously added and stirred. This mixed solution was heated at 65° C. and thereafter, under a nitrogen stream, added with 0.5 ml (0.5 times mol/substrate) of 45% hydrogen peroxide a total of 5 times, that is, at the initiation of reaction and after 1 hour, 2 hours, 3 hours and 4 hours therefrom, and the reaction was performed for 7 hours. The pH of the aqueous layer was adjusted to 2.5 by adding 0.5 ml of an aqueous 1N sodium hydroxide solution halfway therethrough. It was confirmed that 3,3',5,5'-tetramethylbiphenyl-4,4'-diglycidyl ether was produced in a reaction yield of 78% (LC area %, Analysis Condition 1). In addition, 8.2% (LC area %) of a monoepoxy compound as a reaction intermediate and 10.7% (LC area %) of a polar compound were produced.

After the completion of reaction, 25 ml of toluene was additionally added, the aqueous layer was discharged, and the residue was washed twice with 10 ml of water and then washed with 12.5 ml of an aqueous 5% sodium thiosulfate solution. Furthermore, 25 ml of an aqueous 1N sodium hydroxide solution was added and after stirring at 25° C. for 15 minutes, the aqueous layer was discharged. Washing with the sodium hydroxide solution was repeated three times at an inner temperature of 35° C. for 30 minutes, and the resulting solution was washed with 25 ml of water. It was confirmed by LC and NMR that N-methyl-N,N,N-tri[2-(4-tert-butylphenylcarbonyloxy)ethyl]ammonium monomethyl was hydrolyzed and disappeared. The obtained organic phase was concentrated to obtain 4.7 g of 3,3',5,5'-tetramethylbiphenyl-4,4'-diglycidyl ether (Compound 21) as a crude crystal. Purity: 89.5% (LC area %, LC Analysis Condition 2) and yield: 77%. This crude crystal contained 4.6 mol % of the ester compound β (Compound 22) and 1.4 mol % of the diol compound γ (Compound 23).

The contents of tungsten and nitrogen in the compound were analyzed by the methods described above. The measurement results are shown in Table 1.

Example 15

Synthesis of Onium Salt [6]

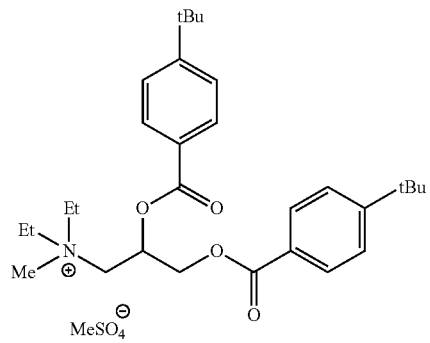

[Chem. 32]

To a mixed solution containing 2.40 g (13.6 mmol) of 3-diethylamino-1,2-propanediol, 20 ml of toluene and 4.13 g (3 times mol/substrate) of triethylamine, 5.8 g (2.2 times mol/substrate) of 4-tert-butylbenzoyl chloride obtained by the method above was added dropwise under ice-water cooling. The reaction was performed with stirring at 60° C. for 3 hours. The reaction yield was 98% (LC area %, LC Analysis Condition 2). After the completion of reaction, the reaction solution was washed three times with 20 ml of water and then concentrated. The obtained crude 3-diethylamino-1,2-propanediol-di-4-tert-butylbenzoate was purified by silica gel column chromatography (silica gel 60N, 200 g, developing system; hexane/ethyl acetate=4/1→2/1) to obtain 5.5 g of 3-diethylamino-1,2-propanediol-di-4-tert-butylbenzoate with a purity of 98% (LC area %). Purity: 98% (LC area %, LC Analysis Condition 2) and yield: 71%.

A 0.16 g (0.30 mmol) portion of the diester obtained by the method above was added with 1 ml of toluene and 51 mg (1.2 times mol/substrate) of dimethyl sulfate and reacted at 80° C. for 2 hours. Production of 2,3-bis(4-tert-butyl-phenyloxy)-N,N-diethyl-N-methyl-1-propane ammonium monomethyl sulfate (hereinafter, referred to as Onium Salt [6]) at a conversion ratio of 99% or more was confirmed by NMR analysis. This reaction solution was used directly without purification in the epoxidation reaction.

The NMR data of Onium Salt [6] obtained were as follows. 2,3-Bis(4-tert-butyl-phenyloxy)-N,N-diethyl-N-methyl-1-propane ammonium monomethyl sulfate
1.37 (18H, s, t-Bu), 1.43 (6H, s, —CH3), 3.26 (3H, s, CH3-N), 3.56 (4H, m, N-CH2-CH3), 3.73 (3H, s, CH3OSO2-), 4.36 (2H, m, —CH2-O—CO), 4.58 (1H, dd, —CH2-N), 4.78 (1H, dd, —CH2-N), 6.03 (1H, m, —CH—), 7.41 (2H, dd, —Ar), 7.46 (2H, dd, —Ar), 7.87 (2H, dd, —Ar), 7.96 (2H, dd, —Ar).

Example 16

Epoxidation Reaction Using Onium Salt [6]

2.0 g (6.2 mmol) of 3,3',5,5-tetramethyl-4,4'-bis(2-propen-1-yloxy)-1,1'-biphenyl pretreated by the same method as above, 1.4 ml of toluene, 204 mg (10% mol/substrate) of sodium tungstate dihydrate, 0.36 ml (5% mol/substrate) of an aqueous 8.5% (weight/volume) phosphoric acid solution, 3.6 ml of water and a toluene solution of 2,3-bis(4-tert-butyl-phenyloxy)-N,N-diethyl-N-methyl-1-propane ammonium monomethyl sulfate obtained above were previously added and stirred. This mixed solution was heated at 65° C. and thereafter, under a nitrogen stream, added with 0.1 ml (0.5 times mol/substrate) of 45% hydrogen peroxide a total of 5 times, that is, at the initiation of reaction and after 1 hour, 2 hours, 3 hours and 6 hours therefrom, at an inner temperature of 65 to 68° C. The reaction was performed for a total of 7 hours at an inner temperature of 65 to 68° C., and it was confirmed by the LC analysis above that 3,3',5,5'-tetramethylbiphenyl-4,4'-diglycidyl ether was produced in a reaction yield of 77% (LC area %, Analysis Condition 1). In addition, 11% (LC area %) of a monoepoxy compound as a reaction intermediate and 8% (LC area %) of a polar compound were produced.

After the completion of reaction, 6 ml of toluene was additionally added, the aqueous layer was discharged, and the organic phase was washed with 4 ml of an aqueous 5 wt % sodium thiosulfate solution. Furthermore, 4 ml of an aqueous 1N sodium hydroxide solution was added and after stirring for 1 hour, the aqueous layer was discharged. After repeating washing with the same aqueous sodium hydroxide solution four times, it was confirmed by LC that 2,3-bis(4-tert-butyl-phenyloxy)-N,N-diethyl-N-methyl-1-propane ammonium monomethyl was hydrolyzed and disappeared. The obtained organic phase was washed with 4 ml of water and then concentrated to obtain 1.9 g of 3,3',5,5'-tetramethylbiphenyl-4,4'-diglycidyl ether (Compound 21) with a purity of 83% (LC area %) as a crude crystal. Yield: 72%. This crude crystal contained 5.0 mol % of the ester compound β (Compound 22) and 5.1 mol % of the diol compound γ (Compound 23).

The contents of tungsten and nitrogen in the compound were analyzed by the methods described above. The measurement results are shown in Table 1.

Example 17

Synthesis of Onium Salt [7]

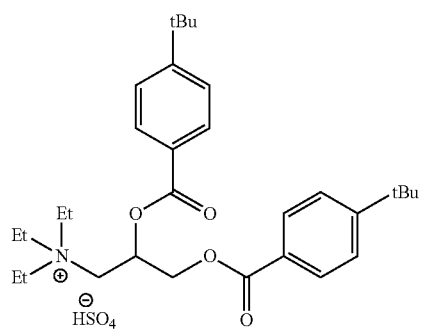

[Chem. 33]

10.3 g (93.2 mol) of 1-chloro-2,3-propanediol and 14.1 g (1.5 times mol/substrate) of triethylamine were heated with stirring at 80° C. for 12 hours, and 10 ml of ethanol was added. After homogenizing the reaction system, hexane was added to obtain 2,3-dihydroxypropyltriethylammonium chloride as a precipitate. The remaining ethanol was azeotropically distilled off by using toluene, and the residue was dried under reduced pressure to obtain 19.4 g of 2,3-dihydroxypropyltriethylammonium chloride. Crude yield: 98%.

A mixed solution containing 3.0 g of crude 2,3-dihydroxypropyltriethylammonium chloride obtained by the method above, 30 ml of toluene and 5.17 g (2.2 times mol/substrate) of triethylamine was heated at 70° C., and 7.4 g (2.2 times mol/substrate) of 4-tert-butylbenzoyl chloride synthesized by the method above was added. The reaction was performed for 16 hours while adding 10 ml of tetrahydrofuran halfway therethrough and additionally adding 2.2 g (1.3 mol/substrate) of triethylamine. After allowing to cool, the precipitated solid in the reaction system was collected by filtration. This solid was dissolved in 50 ml of chloroform and washed twice with 10 ml of water and then, the solvent was distilled off to obtain 4.8 g of 2,3-bis(4-tert-butyl-phenyloxy)-N,N,N-triethyl-1-propane ammonium chloride. Purity: 96% (LC). Yield: 92%.

A 2 g portion of the ammonium chloride obtained by the method above was purified (developing solvent: ethanol) with 100 ml of Diaion HP120 (produced by Mitsubishi Chemical Corporation) and concentrated. The obtained residue was dissolved in 30 ml of ethyl acetate, washed twice with 5 ml of a 10% (v/v) sulfuric acid solution and then concentrated to obtain 1.42 g of 2,3-bis(4-tert-butyl-phenyloxy)-N,N,N-triethyl-1-propane ammonium hydrogen sulfate (hereinafter, referred to as Onium Salt [7]). Purity: 98% (LC area %, LC Analysis Condition 2).

The NMR data of Onium Salt [7] obtained are as follows.
2,3-Bis(4-tert-butyl-phenyloxy)-N,N,N-triethyl-1-propane ammonium hydrogen sulfate
1.32 (18H, s, t-Bu), 1.47 (9H, s, —CH3), 3.59 (6H, m, N—CH2-CH3), 4.29 (1H, m, HSO4), 4.37 (2H, m, —CH2-O—CO), 4.64 (1H, dd, —CH2-N), 4.82 (1H, dd, —CH2-N), 6.00 (1H, m, —CH—), 7.42 (4H, dd, —Ar), 7.90 (4H, dd, —Ar).

Example 18

Epoxidation Reaction Using Onium Salt [7]

5.0 g (15.5 mmol) of 3,3',5,5-tetramethyl-4,4'-bis(2-propen-1-yloxy)-1,1'-biphenyl pretreated by the same method as above, 3.8 ml of toluene, 51.2 mg (10% mol/substrate) of sodium tungstate dihydrate, 1.25 ml (7% mol/substrate) of an aqueous 8.5% (weight/volume) phosphoric acid solution, 3.4 ml of water and 0.46 g (5% mol/substrate) of 2,3-bis(4-tert-butyl-phenyloxy)-N,N,N-triethyl-1-propane ammonium sulfate obtained above were previously added and stirred. This mixed solution was heated at 65° C. and thereafter, under a nitrogen stream, added with 0.5 ml (0.5 times mol/substrate) of 45% hydrogen peroxide a total of 6 times, that is, at the initiation of reaction and after 1 hour, 2 hours, 3 hours, 4 hours and 6 hours therefrom. The reaction was performed for a total of 10 hours, that is, for 4 hours at an inner temperature of 65 to 66° C. and for 6 hours at an inner temperature of 68 to 69° C., and it was confirmed by the LC analysis above that 3,3',5,5'-tetramethylbiphenyl-4,4'-diglycidyl ether was produced in a reaction yield of 82% (LC area %, Analysis Condition 1). In addition, 5.4% (LC area %) of a monoepoxy compound as a reaction intermediate and 10.7% (LC area %) of a polar compound were produced.

After the completion of reaction, 20 ml of toluene was additionally added, the aqueous layer was discharged, and the residue was washed twice with 10 ml of water and then washed with 12.5 ml of an aqueous 5% sodium thiosulfate solution. Furthermore, 25 ml of an aqueous 1N sodium hydroxide solution was added and after stirring at 25° C. for 1 hour, the aqueous layer was discharged. Washing with the aqueous sodium hydroxide solution was repeated three times at an inner temperature of 35° C. for 30 minutes, and it was confirmed by LC and NMR that Onium Salt [7] was hydrolyzed and disappeared and tert-butylberizoic acid as a hydrolysate of Onium Salt [7] did not remain. The obtained organic phase was washed with 25 ml of water and then concentrated to obtain 4.88 g of 3,3',5,5'-tetramethylbiphenyl-4,4'-diglycidyl ether (Compound 21) as a crude crystal. Purity: 87.5% (LC area %, LC Analysis Condition 2). Yield: 78%. This crude crystal contained 4.5 mol % of the ester compound β (Compound 22) and 3.7 mol % of the diol compound γ (Compound 23).

The contents of nitrogen and tungsten in the compound were analyzed by the methods described above. The measurement results are shown in Table 1.

Example 19

Synthesis of Onium Salt [8]

[Chem. 34]

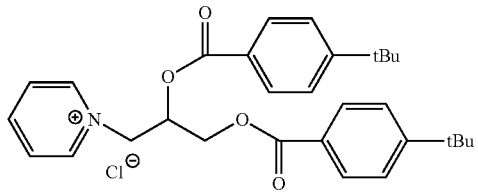

A mixed solution containing 2.00 g (18.1 mmol) of 3-chloro-1,2-propanediol and 4.58 g (2.5 times mol/substrate) of triethylamine was added dropwise to 4-tert-butylbenzoyl chloride synthesized in the same manner as above from 6.45 g (2.0 times mol/substrate) of 4-tert-butylbenzoic acid, 4.3 g (2 times mol/substrate) of thionyl chloride and 20 ml of toluene. The reaction was performed at 50° C. for 7 hours. After the completion of reaction, the reaction solution was washed twice with 10 ml of water and concentrated. The obtained crude 3-chloro-1,2-propanediol-di-4-tert-butylbenzoate was crystallized by adding hexane to obtain 5.0 g of 3-chloro-1,2-propanediol-di-4-tert-butylbenzoate. LC Purity: 98.5% (LC area %, LC Analysis Condition 2) and yield: 64%.

A 1.00 g portion of the 3-chloro-1,2-propanediol-di-4-tert-butyl benzoate. obtained by the method above was added with 5.24 g (30 times mol/substrate) of pyridine and 37 mg (0.1 times mol/substrate) of potassium iodide and reacted with stirring under reflux conditions for 32 hours, whereby 1-[2,3-bis[(4-tert-butylphenylcarbonyloxy)propyl]pyridinium chloride was obtained at a conversion ratio of 98% with a selectivity of 62% (LC area %, LC Condition 2). After distilling off pyridine, 20 ml of hexane was added to the resulting residue to obtain 0.32 g of 1-[2,3-bis[(4-tert-butylphenylcarbonyloxy)propyl]pyridinium chloride (hereinafter, Onium Salt [8]). Purity: 92.9% (LC area %, LC Analysis Condition 2). Yield: 28%.

The NMR data of Onium Salt [8] obtained are as follows.

1-[2,3-Bis[(4-tert-butylphenylcarbonyloxy)propyl] pyridinium chloride 1.32 (18H, d, t-Bu), 4.91 (2H, m, —CH2-O—CO), 5.38 (2H, m, —CH2-N), 5.93 (1H, m, —CH1-), 6.22 (1H, m, —CH2-N), 6.03 (1H, m, —CH—), 7.42 (2H, dd, —Ar), 7.45 (2H, dd, —Ar), 7.82 (2H, dd, —Ar), 7.97 (2H, dd, —Ar), 8.40 (1H, m, Py), 9.61 (2H, m, Py).

Example 20

Epoxidation Reaction Using Onium Salt [8]

An aqueous solution containing 1 wt % of anhydrous sodium sulfate and 1 vol % of acetic acid, which was obtained by the same method as above, then a mixed solution of an aqueous 3 wt % sodium pyrophosphate solution and a 10 wt % ethylenediaminetetraacetic acid solution, furthermore, 1.0 g (3.1 mmol) of 3,3',5,5-tetramethyl-4,4'-bis(2-propen-1-yloxy)-1,1'-biphenyl washed with water, 1.0 ml of toluene, 102 mg (10% mol/substrate) of sodium tungstate dihydrate, 0.36 ml (5% mol/substrate) of an aqueous 8.5% (weight/volume) phosphoric acid solution, 1 ml of water and 81 mg (5% mol/substrate) of 1-[2,3-bis [(4-tert-butylphenylcarbonyloxy)propyl]pyridinium chloride obtained above were previously added and stirred. This mixed solution was heated at 65° C. and thereafter, under a nitrogen stream, added with 0.1 ml (0.5 times mol/substrate) of 45% hydrogen peroxide a total of 5 times, that is, at the initiation of reaction and after 1 hour, 2 hours, 3 hours and 4 hours therefrom, at an inner temperature of 65 to 68° C. The reaction was performed for 1 hour after each addition. Thereafter, 0.10 ml of an aqueous phosphoric acid solution was added to adjust the pH of the aqueous layer to 2.5, and the reaction was performed at an inner temperature of 68° C. while further adding 0.1 ml (0.5 times mol/substrate) of 45% hydrogen peroxide twice every hour, thereby performing the reaction for a total of 9 hours. It was confirmed that 3,3',5,5'-tetramethylbiphenyl-4,4'-diglycidyl ether was produced in a reaction yield of 68%. In addition, 13.7% of a monoepoxy compound as a reaction intermediate and 10.2% (LC area %) of a polar compound were produced.

After the completion of reaction, 10 ml of toluene was additionally added, the aqueous layer was discharged, and the organic phase was washed with 5 ml of an aqueous 5% sodium thiosulfate solution. Furthermore, 5 ml of an aqueous 1N sodium hydroxide solution was added and after stirring for 1 hour, the aqueous layer was discharged. Washing with the same aqueous sodium hydroxide solution was repeated four times, and it was confirmed by LC and NMR that Onium Salt [8] was hydrolyzed and disappeared and tert-butylbenzoic acid as a hydrolysate did not remain. The obtained organic phase was washed with 5 ml of water and then concentrated to obtain 0.9 g of 3,3',5,5'-tetramethylbiphenyl-4,4'-diglycidyl ether with a purity of 68% (LC area %, LC Analysis Condition 2) as a crude crystal. Yield: 56%. This crude crystal contained 6.2 mol % of the ester compound 1 (Compound 22).

The content of tungsten in the compound was analyzed by the method described above. The measurement results are shown in Table 1.

Example 21

Synthesis of Onium Salt [9]

[Chem. 35]

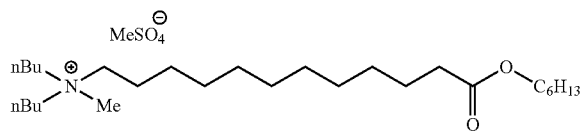

A mixed solution containing 5 g (18.8 mmol) of 12-bromododecanoic acid, 2.35 ml (1 times mol/substrate) of hexanol, 100 ml of toluene and 0.2 ml of sulfuric acid was reacted for 4 hours while azeotropically distilling off the occurring water together with toluene, and after additionally adding 0.47 ml (0.2 times mol/substrate) of hexanol, the reaction was performed for another 2.5 hours. The reaction solution was washed with 100 ml of water, then with 50 ml of a saturated sodium bicarbonate solution and further with 50 ml of water, and the solvent was distilled off to obtain 6.3 g of 2-bromododecanoic acid hexyl ester with a purity of 99% or more. Yield: 92% (GC area %).

A 2.20 g (6.1 mmol) portion of the 12-bromododecanoic acid hexyl ester obtained by the method above and 0.78 g (1.0 times mol/substrate) of dibutylamine were added, and the reaction was performed at 110° C. for 19 hours while additionally adding 0.31 g (0.4 times mol/substrate) of dibutylamine twice halfway therethrough. After the completion of reaction, 20 ml of ethyl acetate was added, and the resulting solution was washed twice with 10 ml of water. The obtained organic layer was concentrated and then subjected to column purification (Silica 60N, 100 g, developing solvent: hexane/ethyl acetate=4/1→2/1) to obtain 1.68 g of 12-N,N-dibutyldodecanoic acid hexyl ester. Yield: 67%.

A 0.165 g (0.4 mmol) portion of the 12-N,N-dibutyldodecanoic acid hexyl ester obtained by the method above was added with 1.2 ml of toluene and 57.5 mg (1.5 times mol/substrate) of dimethyl sulfate and reacted at 70° C. for 3 hours. Production of N,N-diethyl-N-methyl-1-dodecanoic acid hexyl ester ammonium methylsulfate (hereinafter, referred to as Onium Salt [9]) at a conversion ratio of 99% or more was confirmed by NMR analysis. This reaction solution was used directly without purification in the oxidation reaction.

The NMR data of Onium Salt [9] obtained are as follows.

N,N-diethyl-N-methyl-1-dodecanoic acid hexyl ester ammonium methylsulfate 0.85-1.10 (9H, m, —CH3), 1.25-1.80 (34H, m, —CH2-CH2-CH2-), 2.38 (2H, m, —CO—CH2-), 3.07 (3H, s, N—CH3), 3.21 (6H, m, N—CH2-), 3.83 (3H, s, CH3SO2-), 4.12 (2H, m, —COO—CH2).

Example 22

Epoxidation Reaction Using Onium Salt [9]

2.0 g (6.2 mmol) of 3,3',5,5-tetramethyl-4,4'-bis(2-propen-1-yloxy)-1,1'-biphenyl pretreated by the same method as above, 1.2 ml of toluene, 0.205 g (10% mol/substrate) of sodium tungstate dihydrate, 0.64 ml (9% mol/substrate) of an aqueous 8.5% (weight/volume) phosphoric acid solution, 1.4 ml of water and a toluene solution of 12-N,N-dibutyldodecanoic acid hexyl ester ammonium monomethyl sulfate obtained above were previously added and stirred. This mixed solution was heated at 65° C. and thereafter, under a nitrogen stream, added with 0.1 ml (0.5 times mol/substrate) of 45% hydrogen peroxide a total of 6 times, that is, at the initiation of reaction and after 1 hour, 2 hours, 3 hours, 4 hours and 6 hours therefrom, at an inner temperature of 65 to 68° C. The pH of the aqueous phase during reaction was 2.0. The reaction was performed at an inner temperature of 65 to 68° C. for a total of 6 hours, and it was confirmed by the LC analysis above that 3,3',5,5'-tetramethylbiphenyl-4,4'-diglycidyl ether was produced in a reaction yield of 81.3% (LC area %). In addition, 10.7% of a monoepoxy compound and 7.4% (LC area %) of a polar compound were produced.

After the completion of reaction, 20 ml of toluene was additionally added, the aqueous layer was discharged, and the organic phase was washed with 10 ml of an aqueous 5% sodium thiosulfate solution. Furthermore, 10 ml of an aqueous 1N sodium hydroxide solution was added and after stirring for 1 hour, the aqueous layer was discharged. Washing with the same aqueous sodium hydroxide solution was repeated three times, and the resulting solution was washed with 8 ml of water. The obtained organic phase was concentrated to obtain 2.08 g of 3,3',5,5'-tetramethylbiphenyl-4,4'-diglycidyl ether as a crude crystal. Purity: 86.4% (LC area %, LC Analysis Condition 2) and yield: 82%.

A 1 g (2.4 mmol) portion of the crude crystal obtained above was added with 3 ml of toluene and dissolved by heating at 50° C., and 7 ml of methanol was added thereto. The resulting solution was cooled to 6° C., and the precipitated crystal was collected by filtration to obtain 0.52 g of a crystal of 3,3',5,5'-tetramethylbiphenyl-4,4'-diglycidyl ether. It was confirmed by NMR that the crystal was free from Onium Salt (10) and a decomposition product of the onium salt. Purity: 95.6% (LC area %, LC Analysis Condition 2). Recovery percentage: 58%. This crystal contained 0.7 mol % of the ester compound β (Compound 22) and 6.9 mol % of the diol compound γ (Compound 23).

Example 23

Synthesis of Onium Salt [10]

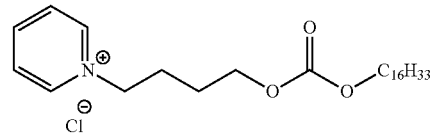

[Chem. 36]

2.81 g (1.0 times mol/chlorobutanol) of hexadecyl chloroformate was added to 1 g (9.2 mmol) of 4-chlorobutanol, 7.4 ml of pyridine and 10 ml of toluene and reacted at room temperature for 3 hours. The precipitated pyridine hydrochloride was separated by filtration using a small amount of toluene, whereby 37 g of a mixed solution of 4-chlorobutyl hexadecyl carbonate, pyridine and toluene. A 1 g portion of the obtained solution was reacted for 10 hours while additionally adding 2 ml of pyridine halfway therethrough. After confirming by NMR analysis of the reaction solution that hexadecyl chloroformate disappeared, pyridine was distilled off, and hexane was added to the resulting residue to obtain a crystal. This crystal was dissolved in ethanol and after filtering insoluble matters, the resulting solution was concentrated to obtain 0.11 g of 1-[(hexadecyloxycarbonyl)oxy]butyl]pyridinium chloride (hereinafter, referred to as Onium Salt [10]). Yield: 95% or more. Purity: 90% or more (NMR).

The NMR data of Onium Salt [10] obtained are as follows.

1-[(Hexadecyloxycarbonyl)oxy]butyl]pyridinium chloride 0.88 (3H, dd, —CH3), 1.2-1.4 (26H, m, —CH2-), 1.66 (2H, m, —CH2-), 1.85 (2H, m, —CH2-), 2.20 (2H, m, —CH2-), 4.11 (2H, dd, —CH2-), 4.20 (2H, dd, —CH2-), 5.20 (2H, dd, N—CH2-), 8.09 (2H, dd, Py), 8.46 (1H, dd, Py), 9.53 (2H, dd, Py).

Example 24

Epoxidation Reaction Using Onium Salt [10]

1.5 g (4.7 mmol) of 3,3',5,5-tetramethyl-4,4'-bis(2-propen-1-yloxy)-1,1'-biphenyl pretreated by the same method as above, 1 ml of toluene, 1 ml of octane, 0.154 g (10% mol/substrate) of sodium tungstate dihydrate, 0.48 ml (9% mol/substrate) of an aqueous 8.5% (weight/volume) phosphoric acid solution, 1.0 ml of water and 0.106 g (5% mol/substrate) of 1-[(hexadecyloxycarbonyl)oxy]butyl]pyridinium chloride obtained above were previously added and stirred. This mixed solution was heated at 65° C. and thereafter, under a nitrogen stream, added with 0.5 ml (0.5 times mol/substrate) of 45% hydrogen peroxide a total of 6 times, that is, at the initiation of reaction and after 1 hour, 2 hours, 3 hours, 4 hours and 6 hours therefrom. The pH of the aqueous phase during reaction was about 3.0. The reaction was performed for a total of 17 hours, that is, for 7 hours at an inner temperature of 65 to 66° C. and for 10 hours at an inner temperature of 68 to 69° C., and it was confirmed by the LC analysis above that 3,3',5,5'-tetramethylbiphenyl-4,4'-diglycidyl ether was produced in a reaction yield of 53.7% (LC area %, Analysis Condition 1). In addition, 10.3% (LC area %) of a monoepoxy compound as a reaction intermediate and 22.0% (LC area %) of a polar compound were produced.

After the completion of reaction, 7.5 ml of toluene was additionally added, the aqueous layer was discharged, and the residue was washed twice with 7.5 ml of water and then washed with 7.5 ml of an aqueous 5% sodium thiosulfate solution. Furthermore, 7.5 ml of an aqueous 1N sodium hydroxide solution was added and after stirring at 25° C. for 1 hour, the aqueous layer was discharged. Washing with the aqueous sodium hydroxide solution was repeated three times at an inner temperature of 30° C. for 30 minutes, and it was confirmed by LC and NMR that Onium Salt [11] was hydrolyzed and disappeared. The obtained organic phase was washed with 25 ml of water and then concentrated to obtain 0.94 g of 3,3',5,5'-tetramethylbiphenyl-4,4'-diglycidyl ether as a crude crystal. Purity: 63.0% (LC area %, LC Analysis Condition 2). Yield: 36%.

Example 25

After adding 14 ml of methanol to 2.0 g of the 3,3',5,5'-tetramethylbiphenyl-4,4'-diglycidyl ether crude crystal obtained in Example 14, the mixture was stirred and crystalized at 50° C. for 3 hours and cooled to 6° C. and thereafter, the crystal was collected by filtration to obtain 1.55 g of 3,3',5,5'-tetramethylbiphenyl-4,4'-diglycidyl ether with a purity of 90.9% (LC area %, LC Analysis Condition 2). Recovery percentage: 79%. This crystal contained 2.6 mol % of the ester compound β (Compound 22) and 0.6 mol % of the diol compound γ (Compound 23). The contents of nitrogen and chlorine in the compound were analyzed by the methods described above. The measurement results are shown in Table 1.

Example 26

After adding 3 ml of methanol to 0.69 g of the 3,3',5,5'-tetramethylbiphenyl-4,4'-diglycidyl ether crude crystal obtained in Example 16, the mixture was stirred and crystalized at 50° C. for 1 hour and cooled to 6° C. and thereafter, the crystal was collected by filtration to obtain 0.52 g of 3,3',5,5'-tetramethylbiphenyl-4,4'-diglycidyl ether with a purity of 90.4% (LC area %, LC Analysis Condition 2). Recovery percentage: 80%. This crystal contained 2.0 mol % of the ester compound β (Compound 22) and 1.2 mol % of the diol compound γ (Compound 23). The content of nitrogen in the compound was analyzed by the method described above. The measurement results are shown in Table 1.

Example 27

After adding 3 ml of toluene to 2.0 g of the 3,3',5,5'-tetramethylbiphenyl-4,4'-diglycidyl ether crude crystal obtained in Example 18, the mixture was heated/dissolved at 50° C., then added with 14 ml of methanol and cooled to 6° C. and thereafter, the crystal was collected by filtration to obtain 1.38 g of 3,3',5,5'-tetramethylbiphenyl-4,4'-diglycidyl ether with a purity of 96.1% (LC area %, LC Analysis Condition 2). Recovery percentage: 71%. This crystal contained 0.2 mol % of the ester compound (3 and 0.5 mol % of the diol compound γ.

The content of nitrogen in the compound was analyzed by the method described above. The measurement results are shown in Table 1.

Example 28

Epoxidation Reaction of 1,5-Cyclooctadiene Using Onium Salt [7]

3.0 g (27.7 mmol) of 1,5-cyclooctadiene (produced by Tokyo Chemical Industry Co., Ltd.), 9 ml of toluene, 0.183 g (2% mol/substrate) of sodium tungstate dihydrate, 0.32 ml (1% mol/substrate) of an aqueous 8.5% (weight/volume) phosphoric acid solution, 3.4 ml of water and 0.16 g (1% mol/substrate) of the 2,3-bis(4-tert-butyl-phenyloxy)-N,N,N-triethyl-1-propane ammonium hydrogen sulfate (Onium Salt [7]) obtained above were added and stirred. This mixed solution was heated at 50° C. and thereafter, under a nitrogen stream, added with 0.9 ml (0.5 times mol/substrate) of 45% hydrogen peroxide a total of 6 times, that is, at the initiation of reaction and after 1 hour, 2 hours, 3 hours, 5 hours and 7 hours therefrom. The pH of the aqueous phase 2 hours after the initiation of reaction was 4.8. The reaction was performed for a total of 9 hours at an inner temperature of 50 to 51° C. It was confirmed by the GC analysis above that 1,2,5,6-diepoxycyclooctane was produced in a reaction yield of 90.2% (GC area %). In addition, 6.6% (LC area %) of a monoepoxy compound as a reaction intermediate and 3.2% (GC area %) of a compound resulting from ring opening of epoxy were produced.

After the completion of reaction, 10 ml of toluene was additionally added, the aqueous layer was discharged, and the residue was washed with 3 ml of water and then washed with 10 ml of an aqueous 5% sodium thiosulfate solution. Furthermore, 10 ml of an aqueous 1N sodium hydroxide solution was added and after stirring at 25° C. for 15 minutes, the aqueous layer was discharged. Washing with the aqueous sodium hydroxide solution was repeated three times at an inner temperature of 30° C. for 30 minutes, and it was confirmed by LC and NMR that Onium Salt [7] was hydrolyzed and disappeared and tert-butylbenzoic acid as a hydrolysate of Onium Salt [7] did not remain. The organic phase was further washed twice with 4 ml of water, and the obtained organic phase was concentrated to obtain 1.0 g of 1,2,5,6-diepoxycyclooctane in a liquid form. Purity: 97% (GC area %) and yield: 26%. This crude crystal contained 1.8 mol % of the ester compound β.

The contents of tungsten and nitrogen in the compound were analyzed by the methods described above. The measurement results are shown in Table 1.

The NMR data of 1,2,5,6-diepoxycyclooctane are as follows, 1,2,5,6-Diepoxycyclooctane:
1.82-2.05 (8H, m, —CH2-), 3.00 (4H, m, —CH—O—).

Reference Example 1

Synthesis of Impurity Specimen

Synthesis of 3-[[3,3',5,5'-tetramethyl-4'-(2-oxylanyl-methoxy)[1,1'-biphenyl]-4-yl]oxy]-1,2-propanediol (compound γ):

50 ml of acetic acid was added to 10 g (0.028 mol) of 3,3',5,5'-tetramethylbiphenyl-4,4'-diglycidyl ether, and the mixture was reacted at an inner temperature of about 85° C. for 9 hours. The acetic acid was distilled off under reduced pressure azeotropically together with toluene to obtain 16.1 g of a residue. This was added with 60 ml of an aqueous 1N sodium hydroxide solution and reacted at room temperature for 2 hours. The precipitated solid containing, as the main component, [[3,3',5,5'-tetramethyl-[1,1'-biphenyl]-4,4'-yl]oxy]bis-(1,2-propanediol) was separated by filtration, and the filter product was washed with 100 ml of ethyl acetate. The ethyl acetate of the wash liquid was combined with the aqueous phase and separated, and the obtained organic phase was concentrated. The residue obtained was purified by column chromatography (Silica 60N, 300 g, developing solvent: hexane/ethyl acetate=from 1/1 to 1/2) to obtain 3.8 g of 3-[[3,3',5,5'-tetramethyl-4'-(2-oxylanylmethoxy)[1,1'-biphenyl]-4-yl]oxy]-1,2-propanediol as a crystal. Yield: 36%. Purity: 95.5% (LC area %, LC Analysis Condition 2).

The NMR data of the diol compound γ obtained are as follows.

3-[[3,3',5,5'-Tetramethyl-4'-(2-oxylanylmethoxy)[1, 1'-biphenyl]-4-yl]oxy]-1,2-propanediol 2.34 (12H, s, —CH3), 2.72 (1H, dd, —CH2-), 2.91 (1H, dd, —CH2-), 3.44 (1H, m, —CH—), 3.76 (1H, dd, —CH2-), 3.79 (2H, m, —CH2-OH), 3.90 (2H, d, O-CH2-CH(OH)), 4.08 (1H, dd, —CH2-), 4.09 (1H, m, CH—OH), 7.18 (4H, s, —C6H2 (Me)2-).

Reference Example 2

Synthesis of 4-tert-butylbenzoic acid-2-hydroxy-3-[[3,3',5,5'-tetramethyl-4'-(2-oxylanylmethoxy)[1,1'-biphenyl]-4-yl]oxy]propyl ester (compound β)

0.08 g (1.5 times mol/substrate) of tert-butylbenzoyl chloride obtained by the method above was added to a mixed solution containing 0.1 g (0.3 mmol) of the diol compound obtained by the method above, 2 ml of toluene and 0.11 ml (3 times mol/substrate) of triethylamine, and the mixture was reacted at room temperature for 5 hours. After the reaction, 6 ml of ethyl acetate and 2 ml of water were added, followed by stirring, and the obtained organic phase was purified by column chromatography (silica 60N, 30 g, developing solvent: hexane/ethyl acetate=4/1) to obtain about 50 mg of 4-tert-butylbenzoic acid-2-hydroxy-3-[[3,3', 5,5'-tetramethyl-4'-(2-oxylanylmethoxy)[1,1'-biphenyl]-4-yl]oxy]propyl ester (compound 13) in about 50 mg. Purity: 96.3% (LC area %, LC Analysis Condition 2).

The NMR data of the compound β obtained are as follows.

4-Tert-butylbenzoic acid-2-hydroxy-3-[[3,3',5,5'-tetramethyl-4'-(2-oxylanylmethoxy) [1,1'-biphenyl]-4-yl]oxy]propyl ester 1.32 (9H, s, t-Bu), 2.34 (12H, s, —CH3), 2.73 (1H, dd, —CH2-), 2.90 (1H, dd, —CH2-), 3.40 (1H, m, —CH—), 3.78 (1H, dd, —CH2-), 3.95 (2H, m, O-CH2-CH(OH)), 4.10 (1H, m, —CH2-), 4.39 (1H, m, CH—OH), 4.60 (2H, m, —CH2-OCO—), 7.18 (4H, s, —C6H2 (Me)2-), 7.49 (2H, d, t-Bu-C6H4-), 7.99 (2H, d, t-Bu-C6H4-).

TABLE 1

| | Tungsten (ppm by weight) | Nitrogen (ppm by weight) | Chlorine (ppm by weight) | Compound β/ Compound α (mol %) |
|---|---|---|---|---|
| Example 2 | 0.06 | 100 | 31 | 2.7 |
| Example 4 | 38 | — | — | 1.1 |
| Example 8 | 0.07 | 84 | <10 | 2.4 |
| Example 9 | — | 10 | <10 | 0.3 |
| Example 12 | 3.46 | — | — | 0.6 |
| Example 14 | 0.58 | 20 | — | 4.6 |
| Example 16 | 0.45 | 56 | — | 5.0 |
| Example 18 | 5.2 | 7 | — | 4.5 |
| Example 20 | 1.82 | — | — | 6.2 |
| Example 22 | 1.6 | — | — | 0.7 |
| Example 25 | — | 7 | <10 | 2.6 |
| Example 26 | — | 15 | — | 2.0 |
| Example 27 | — | 2 | — | 0.2 |
| Example 28 | 0.04 | 7 | — | 1.8 |
| Comparative Example 1 | 142 | 1600 | 30 | — |

While the invention has been described in detail and with reference to specific embodiments thereof, it will be apparent to one skilled in the art that various changes and modifications can be made therein without departing from the spirit and scope of the invention. This application is based on Japanese Patent Application (Patent Application No. 2012-082319) filed on Mar. 30, 2012, Japanese Patent Application (Patent Application No. 2012-226995) filed on Oct. 12, 2012, and Japanese Patent Application (Patent Application No. 2013-012207) filed on Jan. 25, 2013, the contents of which are incorporated herein by way of reference.

The invention claimed is:

1. A method for producing an epoxy compound, the method comprising:
   reacting hydrogen peroxide with a compound having a carbon-carbon double bond in a two-phase reaction system having an organic phase and an aqueous phase, the two-phase reaction system comprising:
      at least one compound selected from the group consisting of a tungsten compound and a molybdenum compound; and
      an onium salt having 20 or more carbon atoms and containing one or more substituents convertible to an active hydrogen-containing functional group or a salt thereof,
   to obtain an epoxy compound;
   after the reacting, converting the one or more substituents contained in the onium salt to an active hydrogen-containing functional group or a salt thereof; and
   separating the onium salt from the epoxy compound.

2. The method of claim 1, wherein said active hydrogen-containing functional group is a hydroxyl group, a carboxyl group, an amino group, a mercapto group, a sulfonic acid group or a phosphoric acid group.

3. The method of claim 1, wherein the two-phase reaction system further comprises at least one acid selected from the group consisting of a phosphoric acid and a phosphonic acid, excluding an onium salt.

4. The method of claim 1, wherein the aqueous phase of the two-phase reaction system has a pH of from 2 to 6.

5. The method of claim 1, wherein said onium salt is an ammonium salt, a pyridinium salt, an imidazolinium salt or a phosphonium salt.

6. The method of claim 1, wherein the converting is achieved by hydrolyzing said one or more substituents with a basic compound.

7. The method of claim 1, further comprising: washing said compound having a carbon-carbon double bond with an acidic aqueous solution prior to the reacting.

8. The method of claim 1, further comprising: washing said compound having a carbon-carbon double bond with an aqueous chelating agent solution prior to the reacting.

9. The method of claim 1, wherein the two-phase reaction system further comprises a chelating agent.

10. A method for producing an epoxy resin, the method comprising:
producing an epoxy compound by the method claimed in claim 1; and
polymerizing the epoxy compound.

11. The method of claim 1, wherein the onium salt is represented by formula (8) to (10), (12) or (31):

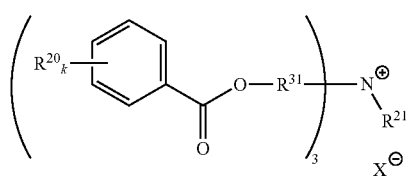
(8)

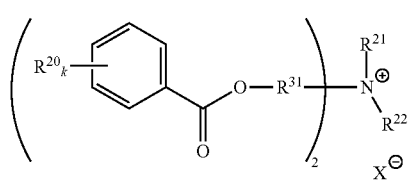
(9)

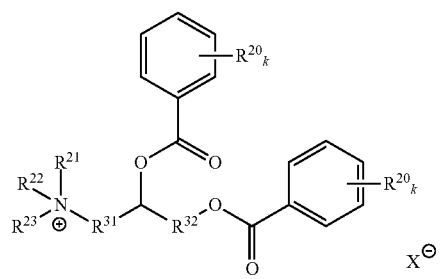
(10)

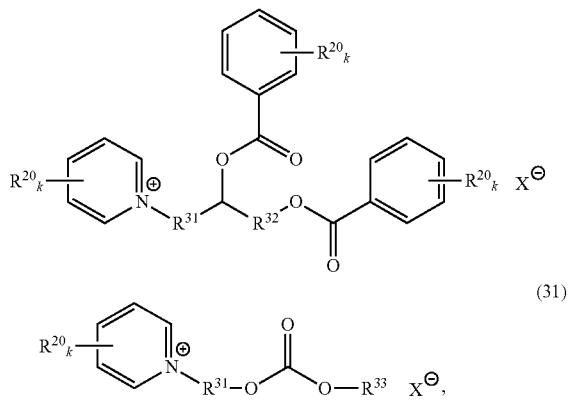
(12)

(31)

wherein $R^{20}$ represents a hydrogen atom, a halogen atom, a cyano group, a nitro group, an alkyl group having a carbon number of 1 to 25, in which a part of carbon atoms is optionally substituted with a heteroatom, a phenyl group, a phenoxy group, a benzyl group, an alkoxycarbonyl group, an N-alkylcarbamoyl group or an N-alkylsulfamoyl group;
each of $R^{21}$ to $R^{23}$ independently represents an alkyl group having a carbon number of 1 to 25, in which a part of carbon atoms is optionally substituted with a heteroatom, or a benzyl group; $R^{20}$ to $R^{23}$ optionally combine in the same compound to form a ring; k represents an integer of 1 to 4;
each of $R^{31}$ and $R^{32}$ independently represents a divalent aliphatic hydrocarbon group having a carbon number of 1 to 25, in which a part of carbon atoms is optionally substituted with a heteroatom;
$R^{33}$ represents a monovalent aliphatic hydrocarbon group having a carbon number of 1 to 25, in which a part of carbon atoms is optionally substituted with a heteroatom, or a monovalent aromatic hydrocarbon group having a carbon number of 4 to 25, which optionally has a substituent;
provided that a plurality of k, $R^{20}$ or $R^{31}$ present in the same compound is optionally the same or different and the total number of carbon atoms contained in the cation moiety in the formulae is 20 or more; and
$X^-$ represents a monovalent anion.

12. The method of claim 1, wherein, during the reacting, the onium salt does not contain an active hydrogen-containing functional group or a salt thereof.

13. The method of claim 1, wherein the active hydrogen-containing functional group is a hydroxyl group.

14. The method of claim 1, wherein the active hydrogen-containing functional group is a carboxyl group.

15. The method of claim 1, wherein the onium salt is an ammonium salt.

16. The method of claim 1, wherein the onium salt is a pyridinium salt.

17. The method of claim 1, wherein the onium salt is an imidazolinium salt.

18. The method of claim 1, wherein the onium salt is a phosphonium salt.

19. A method for producing an epoxy compound, the method comprising:
reacting hydrogen peroxide with a compound having a carbon-carbon double bond in the presence of
at least one compound selected from the group consisting of a tungsten compound and a molybdenum compound; and
an onium salt having 20 or more carbon atoms and containing one or more substituents convertible to an active hydrogen-containing functional group or a salt thereof, wherein said one or more sub substituents contained in the onium salt is an alkoxycarbonyl group or an acyloxy group.

20. The method of claim 19, further comprising, after the reacting, converting the one or more substituents contained in the onium salt to an active hydrogen-containing functional group or a salt thereof, wherein the converting is achieved by hydrolyzing said one or more substituents with a basic compound.

21. A method for producing an epoxy compound, the method comprising:
reacting hydrogen peroxide with a compound having a carbon-carbon double bond in the presence of
at least one compound selected from the group consisting of a tungsten compound and a molybdenum compound; and
an onium salt having 20 or more carbon atoms and containing one or more substituents convertible to an active hydrogen-containing functional group or a salt thereof,
wherein said onium salt is a compound represented by any one of formulae (1) to (3):

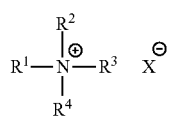

(1)

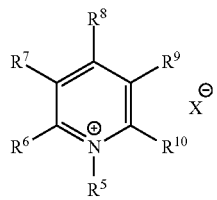

(2)

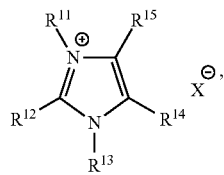

(3)

wherein each of any one or more of $R^1$ to $R^4$, any one or more of $R^5$ to $R^{10}$ and any one or more of $R^{11}$ to $R^{15}$ independently represents —Y—CO—O—Z or —Y—O—CO—Z, Y represents a direct bond or a divalent aliphatic hydrocarbon group having a carbon number of 1 to 25, in which a part of carbon atoms is optionally substituted with a heteroatom and which optionally has a substituent, and Z represents a monovalent aliphatic hydrocarbon group having a carbon number of 1 to 25, in which a part of carbon atoms is optionally substituted with a heteroatom, or a monovalent aromatic hydrocarbon group having a carbon number of 4 to 25, which optionally has a substituent, each of $R^1$ to $R^5$, $R^{11}$ and $R^{13}$, when these are not —Y—CO—O—Z or —Y—O—CO—Z, independently represents an alkyl group having a carbon number of 1 to 25, in which a part of carbon atoms is optionally substituted with a heteroatom and which optionally has a substituent, or a benzyl group, each of $R^6$ to $R^{10}$, $R^{12}$, $R^{14}$ and $R^{15}$, when these are not —Y—CO—O—Z or —Y—O—CO—Z, independently represents a hydrogen atom, a halogen atom, a cyano group, a nitro group, an alkyl group having a carbon number of 1 to 25, in which a part of carbon atoms is optionally substituted with a heteroatom and which optionally has a substituent, a phenyl group, a phenoxy group, a benzyl group, an N-alkylcarbamoyl group or an N-alkylsulfamoyl group, $R^1$ to $R^{15}$ optionally combine in the same compound to form a ring, provided that the total number of carbon atoms contained in $R^1$ to $R^4$ is 20 or more, the total number of carbon atoms contained in $R^5$ to $R^{10}$ is 15 or more, and the total number of carbon atoms contained in $R^{11}$ to $R^{15}$ is 17 or more, and $X^-$ represents a monovalent anion.

* * * * *